US008093016B2

(12) United States Patent
Cervin et al.

(10) Patent No.: US 8,093,016 B2
(45) Date of Patent: Jan. 10, 2012

(54) USE OF AN ASPARTIC PROTEASE (NS24) SIGNAL SEQUENCE FOR HETEROLOGOUS PROTEIN EXPRESSION

(75) Inventors: Marguerite A. Cervin, Redwood City, CA (US); Steven Kim, Fremont, CA (US)

(73) Assignee: Danisco US Inc., Palo Alto, CA (US)

(\*) Notice: Subject to any disclaimer, the term of this patent is extended or adjusted under 35 U.S.C. 154(b) by 136 days.

(21) Appl. No.: 12/600,652

(22) PCT Filed: May 21, 2008

(86) PCT No.: PCT/US2008/006498
§ 371 (c)(1),
(2), (4) Date: Apr. 14, 2010

(87) PCT Pub. No.: WO2008/150376
PCT Pub. Date: Dec. 11, 2008

(65) Prior Publication Data
US 2011/0027830 A1 Feb. 3, 2011

Related U.S. Application Data

(60) Provisional application No. 60/931,072, filed on May 21, 2007, provisional application No. 60/984,430, filed on Nov. 1, 2007.

(51) Int. Cl.
*C12P 21/06* (2006.01)
*C12N 15/00* (2006.01)
*C12N 1/20* (2006.01)
*C07H 21/02* (2006.01)
*C07K 1/00* (2006.01)

(52) U.S. Cl. .............. 435/69.1; 435/252.3; 435/320.1; 536/23.2; 530/350

(58) Field of Classification Search .......... 435/69.1, 435/320.1, 252.3; 536/23.1; 530/350
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 5,650,322 | A | 7/1997 | Clarkson et al. |
| 5,780,708 | A | 7/1998 | Lundquist et al. |
| 5,830,733 | A | 11/1998 | Nevalainen et al. |
| 5,874,276 | A | 2/1999 | Fowler et al. |
| 6,022,725 | A | 2/2000 | Fowler et al. |
| 6,139,902 | A | 10/2000 | Kondo et al. |
| 6,221,644 | B1 | 4/2001 | Berka et al. |
| 6,255,115 | B1 | 7/2001 | Beijersbergen et al. |
| 6,268,328 | B1 | 7/2001 | Mitchinson et al. |
| 6,605,458 | B1 | 8/2003 | Hansen et al. |
| 6,777,589 | B1 | 8/2004 | Lundquist et al. |
| 6,803,499 | B1 | 10/2004 | Anderson et al. |
| 7,354,752 | B2 | 4/2008 | Dunn-Coleman et al. |
| 7,429,476 | B2 | 9/2008 | Clarkson et al. |
| 2008/0196173 | A1 | 8/2008 | Wang et al. |
| 2008/0220498 | A1 | 9/2008 | Cervin et al. |

FOREIGN PATENT DOCUMENTS

| | | |
|---|---|---|
| EP | 0 137 280 A1 | 4/1985 |
| EP | 0 215 594 A2 | 3/1987 |
| EP | 0 238 023 A2 | 9/1987 |
| EP | 0 244 234 A2 | 11/1987 |
| JP | 02-238885 | 9/1990 |
| WO | WO 90/15860 | 12/1990 |
| WO | WO 92/01046 A1 | 1/1992 |
| WO | WO 92/18645 A1 | 10/1992 |
| WO | WO 96/00787 A1 | 1/1996 |
| WO | WO 96/28567 | 9/1996 |
| WO | WO 99/34011 A2 | 7/1999 |
| WO | WO 01/27252 A1 | 4/2001 |
| WO | WO 02/092757 A2 | 11/2002 |
| WO | WO 2005/001036 A2 | 1/2005 |
| WO | WO 2006/043178 A2 | 4/2006 |
| WO | WO 2008/115596 A2 | 9/2008 |
| WO | WO 2008/153712 A2 | 12/2008 |

OTHER PUBLICATIONS

U.S. Appl. No. 12/600,452, filed Nov. 16, 2009, Kim et al.
Altschul, S.F. et al. "Local alignment statistics." *Methods Enzymol* 266:460-80, 1996.
Altschul, S.F. et al. "Basic local alignment search tool." *J. Mol. Biol* 215(3):403-410, 1990.
Bajar, A. et al. "Identification of a fungal cutinase promoter that is inducible by a plant signal via a phosphorylated trans-acting factor." *PNAS USA* 88(18):8208-8212, 1991.
Beaucage, S.L. et al. "Deoxynucleoside phosphoramidites—A new class of key intermediates for deoxypolynucleotide synthesis." *Tetrahedron Lett.* 22(20):1859-1862, 1981.
Berka, R.M. et al. "*Aspergillus niger* var. awamori as a host for the expression of heterologous genes." In *Applications of Enzyme Biotechnology*, eds. J.W. Kelly et al. New York: Plenum Press, pp. 273-292, 1991.
Bhikhabhai, R. et al. "Isolation of cellulolytic enzymes from *Trichoderma reesei* QM 9414." *J. Appl. Biochem.* 6(5-6):336-45, 1984.
Boel, E. et al. "Two different types of intervening sequences in the glucoamylase gene from *Aspergillus niger*." *EMBO J.* 3(7):1581-1585, 1984.
Bower, B. et al. "Hyperexpression and glycosylation of *Trichoderma reesei* EG III." In *Carbohydrases from Trichoderma reesei and other micro-organisms*, eds. M. Claeyssens et al. Cambridge, England: Royal Society of Chemistry, pp. 327-334, 1998.
Brigidi, P. et al. "Genetic transformation of intact cells of *Bacillus subtilis* by electroporation." *FEMS Microbiology Letters* 67(1-2):135-138, 1990.

(Continued)

*Primary Examiner* — Maryam Monshipouri

(57) ABSTRACT

The invention relates to heterologous polypeptide expression and secretion by filamentous fungi and vectors and processes for expression and secretion of such polypeptides. More particularly, the invention discloses the use of a signal sequence form an aspartic protease obtained from *Trichoderma* and referred to as an NSP24 signal sequence.

24 Claims, 17 Drawing Sheets

OTHER PUBLICATIONS

Brisson, N. et al. "Expression of a bacterial gene in plants by using a viral vector." *Nature* 310(5977):511-514, 1984.

Broglie, R. et al. "Light-regulated expression of a pea ribulose-1,5-bisphosphate carboxylase small subunit gene in transformed plant cells." *Science* 224(4651):838-43, 1984.

Brosius, J. "Superpolylinkers in cloning and expression vectors." *DNA (Mary Ann Liebert, Inc.)* 8(10):759-777, 1989.

Brown, T. A. "How to obtain a clone of a specific gene." In *Gene Cloning: An Introduction*, 3rd ed. London: Chapman and Hall, pp. 159-182, 1995.

Brumbauer, A. et al. "Fractionation of cellulase and β-glucosidase in a *Trichoderma reesei* culture liquid by use of two-phase partitioning." *Bioseparation* 7(6):287-295, 1999.

Cadwell, R.C. et al. "Mutagenic PCR." *PCR Methods Appl* 3:S136, 1994.

Campbell, E.I. et al. "Improved transformation efficiency of *Aspergillus niger* using the homologous niaD gene for nitrate reductase." *Current Genetics* 16(1):53-56, 1989.

Cao, Q.N. et al. "Penicillopepsin-JT2, a recombinant enzyme from *Penicillium janthinellum* and the contribution of a hydrogen bond in subsite S3 to k(cat)." *Protein Sci* 9(5):991-1001, 2000.

Chakraborty, B.N. et al. "An electroporation-based system for high-efficiency transformation of germinated conidia of filamentous fungi." *Canadian Journal of Microbiology* 37(11):858-863, 1991.

Coruzzi, G. et al. "Tissue-specific and light-regulated expression of a pea nuclear gene encoding the small subunit of ribulose-1,5-bisphosphate carboxylase." *The EMBO Journal* 3(8):1671-1679, 1984.

Cromwell, G.L. et al. "Efficacy of phytase in improving the bioavailability of phosphorus in soybean meal and corn-soybean meal diets for pigs." *J. Anim Sci.* 71(7):1831-1840, 1993.

Cowieson, A.J. et al. "Carbohydrases, protease, and phytase have an additive beneficial effect in nutritionally marginal diets for broiler chicks." *Poult Sci* 84(12):1860-1867, 2005.

Dayhoff, M.O. et al. "A Model of Evolutionary Change in Proteins." In *Atlas of Protein Sequence and Structure*, vol. 5 supp. 3. ed. M.O. Dayhoff. Silver Spring, MD: National Biomedical Research Foundation, pp. 345-352, 1978.

Deutscher, M.P. "Rethinking your purification procedure." In *Guide to Protein Purification*, Methods in Enzymology, No. 182, ed. M.P. Deutscher. New York: Academic Press, pp. 779-780, 1990.

Ellouz, S. et al. "Analytical separation of *Trichoderma reesei* cellulases by ion-exchange fast protein liquid chromatography." *J. Chromatography* 396:307-317, 1987.

Faber, K.N. et al. "Highly-efficient electrotransformation of the yeast *Hansenula polymorpha.*" *Current Genetics* 25(4):305-310, 1994.

Fernandez-Abalos, J.M. et al. "Posttranslational processing of the xylanase Xys1L from *Streptomyces halstedii* JM8 is carried out by secreted serine proteases." *Microbiology* 149(7):1623-1632, 2003.

Finkelstein, D.B. "Transformation." In *Biotechnology of Filamentous Fungi: Technology and Products*, eds. D.B. Finkelstein et al. Boston, MA: Butterworth-Heinemann, pp. 113-156, 1992.

Fiske, C.H. et al. "The Colorimetric Determination of Phosphorus." *J. Biol. Chem* 66:375-400, 1925.

Fliess, A. et al. "Characterization of cellulases by HPLC separation." *Appl. Microbiol. Biotechnol.* 17(5):314-318, 1983.

Fromm, M.E. et al. "Inheritance and Expression of Chimeric Genes in the Progeny of Transgenic Maize Plants." *Nat Biotech* 8(9):833-839, 1990.

Gill, S.C. et al. "Calculation of protein extinction coefficients from amino acid sequence data." *Analytical Biochemistry* 182(2):319-326, 1989.

Goedegebuur, F. et al. "Cloning and relational analysis of 15 novel fungal endoglucanases from family 12 glycosyl hydrolase." *Current Genetics* 41(2):89-98, 2002.

Goldman, G. H. et al. "Transformation of *Trichoderma harzianum* by high-voltage electric pulse." *Current Genetics* 17(2):169-174, 1990.

Goyal, A. et al. "Characterisation of fungal cellulases." *Biores. Technol* 36:37-50, 1991.

Graessle, S. et al. "Regulated system for heterologous gene expression in *Penicillium chrysogenum.*" *Appl. Environ. Microbiol.* 63(2):753-756, 1997.

de Groot, M.J.A. et al. "*Agrobacterium tumefaciens*-mediated transformation of filamentous fungi." *Nat Biotech* 16(9):839-842, 1998.

Harkki, A. et al. "Genetic engineering of *Trichoderma* to produce strains with novel cellulase profiles." *Enzyme Microb. Technol* 13(3):227-33, 1991.

Harkki, A. et al. "A Novel Fungal Expression System: Secretion of Active Calf Chymosin from the Filamentous Fungus *Trichoderma Reesei.*" *Bio/Technology* 7(6):596-603, 1989.

Hartley, J.L. et al. "DNA cloning using in vitro site-specific recombination." *Genome Research* 10(11):1788-1795, 2000.

Heinonen, J.K. et al. "A new and convenient colorimetric determination of inorganic orthophosphate and its application to the assay of inorganic pyrophosphatase." *Analytical Biochemistry* 113(2):313-317, 1981.

van den Hondel, C. et al. "Heterologous gene expression in filamentous fungi." In *More Gene Manipulations in Fungi*, eds. J.W. Bennett et al. San Diego, CA: Academic Press, pp. 396-428, 1991.

Ilmen, M. et al. "Regulation of cellulase gene expression in the filamentous fungus *Trichoderma reesei.*" *Appl. Environ. Microbiol.* 63(4):1298-1306, 1997.

Innis, M. A. et al. "Expression, Glycosylation, and Secretion of an *Aspergillus* Glucoamylase by *Saccharomyces cerevisiae.*" *Science* 228(4695):21-26, 1985.

Jiang, Q. et al. "Enhanced frequency of *Beauveria bassiana* blastospore transformation by restriction enzyme-mediated integration and electroporation." *Journal of Microbiological Methods* 69(3):512-517, 2007.

Kelly, J.M. et al. "Transformation of *Aspergillus niger* by the amdS gene of *Aspergillus nidulans.*" *The EMBO Journal* 4(2):475-479, 1985.

Kornegay, E.T. et al. "Response of Broilers to Graded Levels of Microbial Phytase Added to Maize-soyabean-Meal-Based Diets Containing Three Levels of Non-Phytate Phosphorus." *British Journal of Nutrition* 75(06):839-852, 1996.

Leuker, C.E. et al. "Sequence and promoter regulation of the PCK1 gene encoding phosphoenolpyruvate carboxykinase of the fungal pathogen *Candida albicans.*" *Gene* 192(2):235-240, 1997.

Libby, C.B. et al. "Effect of amino acid deletions in the O-glycosylated region of *Aspergillus awamori* glucoamylase." *Protein Eng.* 7(9):1109-1114, 1994.

Liu, M. et al. "Conserved Fungal Genes as Potential Targets for Broad-Spectrum Antifungal Drug Discovery." *Eukaryotic Cell* 5(4):638-649, 2006.

Lorito, M. et al. "Biolistic transformation of *Trichoderma harzianum* and *Gliocladium virens* using plasmid and genomic DNA." *Current Genetics* 24(4):349-356, 1993.

Margolin, B.S. et al. "Improved plasmids for gene targeting at the his-3 locus of *Neurospora crassa* by electroporation." *Fungal Genet. Newsletter* 44:34-36, 1997.

Matthes, H.W.D. et al. "Simultaneous rapid chemical synthesis of over one hundred oligonucleotides on a microscale." *EMBO J.* 3(4):801-805, 1984.

May, G. "Fungal Technology." In *Applied Molecular Genetics of Filamentous Fungi*, eds. J.R. Kinghorn et al. Glasgow, UK: Blackie Academic & Professional, pp. 1-27, 1992.

Medve, J. et al. "Ion-exchange chromatographic purification and quantitative analysis of *Trichoderma reesei* cellulases cellobiohydrolase I, II and endoglucanase II by fast protein liquid chromatography." *J. Chromat. A* 808(1-2):153-165, 1998.

Mitchell, D.B. et al. "The phytase subfamily of histidine acid phosphatases: isolation of genes for two novel phytases from the fungi *Aspergillus terreus* and *Myceliophthora thermophila.*" *Microbiology* 143(1):245-252, 1997.

Morinaga, Y. et al. "Improvement of Oligonucleotide-Directed Site-Specific Mutagenesis Using Double-Stranded Plasmid DNA." *Bio/Technology* 2(7):636-639, 1984.

Mullaney, E.J. et al. "Primary structure of the trpC gene from *Aspergillus nidulans.*" *Molecular and General Genetics MGG* 199(1):37-45, 1985.

Munro, C.A. et al. "Chs1 of *Candida albicans* is an essential chitin synthase required for synthesis of the septum and for cell integrity." *Molecular Microbiology* 39(5):1414-1426, 2001.

Murry, L.E. "Genetic Engineering." In *McGraw-Hill Yearbook of Science and Technology*, New York: McGraw Hill, pp. 191-196, 1992.

Needleman, S.B. et al. "A general method applicable to the search for similarities in the amino acid sequence of two proteins." *J. Mol. Biol* 48(3):443-53, 1970.

Nelson, R.M. et al. "A general method of site-specific mutagenesis using a modification of the *Thermus aquaticus* polymerase chain reaction." *Analytical Biochemistry* 180(1):147-151, 1989.

Nevalainen, K.M.H. et al. "The Molecular Biology of *Trichoderma* and its Application to the Expression of Both Homologous and Heterologous Genes." In *Molecular Industrial Mycology*, eds. S.A. Leong et al. New York: Marcel Dekker, pp. 129-148, 1991.

Ninomiya, Y. et al. "Highly efficient gene replacements in *Neurospora* strains deficient for nonhomologous end-joining." *PNAS* 101(33):12248-12253, 2004.

Nunberg, J.H. et al. "Molecular cloning and characterization of the glucoamylase gene of *Aspergillus awamori*." *Mol. Cell. Biol.* 4(11):2306-2315, 1984.

Nyyssönen, E. et al. "Efficient Production of Antibody Fragments by the Filamentous Fungus *Trichoderma reesei*." *Nat Biotech* 11(5):591-595, 1993.

Pearson, W.R. et al. "Improved Tools for Biological Sequence Comparison." *Proc. Natl. Acad. Sci. USA* 85(8):2444-2448, 1988.

Penttilä, M. et al. "A versatile transformation system for the cellulolytic filamentous fungus *Trichoderma reesei*." *Gene* 61(2):155-64, 1987.

Potrykus, I. et al. "Molecular and general genetics of a hybrid foreign gene introduced into tobacco by direct gene transfer." *Molecular and General Genetics MGG* 199(2):169-177, 1985.

Pourquié, J. et al. "Scale up of cellulase production and utilization." In *Biochemistry and Genetics of Cellulose Degradation*, eds. J.P. Aubert et al. London: Academic Press, pp. 71-86, 1988.

Richey, M.G. et al. "Transformation of Filamentous Fungi with Plasmid DNA by Electroporation." *Phytopathology* 79(8):844, 1989.

Rogers, S.G. et al. "Gene Transfer in Plants: Production of Transformed Plants Using Ti Plasmid Vectors." In *Methods for Plant Molecular Biology*, eds. A. Weissbach et al. New York: Academic Press, pp. 423-436, 1988.

Ruiz-Diez, B. "Strategies for the transformation of filamentous fungi." *Journal of Applied Microbiology* 92(2):189-195, 2002.

Saiki, R.K. et al. "Primer-directed enzymatic amplification of DNA with a thermostable DNA polymerase." *Science* 239(4839):487-491, 1988.

Sanchez, O. et al. "Efficient transformation of *Aspergillus nidulans* by electroporation of germinated conidia." *Fungal Genet. Newsletter* 43:48-51, 1996.

Sarkar, G. et al. "The "megaprimer" method of site-directed mutagenesis." *Bio Techniques* 8(4):404-7, 1990.

Schiestl, R.H. et al. "Introducing DNA into Yeast by Transformation." *Methods* 5(2):79-85, 1993.

Scopes, R.K. et al. "Purification of all glycolytic enzymes from one muscle extract." In *Carbohydrate Metabolism—Part E*, Methods in Enzymology, No. 90, ed. W.A. Wood. New York: Academic Press, pp. 479-490, 1982.

Sheir-Neiss, G. et al. "Characterization of the secreted cellulases of *Trichoderma reesei* wild type and mutants during controlled fermentations." *Applied Microbiology and Biotechnology* 20(1):46-53, 1984.

Shpaer, E.G. "GeneAssist: Smith-Waterman and other database similarity searches and identification of motifs." in *Sequence Data Analysis Guidebook*, Methods in Molecular Biology, No. 70, Totowa, NJ: Humana Press, pp. 173-87, 1997.

Smith, T.F. et al. "Comparison of biosequences." *Adv. Appl. Math* 2:482-489, 1981.

Takamatsu, N. et al. "Expression of bacterial chloramphenicol acetyltransferase gene in tobacco plants mediated by TMV-RNA." *EMBO J.* 6(2):307-311, 1987.

van Tilbeurgh, H. et al. "Separation of endo- and exo-type cellulases using a new affinity chromatography method." *FEBS Letters* 169(2):215-218, 1984.

Timberlake, W.E. "Cloning and Analysis of Fungal Genes." In *More Gene Manipulations in Fungi*, eds. J.W. Bennett et al. San Diego, CA: Academic Press, pp. 70-76, 1991. pp. 50-85.

Tomaz, C.T. et al. "Studies on the chromatographic fractionation of *Trichoderma reesei* cellulases by hydrophobic interaction." *J. Chromat. A* 865(1-2):123-128, 1999.

Ward, M. et al. "Use of *Aspergillus* overproducing mutants, cured for intergrated plasmid, to overproduce heterologous proteins." *Applied Microbiology and Biotechnology* 39(6):738-743, 1993.

Winter, J. et al. "The expression of heat shock protein and cognate genes during plant development." *Results and Problems in Cell Differentiation* 17:85-105, 1991.

Yelton, M.M. et al. "Transformation of *Aspergillus nidulans* by using a trpC plasmid." *Proc. Natl. Acad. Sci. U.S.A* 81(5):1470-4, 1984.

PCT/US2008/006498 Search Report.

Figure 1a

ATGCAGACCTTTGGAGCTTTTCTCGTTTCCTTCCTCGCCGCCAGCGGCCTGGCCGCG
GCCCTCCCCACCGAGGGTCAGAAGACGGCTTCCGTCGAGGTCCAGTACAACAAGAAC
TACGTCCCCCACGGCCCTACTGCTCTCTTCAAGGCCAAGAGAAAGTATGGCGCTCCC
ATCAGCGACAACCTGAAGTCTCTCGTGGCTGCCAGGCAGGCCAAGCAGGCTCTCGCC
AAGCGCCAGACCGGCTCGGCGCCCAACCACCCCAGTGACAGCGCCGATTCGGAGTAC
ATCACCTCCGTCTCCATCGGCACTCCGGCTCAGGTCCTCCCCCTGGACTTTGACACC
GGCTCCTCCGACCTGTGGGTCTTTAGCTCCGAGACGCCCAAGTCTTCGGCCACCGGC
CACGCCATCTACACGCCCTCCAAGTCGTCCACCTCCAAGAAGGTGTCTGGCGCCAGC
TGGTCCATCAGCTACGGCGACGGCAGCAGCTCCAGCGGCGATGTCTACACCGACAAG
GTCACCATCGGAGGCTTCAGCGTCAACACCCAGGGCGTCGAGTCTGCCACCCGCGTG
TCCACCGAGTTCGTCCAGGACACGGTCATCTCTGGCCTCGTCGGCCTTGCCTTTGAC
AGCGGCAACCAGGTCAGGCCGCACCCGCAGAAGACGTGGTTCTCCAACGCCGCCAGC
AGCCTGGCTGAGCCCCTTTTCACTGCCGACCTGAGGCACGGACAGAGTAAGTAGACA
CTCACTGGAATTCGTTCCTTTCCCGATCATCATGAAAGCAAGTAGACTGACTGAACC
AAACAACTAGACGGCAGCTACAACTTTGGCTACATCGACACCAGCGTCGCCAAGGGC
CCCGTTGCCTACACCCCGTTGACAACAGCCAGGGCTTCTGGGAGTTCACTGCCTCG
GGCTACTCTGTCGGCGGCGGCAAGCTCAACCGCAACTCCATCGACGGCATTGCCGAC
ACCGGCACCACCCTGCTCCTCCTCGACGACAACGTCGTCGATGCCTACTACGCCAAC
GTCCAGTCGGCCCAGTACGACAACCAGCAGGAGGGTGTCGTCTTCGACTGCGACGAG
GACCTCCCTTCGTTCAGCTTCGGTGTTGGAAGCTCCACCATCACCATCCCTGGCGAT
CTGCTGAACCTGACTCCCCTCGAGGAGGGCAGCTCCACCTGCTTCGGTGGCCTCCAG
AGCAGCTCCGGCATTGGCATCAACATCTTTGGTGACGTTGCCCTCAAGGCTGCCCTG
GTTGTCTTTGACCTCGGCAACGAGCGCCTGGGCTGGGCTCAGAAATAA (SEQ ID NO:1)

Figure 1b

MQTFGAFLVSFLAASGLAAALPTEGQKTASVEVQYNKNYVPHGPTALFKAKRKYG
APISDNLKSLVAARQAKQALAKRQTGSAPNHPSDSADSEYITSVSIGTPAQVLPLDF
DTGSSDLWVFSSETPKSSATGHAIYTPSKSSTSKKVSGASWSISYGDGSSSSGDVY
TDKVTIGGFSVNTQGVESATRVSTEFVQDTVISGLVGLAFDSGNQVRPHPQKTWFS
NAASSLAEPLFTADLRHGQNGSYNFGYIDTSVAKGPVAYTPVDNSQGFWEFTASG
YSVGGGKLNRNSIDGIADTGTTLLLLDDNVVDAYYANVQSAQYDNQQEGVVFDCDE
DLPSFSFGVGSSTITIPGDLLNLTPLEEGSSTCFGGLQSSSGIGINIFGDVALKAALVV
FDLGNERLGWAQK (SEQ ID NO:2)

FIG 4a

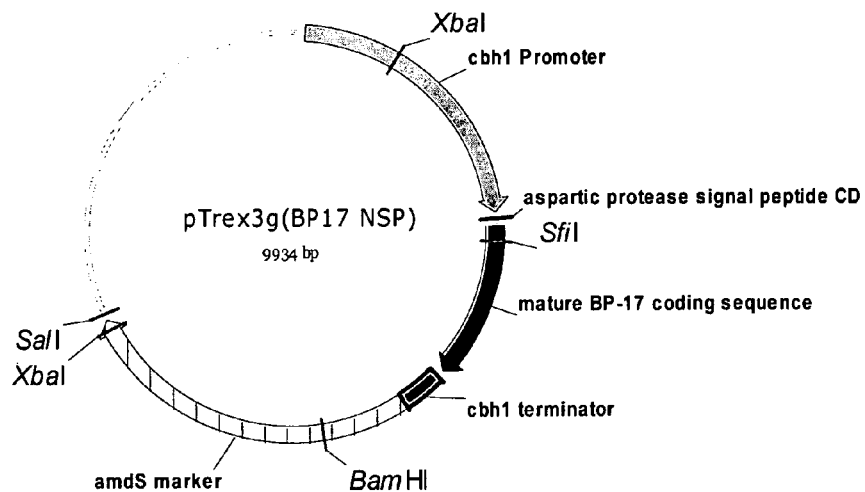

Figure 4b

```
NDTPASGYQV EKVVILSRHG VRAPTKMTQT MRDVTPNTWP EWPVKLGYIT
PRGEHLISLM GGFYRQKFQQ QGILSQGSCP TPNSIYVWAD VDQRTLKTGE
AFLAGLAPQC GLTIHHQQNL EKADPLFHPV KAGTCSMDKT QVQQAVEKEA
QTPIDNLNQH YIPFLALMNT TLNFSTSAWC QKHSADKSCD LGLSMPSKLS
IKDNGNKVAL DGAIGLSSTL AEIFLLEYAQ GMPQAAWGNI HSEQEWASLL
KLHNVQFDLM ARTPYIARHN GTPLLQAISN ALNPNATESK LPDISPDNKI
LFIAGHDTNI ANIAGMLNMR WTLPGQPDNT PPGGALVFER LADKSGKQYV
SVSMVYQTLE QLRSQTPLSL NQPAGSVQLK IPGCNDQTAE GYCPLSTFTR
VVSQSVEPGC QLQ    (SEQ ID NO:5)
```

FIGURE 6b (SEQ ID NO:6) DNA sequence of pTrex4-laccase D opt:
AAGCGCCTGCAGCCACTTGCAGTCCCGTGGAATTCTCACGGTGAATGTAGGCCTTTTGTAGGGTAGGAATTGTCACTCAA
GCACCCCCAACCTCCATTACGCCTCCCCCATAGAGTTCCCAATCAGTGAGTCATGGCACTGTTCTCAAATAGATTGGGGA
GAAGTTGACTTCCGCCCAGAGCTGAAGGTCGCACAACCGCATGATATAGGGTCGGCAACGGCAAAAAAGCACGTGGCTCA
CCGAAAAGCAAGATGTTTGCGATCTAACATCCAGGAACCTGGATACATCCATCATCACGCACGACCACTTTGATCTGCTG
GTAAACTCGTATTCGCCCTAAACCGAAGTGACGTGGTAAATCTACACGTGGGCCCCTTTCGGTATACTGCGTGTGTCTTC
TCTAGGTGCCATTCTTTTCCCTTCCTCTAGTGTTGAATTGTTTGTGTTGGAGTCCGAGCTGTAACTACCTCTGAATCTCT
GGAGAATGGTGGACTAACGACTACCGTGCACCTGCATCATGTATATAATAGTGATCCTGAGAAGGGGGGTTTGGAGCAAT
GTGGGACTTTGATGGTCATCAAACAAAGAACGAAGACGCCTCTTTTGCAAAGTTTTGTTTCGGCTACGGTGAAGAACTGG
ATACTTGTTGTGTCTTCTGTGTATTTTTGTGGCAACAAGAGGCCAGAGACAATCTATTCAAACACCAAGCTTGCTCTTTT
GAGCTACAAGAACCTGTGGGTATATATCTAGAGTTGTGAAGTCGGTAATCCCGCTGTATAGTAATACGAGTCGCATCTA
AATACTCCGAAGCTGCTGCGAACCCGGAGAATCGAGATGTGCTGGAAAGCTTCTAGCGAGCGGCTAAATTAGCATGAAAG
GCTATGAGAAATTCTGGAGACGGCTTGTTGAATCATGGCGTTCCATTCTTCGACAAGCAAAGCGTTCCGTCGCAGTAGCA
GGCACTCATTCCCGAAAAAACTCGGAGATTCCTAAGTAGCGATGGAACCGGAATAATATAATAGGCAATACATTGAGTTG
CCTCGACGGTTGCAATGCAGGGGTACTGAGCTTGGACATAACTGTTCCGTACCCCACCTCTTCTCAACCTTTGGCGTTTC
CCTGATTCAGCGTACCCGTACAAGTCGTAATCACTATTAACCCAGACTGACCGGACGTGTTTTGCCCTTCATTTGGAGAA
ATAATGTCATTGCGATGTGTAATTTGCCTGCTTGACCGACTGGGGCTGTTCGAAGCCCGAATGTAGGATTGTTATCCGAA
CTCTGCTCGTAGAGGCATGTTGTGAATCTGTGTCGGGCAGGACACGCCTCGAAGGTTCACGGCAAGGGAAACCACCGATA
GCAGTGTCTAGTAGCAACCTGTAAAGCCGCAATGCAGCATCACTGGAAAATACAAACCAATGGCTAAAAGTACATAAGTT
AATGCCTAAAGAAGTCATATACCAGCGGCTAATAATTGTACAATCAAGTGGCTAAACGTACCGTAATTTGCCAACGGCTT
GTGGGGTTGCAGAAGCAACGGCAAAGCCCCACTTCCCCACGTTTGTTTCTTCACTCAGTCCAATCTCAGCTGGTGATCCC
CCAATTGGGTCGCTTGTTTGTTCCGGTGAAGTGAAAGAAGACAGAGGTAAGAATGTCTGACTCGGAGCGTTTTGCATACA
ACCAAGGGCAGTGATGGAAGACAGTGAAATGTTGACATTCAAGGAGTATTTAGCCAGGGATGCTTGAGTGTATCGTGTAA
GGAGGTTTGTCTGCCGATACGACGAATACTGTATAGTCACTTCTGATGAAGTGGTCCATATTGAAATGTAAGTCGGCACT
GAACAGGCAAAAGATTGAGTTGAAACTGCCTAAGATCTCGGGCCCTCGGGCCTTCGGCCTTTGGGTGTACATGTTTGTGC
TCCGGGCAAATGCAAAGTGTGGTAGGATCGAACACACTGCTGCCTTTACCAAGCAGCTGAGGGTATGTGATAGGCAAATG
TTCAGGGGCCACTGCATGGTTTCGAATAGAAAGAGAAGCTTAGCCAAGAACAATAGCCGATAAAGATAGCCTCATTAAAC
GGAATGAGCTAGTAGGCAAAGTCAGCGAATGTGTATATATAAAGGTTCGAGGTCCGTGCCTCCCTCATGCTCTCCCCATC
TACTCATCAACTCAGATCCTCCAGGAGACTTGTACACCATCTTTTGAGGCACAGAAACCCAATAGTCAACCGCGGACTGC
GCATCATGTATCGGAAGTTGGCCGTCATCTCGGCCTTCTTGGCCACAGCTCGTGCTCAGTCGGCCTGCACTCTCCAATCG
GAGACTCACCCGCCTCTGACATGGCAGAAATGCTCGTCTGGTGGCACTTGCACTCAACAGACAGGCTCCGTGGTCATCGA
CGCCAACTGGCGCTGGACTCACGCTACGAACAGCAGCACGAACTGCTACGATGGCAACACTTGGAGCTCGACCCTATGTC
CTGACAACGAGACCTGCGCGAAGAACTGCTGTCTGGACGGTGCCGCCTACGCGTCCACGTACGGAGTTACCACGAGCGGT
AACAGCCTCTCCATTGGCTTTGTCACCCAGTCTGCGCAGAAGAACGTTGGCGCTCGCCTTTACCTTATGGCGAGCGACAC
GACCTACCAGGAATTCACCCTGCTTGGCAACGAGTTCTCTTTCGATGTTGATGTTTCGCAGCTGCCGTAAGTGACTTACC
ATGAACCCCTGACGTATCTTCTTGTGGGCTCCCAGCTGACTGGCCAATTTAAGGTGCGGCTTGAACGGAGCTCTCTACTT
CGTGTCCATGGACGCGGATGGTGGCGTGAGCAAGTATCCCACCAACACCGCTGGCGCCAAGTACGGCACGGGGTACTGTG
ACAGCCAGTGTCCCCGCGATCTGAAGTTCATCAATGGCCAGGCCAACGTTGAGGGCTGGGAGCCGTCATCCAACAACGCA
AACACGGGCATTGGAGGACACGGAAGCTGCTGCTCTGAGATGGATATCTGGGAGGCCAACTCCATCTCCGAGGCTCTTAC
CCCCCACCCTTGCACGACTGTCGGCCAGGAGATCTGCGAGGGTGATGGGTGCGGCGGACTTACTCCGATAACAGATATG
GCGGCACTTGCGATCCCGATGGTCGCACTGGAACCCATACCGCCTGGGCAACACCAGCTTCTACGGCCCTGGCTCAAGC
TTTACCCTCGATACCACCAAGAAATTTGACCGTTGTCACCCAGTTCGAGACGTCGGGTGCCATCAACCGATACTATGTCCA
GAATGGCGTCACTTTCCAGCAGCCCAACGCCGAGCTTGGTAGTTACTCTGGCAACGAGCTCAACGATGATTACTGCACAG
CTGAGGAGGCAGAATTCGGCGGATCCTCTTTCTCAGACAAGGGCGGCCTGACTCAGTTCAAGAAGGCTACCTCTGGCGGC
ATGGTTCTGGTCATGAGTCTGTGGGATGATGTGAGTTTGATGGACAAACATGCGCGTTGACAAAGAGTCAAGCAGCTGAC
TGAGATGTTACAGTACTACGCCAACATGCTGTGGCTGGACTCCACCTACCCGACAAACGAGACCTCCTCCACACCCGGTG
CCGTGCGCGGAAGCTGCTCCACCAGCTCCGGTGTCCCTGCTCAGGTCGAATCTCAGTCTCCCAACGCCAAGGTCACCTTC
TCCAACATCAAGTTCGGACCCATTGGCAGCACCGGCAACCCTAGCGGCGGCAACCCTCCCGGCGGAAACCCGCCTGGCAC
CACCACCACCCGCCGCCCAGCCACTACCACCACTGAAGCTCTCCCGGACCTACTAGTGTCGCCGTTTACAAACGCGCTATTG
GACCAGTTGCTGATCTGCACATCGTTAACAAGGATTTGGCCCCAGACGGCGTCCAGCCCCAACTGTTCTGGCCGGTGGA
ACTTTTCCGGGCACGCTGATTACCGGTCAAAAGGGCGACAACTTCCAGCTGAACGTGATTGATGACCTGACCGACGATCG
CATGTTGACCCCTACTTCGATCCATTGGCATGGTTTCTTCCAGAAGGGAACCGCCTGGGCCGACGGTCCGGCTTTCGTTA
CACAGTGCCCTATTATCGCAGACAACTCCTTCCTCTACGATTTCGACGTTCCCGACCAGGCGGGCACCTTCTGGTACCAC
TCACACTTGTCTACACAGTACTGCGACGGTCTGCGCGGTGCCTTCGTTGTTTACGACCCCAACGACCCTCACAAGGACCT
TTATGATGTCGATGACGGTGGCACAGTTATCACATTGGCTGACTGGTATCACGTCCTCGCTCAGACCGTTGTCGGAGCTG
CTACACCCGACTCTACGCTGATTAACGGCTTGGGACGCAGCCAGACTGGCCCCGCCGACGCTGAGCTGGCCGTTATCTCT

Figure 6C

```
GTTGAACACAACAAGAGATACCGTTTCAGACTCGTCTCCATCTCGTGCGATCCCAACTTCACTTTTAGCGTCGACGGTCA
CAACATGACGGTTATCGAGGTTGATGGCGTGAATACCCGCCCTCTCACCGTCGATTCCATTCAAATTTTCGCCGGCCAGC
GATACTCCTTTGTGCTGAATGCCAATCAGCCCGAGGATAACTACTGGATCCGCGCTATGCCTAACATCGGACGAAACACC
ACTACCCTTGATGGCAAGAATGCCGCTATCCTGCGATACAAGAACGCCAGCGTTGAGGAGCCCAAAACCGTCGGAGGACC
CGCGCAGAGCCCATTGAACGAGGCCGACCTGCGACCTCTGGTGCCCGCTCCTGTCCCTGGCAACGCAGTTCCTGGTGGTG
CGGACATCAACCACCGCCTGAACCTGACATTCAGCAACGGCCTCTTCTCTATCAATAACGCATCATTTACAAACCCCAGC
GTCCCTGCCTTGTTGCAGATTCTTTCCGGCGCACAAAACGCTCAGGATCTGCTTCCCACCGGTTCTTATATCGGCTTGGA
GTTGGGCAAGGTCGTTGAACTCGTGATCCCTCCCTTGGCCGTTGGTGGCCCCCATCCATTCCACTTGCACGGCCACAACT
TTTGGGTCGTCCGAAGCGCTGGTTCTGACGAGTATAATTTCGACGATGCAATTTTGCGCGACGTGGTCAGCATTGGCGCG
GGAACTGACGAGGTTACTATCCGTTTTGTCACTGATAACCCAGGCCCTTGGTTCCTCCATTGCCACATCGACTGGCACCT
CGAAGCCGGCCTCGCCATTGTTTTCGCCGAAGGCATCAATCAAACCGCAGCCGCCAACCCGACTCCACAGGCCTGGGACG
AACTCTGCCCCAAGTATAACGGACTCTCCGCTTCCCAGAAAGTGAAGCCCAAGAAGGGAACAGCCATCTAAGGCGCGCCG
CGCGCCAGCTCCGTGCGAAAGCCTGACGCACCGGTAGATTCTTGGTGAGCCCGTATCATGACGGCGGCGGGAGCTACATG
GCCCCGGGTGATTTATTTTTTTTGTATCTACTTCTGACCCTTTTCAAATATACGGTCAACTCATCTTTCACTGGAGATGC
GGCCTGCTTGGTATTGCGATGTTGTCAGCTTGGCAAATTGTGGCTTTCGAAAACACAAAACGATTCCTTAGTAGCCATGC
ATTTTAAGATAACGGAATAGAAGAAAGAGGAAATTAAAAAAAAAAAAAAAACAAACATCCCGTTCATAACCCGTAGAATC
GCCGCTCTTCGTGTATCCCAGTACCAGTTTATTTTGAATAGCTCGCCCGCTGGAGAGCATCCTGAATGCAAGTAACAACC
GTAGAGGCTGACACGGCAGGTGTTGCTAGGGAGCGTCGTGTTCTACAAGGCCAGACGTCTTCGCGGTTGATATATATGTA
TGTTTGACTGCAGGCTGCTCAGCGACGACAGTCAAGTTCGCCCTCGCTGCTTGTGCAATAATCGCAGTGGGGAAGCCACA
CCGTGACTCCCATCTTTCAGTAAAGCTCTGTTGGTGTTTATCAGCAATACACGTAATTTAAACTCGTTAGCATGGGGCTG
ATAGCTTAATTACCGTTTACCAGTGCCGCGGTTCTGCAGCTTTCCTTGGCCCGTAAAATTCGGCGAAGCCAGCCAATCAC
CAGCTAGGCACCAGCTAAACCCTATAATTAGTCTCTTATCAACACCATCCGCTCCCCCGGGATCAATGAGGAGAATGAGG
GGGATGCGGGGCTAAAGAAGCCTACATAACCCTCATGCCAACTCCCAGTTTACACTCGTCGAGCCAACATCCTGACTATA
AGCTAACACAGAATGCCTCAATCCTGGGAAGAACTGGCCGCTGATAAGCGCGCCCGCCTCGCAAAAACCATCCCTGATGA
ATGGAAAGTCCAGACGCTGCCTGCGGAAGACAGCGTTATTGATTTCCCAAAGAAATCGGGGATCCTTTCAGAGGCCGAAC
TGAAGATCACAGAGGCCTCCGCTGCAGATCTTGTGTCCAAGCTGGCGGCCGGAGAGTTGACCTCGGTGGAAGTTACGCTA
GCATTCTGTAAACGGGCAGCAATCGCCCAGCAGTTAGTAGGGTCCCCTCTACCTCTCAGGGAGATGTAACAACGCCACCT
TATGGGACTATCAAGCTGACGCTGGCTTCTGTGCAGACAAACTGCGCCCACGAGTTCTTCCCTGACGCCGCTCTCGCGCA
GGCAAGGGAACTCGATGAATACTACGCAAAGCACAAGAGACCCGTTGGTCCACTCCATGGCCTCCCCATCTCTCTCAAAG
ACCAGCTTCGAGTCAAGGTACACCGTTGCCCCTAAGTCGTTAGATGTCCCTTTTTGTCAGCTAACATATGCCACCAGGGC
TACGAAACATCAATGGGCTACATCTCATGGCTAAACAAGTACGACGAAGGGGACTCGGTTCTGACAACCATGCTCCGCAA
AGCCGGTGCCGTCTTCTACGTCAAGACCTCTGTCCCGCAGACCCTGATGGTCTGCGAGACAGTCAACAACATCATCGGGC
GCACCGTCAACCCACGCAACAAGAACTGGTCGTGCGGCGGCAGTTCTGGTGGTGAGGGTGCGATCGTTGGGATTCGTGGT
GGCGTCATCGGTGTAGGAACGGATATCGGTGGCTCGATTCGAGTGCCGGCCGCGTTCAACTTCCTGTACGGTCTAAGGCC
GAGTCATGGGCGGCTGCCGTATGCAAAGATGGCGAACAGCATGGAGGGTCAGGAGACGGTGCACAGCGTTGTCGGGCCGA
TTACGCACTCTGTTGAGGGTGAGTCCTTCGCCTCTTCCTTCTTTTCCTGCTCTATACCAGGCCTCCACTGTCCTCCTTTC
TTGCTTTTTATACTATATACGAGACCGGCAGTCACTGATGAAGTATGTTAGACCTCCGCCTCTTCACCAAATCCGTCCTC
GGTCAGGAGCCATGGAAATACGACTCCAAGGTCATCCCCATGCCCTGGCGCCAGTCCGAGTCGGACATTATTGCCTCCAA
GATCAAGAACGGCGGGCTCAATATCGGCTACTACAACTTCGACGGCAATGTCCTTCCACACCCTCCTATCCTGCGCGGCG
TGGAAACCACCGTCGCCGCACTCGCCAAAGCCGGTCACACCGTGACCCCGTGGACGCCATACAAGCACGATTTCGGCCAC
GATCTCATCTCCCATATCTACGCGGCTGACGGCAGCGCCGACGTAATGCGCGATATCAGTGCATCCGGCGAGCCGGCGAT
TCCAAATATCAAAGACCTACTGAACCCGAACATCAAAGCTGTTAACATGAACGAGCTCTGGGACACGCATCTCCAGAAGT
GGAATTACCAGATGGAGTACCTTGAGAAATGGCGGGAGGCTGAAGAAAAGGCCGGGAAGGAACTGGACGCCATCATCGCG
CCGATTACGCCTACCGCTGCGGTACGGCATGACCAGTTCCGGTACTATGGGTATGCCTCTGTGATCAACCTGCTGGATTT
CACGAGCGTGGTTGTTCCGGTTACCTTTGCGGATAAGAACATCGATAAGAAGAATGAGAGTTTCAAGGCGGTTAGTGAGC
TTGATGCCCTCGTGCAGGAAGAGTATGATCCGGAGGCGTACCATGGGGCACCGGTTGCAGTGCAGGTTATCGGACGGAGA
CTCAGTGAAGAGAGGACGTTGGCGATTGCAGAGGAAGTGGGGAAGTTGCTGGGAAATGTGGTGACTCCATAGCTAATAAG
TGTCAGATAGCAATTTGCACAAGAAATCAATACCAGCAACTGTAAATAAGCGCTGAAGTGACCATGCCATGCTACGAAAG
AGCAGAAAAAAACCTGCCGTAGAACCGAAGAGATATGACACGCTTCCATCTCTCAAAGGAAGAATCCCTTCAGGGTTGCG
TTTCCAGTCTAGACACGTATAACGGCACAAGTGTCTCTCACCAAATGGGTTATATCTCAAATGTGATCTAAGGATGGAAA
GCCCAGAATCTAGGCCTATTAATATTCCGGAGTATACGTAGCCGGCTAACGTTAACAACCGGTACCTCTAGAACTATAGC
TAGCATGCGCAAATTTAAAGCGCTGATATCGATCGCGCGCAGATCCATATATAGGGCCCGGGTTATAATTACCTCAGGTC
GACGTCCCATGGCCATTCGAATTCGTAATCATGGTCATAGCTGTTTCCTGTGTGAAATTGTTATCCGCTCACAATTCCAC
ACAACATACGAGCCGGAAGCATAAAGTGTAAAGCCTGGGGTGCCTAATGAGTGAGCTAACTCACATTAATTGCGTTGCGC
TCACTGCCCGCTTTCCAGTCGGGAAACCTGTCGTGCCAGCTGCATTAATGAATCGGCCAACGCGCGGGGAGAGGCGGTTT
GCGTATTGGGCGCTCTTCCGCTTCCTCGCTCACTGACTCGCTGCGCTCGGTCGTTCGGCTGCGGCGAGCGGTATCAGCTC
ACTCAAAGGCGGTAATACGGTTATCCACAGAATCAGGGGATAACGCAGGAAAGAACATGTGAGCAAAAGGCCAGCAAAAG
```

Figure 6D
GCCAGGAACCGTAAAAAGGCCGCGTTGCTGGCGTTTTTCCATAGGCTCCGCCCCCTGACGAGCATCACAAAAATCGACG
CTCAAGTCAGAGGTGGCGAAACCCGACAGGACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCGGGAAGCGTGGCGCTTTCTCATAGCTCACGC
TGTAGGTATCTCAGTTCGGTGTAGGTCGTTCGCTCCAAGCTGGGCTGTGTGCACGAACCCCCCGTTCAGCCCGACCGCTG
CGCCTTATCCGGTAACTATCGTCTTGAGTCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTGGCCTAACTACGGCTACACTAGAAGAACA
GTATTTGGTATCTGCGCTCTGCTGAAGCCAGTTACCTTCGGAAAAAGAGTTGGTAGCTCTTGATCCGGCAAACAAACCAC
CGCTGGTAGCGGTGGTTTTTTTGTTTGCAAGCAGCAGATTACGCGCAGAAAAAAAGGATCTCAAGAAGATCCTTTGATCT
TTTCTACGGGGTCTGACGCTCAGTGGAACGAAAACTCACGTTAAGGGATTTTGGTCATGAGATTATCAAAAAGGATCTTC
ACCTAGATCCTTTTAAATTAAAAATGAAGTTTTAAATCAATCTAAAGTATATATGAGTAAACTTGGTCTGACAGTTACCA
ATGCTTAATCAGTGAGGCACCTATCTCAGCGATCTGTCTATTTCGTTCATCCATAGTTGCCTGACTCCCCGTCGTGTAGA
TAACTACGATACGGGAGGGCTTACCATCTGGCCCCAGTGCTGCAATGATACCGCGAGACCCACGCTCACCGGCTCCAGAT
TTATCAGCAATAAACCAGCCAGCCGGAAGGGCCGAGCGCAGAAGTGGTCCTGCAACTTTATCCGCCTCCATCCAGTCTAT
TAATTGTTGCCGGGAAGCTAGAGTAAGTAGTTCGCCAGTTAATAGTTTGCGCAACGTTGTTGCCATTGCTACAGGCATCG
TGGTGTCACGCTCGTCGTTTGGTATGGCTTCATTCAGCTCCGGTTCCCAACGATCAAGGCGAGTTACATGATCCCCCATG
TTGTGCAAAAAAGCGGTTAGCTCCTTCGGTCCTCCGATCGTTGTCAGAAGTAAGTTGGCCGCAGTGTTATCACTCATGGT
TATGGCAGCACTGCATAATTCTCTTACTGTCATGCCATCCGTAAGATGCTTTTCTGTGACTGGTGAGTACTCAACCAAGT
CATTCTGAGAATAGTGTATGCGGCGACCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGATCTTACCGCTGTTGAGATCCAGTTC
GATGTAACCCACTCGTGCACCCAACTGATCTTCAGCATCTTTTACTTTCACCAGCGTTTCTGGGTGAGCAAAAACAGGAA
GGCAAAATGCCGCAAAAAAGGGAATAAGGGCGACACGGAAATGTTGAATACTCATACTCTTCCTTTTTCAATATTATTGA
AGCATTTATCAGGGTTATTGTCTCATGAGCGGATACATATTTGAATGTATTTAGAAAAATAAACAAATAGGGGTTCCGCG
CACATTTCCCCGAAAAGTGCCACCTGACGTCTAAGAAACCATTATTATCATGACATTAACCTATAAAAATAGGCGTATCA
CGAGGCCCTTTCGTCTCGCGCGTTTCGGTGATGACGGTGAAAACCTCTGACACATGCAGCTCCCGGAGACGGTCACAGCT
TGTCTGTAAGCGGATGCCGGGAGCAGACAAGCCCGTCAGGGCGCGTCAGCGGGTGTTGGCGGGTGTCGGGGCTGGCTTAA
CTATGCGGCATCAGAGCAGATTGTACTGAGAGTGCACCATAAAATTGTAAACGTTAATATTTTGTTAAAATTCGCGTTAA
ATTTTTGTTAAATCAGCTCATTTTTTAACCAATAGGCCGAAATCGGCAAAATCCCTTATAAATCAAAAGAATAGCCCGAG
ATAGGGTTGAGTGTTGTTCCAGTTTGGAACAAGAGTCCACTATTAAAGAACGTGGACTCCAACGTCAAAGGGCGAAAAAC
CGTCTATCAGGGCGATGGCCCACTACGTGAACCATCACCCAAATCAAGTTTTTTGGGGTCGAGGTGCCGTAAAGCACTAA
ATCGGAACCCTAAAGGGAGCCCCCGATTTAGAGCTTGACGGGGAAAGCCGGCGAACGTGGCGAGAAAGGAAGGGAAGAAA
GCGAAAGGAGCGGGCGCTAGGGCGCTGGCAAGTGTAGCGGTCACGCTGCGCGTAACCACCACACCCGCCGCGCTTAATGC
GCCGCTACAGGGCGCGTACTATGGTTGCTTTGACGTATGCGGTGTGAAATACCGCACAGATGCGTAAGGAGAAAATACCG
CATCAGGCGCCATTCGCCATTCAGGCTGCGCAACTGTTGGGAAGGGCGATCGGTGCGGGCCTCTTCGCTATTACGCCAGC
TGGCGAAAGGGGGATGTGCTGCAAGGCGATTAAGTTGGGTAACGCCAGGGTTTTCCCAGTCACGACGTTGTAAAACGACG
GCCAGTGCC FIGURE 7b
(SEQ ID NO:7)
DNA sequence of pKB408:
AAGCTTACTAGTACTTCTCGAGCTCTGTACATGTCCGGTCGCGACGTACGCGTATCGATGGCGCCAGCTGCAGGCGGCCG
CCTGCAGCCACTTGCAGTCCCGTGGAATTCTCACGGTGAATGTAGGCCTTTTGTAGGGTAGGAATTGTCACTCAAGCACC
CCCAACCTCCATTACGCCTCCCCCATAGAGTTCCCAATCAGTGAGTCATGGCACTGTTCTCAAATAGATTGGGGAGAAGT
TGACTTCCGCCCAGAGCTGAAGGTCGCACAACCGCATGATATAGGGTCGGCAACGGCAAAAAAGCACGTGGCTCACCGAA
AAGCAAGATGTTTGCGATCTAACATCCAGGAACCTGGATACATCCATCATCACGCACGACCACTTTGATCTGCTGGTAAA
CTCGTATTCGCCCTAAACCGAAGTGCGTGGTAAATCTACACGTGGGCCCCTTTCGGTATACTGCGTGTGTCTTCTCTAGG
TGCCATTCTTTTCCCTTCCTCTAGTGTTGAATTGTTTGTGTTGGAGTCCGAGCTGTAACTACCTCTGAATCTCTGGAGAA
TGGTGGACTAACGACTACCGTGCACCTGCATCATGTATATAATAGTGATCCTGAGAAGGGGGGTTTGGAGCAATGTGGGA
CTTTGATGGTCATCAAACAAAGAACGAAGACGCCTCTTTTGCAAAGTTTTGTTTCGGCTACGGTGAAGAACTGGATACTT
GTTGTGTCTTCTGTGTATTTTTGTGGCAACAAGAGGCCAGAGACAATCTATTCAAACACCAAGCTTGCTCTTTTGAGCTA
CAAGAACCTGTGGGTATATATCTAGAGTTGTGAAGTCGGTAATCCCGCTGTATAGTAATACGAGTCGCATCTAAATACT
CCGAAGCTGCTGCGAACCCGGAGAATCGAGATGTGCTGGAAAGCTTCTAGCGAGCGGCTAAATTAGCATGAAAGGCTATG
AGAAATTCTGGAGACGGCTTGTTGAATCATGGCGTTCCATTCTTCGACAAGCAAAGCGTTCCGTCGCAGTAGCAGGCACT
CATTCCCGAAAAAACTCGGAGATTCCTAAGTAGCGATGGAACCGGAATAATATAATAGGCAATACATTGAGTTGCCTCGA
CGGTTGCAATGCAGGGGTACTGAGCTTGGACATAACTGTTCCGTACCCCACCTCTTCTCAACCTTTGGCGTTTCCCTGAT
TCAGCGTACCCGTACAAGTCGTAATCACTATTAACCCAGACTGACCGGACGTGTTTTGCCCTTCATTTGGAGAAATAATG
TCATTGCGATGTGTAATTTGCCTGCTTGACCGACTGGGGCTGTTCGAAGCCCGAATGTAGGATTGTTATCCGAACTCTGC
TCGTAGAGGCATGTTGTGAATCTGTGTCGGGCAGGACACGCCTCGAAGGTTCACGGCAAGGGAAACCACCGATAGCAGTG
TCTAGTAGCAACCTGTAAAGCCGCAATGCAGCATCACTGGAAAATACAAACCAATGGCTAAAAGTACATAAGTTAATGCC
TAAAGAAGTCATATACCAGCGGCTAATAATTGTACAATCAAGTGGCTAAACGTACCGTAATTTGCCAACGGCTTGTGGGG
TTGCAGAAGCAACGGCAAAGCCCCACTTCCCCACGTTTGTTTCTTCACTCAGTCCAATCTCAGCTGGTGATCCCCCAATT
GGGTCGCTTGTTTGTTCCGGTGAAGTGAAAGAAGACAGAGGTAAGAATGTCTGACTCGGAGCGTTTTGCATACAACCAAG
GGCAGTGATGGAAGACAGTGAAATGTTGACATTCAAGGAGTATTTAGCCAGGGATGCTTGAGTGTATCGTGTAAGGAGGT
TTGTCTGCCGATACGACGAATACTGTATAGTCACTTCTGATGAAGTGGTCCATATTGAAATGTAAAGTCGGCACTGAACA
GGCAAAAGATTGAGTTGAAACTGCCTAAGATCTCGGGCCCTCGGGCTTCGGCCTTTGGGTGTACATGTTTGTGCTCCGG
GCAAATGCAAAGTGTGGTAGGATCGAACACACTGCTGCCTTTACCAAGCAGCTGAGGGTATGTGATAGGCAAATGTTCAG
GGGCCACTGCATGGTTTCGAATAGAAAGAGAAGCTTAGCCAAGAACAATAGCCGATAAAGATAGCCTCATTAAACGGAAT
GAGCTAGTAGGCAAAGTCAGCGAATGTGTATATATAAAGGTTCGAGGTCCGTGCCTCCCTCATGCTCTCCCCATCTACTC
ATCAACTCAGATCCTCCAGGAGACTTGTACACCATCTTTTGAGGCACAGAAACCCAATAGTCAACCATCACAAGTTTGTA
CAAAAAAGCAGGCTCCGCGGCCGCCCCCTTCACCATGCAGACCTTTGGAGCTTTTCTCGTTTCCTTCCTCGCCGCCAGCG
GCCTGGCCGCGGCCGCTATTGGACCAGTTGCTGATCTGCACATCGTTAACAAGGATTTGGCCCCAGACGGCGTCCAGCGC
CCAACTGTTCTGGCCGGTGGAACTTTTCCGGGCACGCTGATTACCGGTCAAAAGGGCGACAACTTCCAGCTGAACGTGAT
TGATGACCTGACCGACGATCGCATGTTGACCCCTACTTCGATCCATTGGCATGGTTTCTTCCAGAAGGGAACCGCCTGGG
CCGACGGTCCGGCTTTCGTTACACAGTGCCCTATTATCGCAGACAACTCCTTCCTCTACGATTTCGACGTTCCCGACCAG
GCGGGCACCTTCTGGTACCACTCACACTTGTCTACACAGTACTGCGACGGTCTGCGCGGTGCCTTCGTTGTTTACGACCC
CAACGACCCTCACAAGGACCTTTATGATGTCGATGACGGTGGCACAGTTATCACATTGGCTGACTGGTATCACGTCCTCG
CTCAGACCGTTGTCGGAGCTGCTACACCCGACTCTACGCTGATTAACGGCTTGGGACGCAGCCAGACTGGCCCCGCCGAC
GCTGAGCTGGCCGTTATCTCTGTTGAACACAACAAGAGATACCGTTTCAGACTCGTCTCCATCTCGTGCGATCCCAACTT
CACTTTTAGCGTCGACGGTCACAACATGACGGTTATCGAGGTTGATGGCGTGAATACCCGCCCTCTCACCGTCGATTCCA
TTCAAATTTTCGCCGGCCAGCGATACTCCTTTGTGCTGAATGCCAATCAGCCCGAGGATAACTACTGGATCCGCGCTATG
CCTAACATCGGACGAAACACCACTACCCTTGATGGCAAGAATGCCGCTATCCTGCGATACAAGAACGCCAGCGTTGAGGA
GCCCAAAACCGTCGGAGGACCCGCGCAGAGCCCATTGAACGAGGCCGACCTGCGACCTCTGGTGCCCGCTCCTGTCCCTG
GCAACGCAGTTCCTGGTGGTGCGGACATCAACCACCGCCTGAACCTGACATTCAGCAACGGCCTCTTCTCTATCAATAAC
GCATCATTTACAAACCCCAGCGTCCCTGCCTTGTTGCAGATTCTTTCCGGCGCACAAAACGCTCAGGATCTGCTTCCCAC
CGGTTCTTATATCGGCTTGGAGTTGGGCAAGGTCGTTGAACTCGTGATCCCTCCCTTGGCCGTTGGTGGCCCCCATCCAT
TCCACTTGCACGGCCACAACTTTTGGGTCGTCCGAAGCGCTGGTTCTGACGAGTATAATTTCGACGATGCAATTTTGCGC
GACGTGGTCAGCATTGGCGCGGGAACTGACGAGGTTACTATCCGTTTTGTCACTGATAACCCAGGCCCTTGGTTCCTCCA
TTGCCACATCGACTGGCACCTCGAAGCCGGCCTCGCCATTGTTTTCGCCGAAGGCATCAATCAAACCGCAGCCGCCAACC
CGACTCCACAGGCCTGGGACGAACTCTGCCCCAAGTATAACGGACTCTCCGCTTCCCAGAAAGTGAAGCCCAAGAAGGGA
ACAGCCATCTAAAAGGGTGGGCGCGCCGACCCAGCTTTCTTGTACAAAGTGGTGATCGCGCCAGCTCCGTGCGAAAGCCT
GACGCACCGGTAGATTCTTGGTGAGCCCGTATCATGACGGCGGCGGGAGCTACATGGCCCCGGGTGATTTATTTTTTTG
TATCTACTTCTGACCCTTTTCAAATATACGGTCAACTCATCTTTCACTGGAGATGCGGCCTGCTTGGTATTGCGATGTTG Figure 7C
TCAGCTTGGCAAATTGTGGCTTTCGAAAACACAAAACGATTCCTTAGTAGCCATGCATTTTAAGATAACGGAATAGAAGA
AAGAGGAAATTAAAAAAAAAAAAAAAACAAACATCCCGTTCATAACCCGTAGAATCGCCGCTCTTCGTGTATCCCAGTAC
CAGTTTATTTTGAATAGCTCGCCCGCTGGAGAGCATCCTGAATGCAAGTAACAACCGTAGAGGCTGACACGGCAGGTGTT
GCTAGGGAGCGTCGTGTTCTACAAGGCCAGACGTCTTCGCGGTTGATATATATGTATGTTTGACTGCAGGCTGCTCAGCG
ACGACAGTCAAGTTCGCCCTCGCTGCTTGTGCAATAATCGCAGTGGGGAAGCCACACCGTGACTCCCATCTTTCAGTAAA
GCTCTGTTGGTGTTTATCAGCAATACACGTAATTTAAACTCGTTAGCATGGGGCTGATAGCTTAATTACCGTTTACCAGT
GCCATGGTTCTGCAGCTTTCCTTGGCCCGTAAAATTCGGCGAAGCCAGCCAATCACCAGCTAGGCACCAGCTAAACCCTA
TAATTAGTCTCTTATCAACACCATCCGCTCCCCCGGGATCAATGAGGAGAATGAGGGGGATGCGGGGCTAAAGAAGCCTA
CATAACCCTCATGCCAACTCCCAGTTTACACTCGTCGAGCCAACATCCTGACTATAAGCTAACACAGAATGCCTCAATCC
TGGGAAGAACTGGCCGCTGATAAGCGCGCCCGCCTCGCAAAAACCATCCCTGATGAATGGAAAGTCCAGACGCTGCCTGC
GGAAGACAGCGTTATTGATTTCCCAAAGAAATCGGGGATCCTTTCAGAGGCCGAACTGAAGATCACAGAGGCCTCCGCTG
CAGATCTTGTGTCCAAGCTGGCGGCCGGAGAGTTGACCTCGGTGGAAGTTACGCTAGCATTCTGTAAACGGGCAGCAATC
GCCCAGCAGTTAGTAGGGTCCCCTCTACCTCTCAGGGAGATGTAACAACGCCACCTTATGGGACTATCAAGCTGACGCTG
GCTTCTGTGCAGACAAACTGCGCCCACGAGTTCTTCCCTGACGCCGCTCTCGCGCAGGCAAGGGAACTCGATGAATACTA
CGCAAAGCACAAGAGACCCGTTGGTCCACTCCATGGCCTCCCCATCTCTCAAAGACCAGCTTCGAGTCAAGGTACACC
GTTGCCCCTAAGTCGTTAGATGTCCCTTTTTGTCAGCTAACATATGCCACCAGGGCTACGAAACATCAATGGGCTACATC
TCATGGCTAAACAAGTACGACGAAGGGGACTCGGTTCTGACAACCATGCTCCGCAAAGCCGGTGCCGTCTTCTACGTCAA
GACCTCTGTCCCGCAGACCCTGATGGTCTGCGAGACAGTCAACAACATCATCGGGCGCACCGTCAACCCACGCAACAAGA
ACTGGTCGTGCGGCGGCAGTTCTGGTGGTGAGGGTGCGATCGTTGGGATTCGTGGTGGCGTCATCGGTGTAGGAACGGAT
ATCGGTGGCTCGATTCGAGTGCCGGCCGCGTTCAACTTCCTGTACGGTCTAAGGCCGAGTCATGGGCGGCTGCCGTATGC
AAAGATGGCGAACAGCATGGAGGGTCAGGAGACGGTGCACAGCGTTGTCGGGCCGATTACGCACTCTGTTGAGGGTGAGT
CCTTCGCCTCTTCCTTCTTTTCCTGCTCTATACCAGGCCTCCACTGTCCTCCTTTCTTGCTTTTTATACTATATACGAGA
CCGGCAGTCACTGATGAAGTATGTTAGACCTCCGCCTCTTCACCAAATCCGTCCTCGGTCAGGAGCCATGGAAATACGAC
TCCAAGGTCATCCCCATGCCCTGGCGCCAGTCCAGATCGGACATTATTGCCTCCAAGATCAAGAACGGCGGGCTCAATAT
CGGCTACTACAACTTCGACGGCAATGTCCTTCCACACCCTCCTATCCTGCGCGGCGTGGAAACCACCGTCGCCGCACTCG
CCAAAGCCGGTCACACCGTGACCCCGTGGACGCCATACAAGCACGATTTCGGCCACGATCTCATCTCCCATATCTACGCG
GCTGACGGCAGCGCCGACGTAATGCGCGATATCAGTGCATCCGGCGAGCCGGCGATTCCAAATATCAAAGACCTACTGAA
CCCGAACATCAAAGCTGTTAACATGAACGAGCTCTGGGACACGCATCTCCAGAAGTGGAATTACCAGATGGAGTACCTTG
AGAAATGGCGGGAGGCTGAAGAAAAGGCCGGGAAGGAACTGGACGCCATCATCGCGCCGATTACGCCTACCGCTGCGGTA
CGGCATGACCAGTTCCGGTACTATGGGTATGCCTCTGTGATCAACCTGCTGGATTTCACGAGCGTGGTTGTTCCGGTTAC
CTTTGCGGATAAGAACATCGATAAGAAGAATGAGAGTTTCAAGGCGGTTAGTGAGCTTGATGCCCTCGTGCAGGAAGAGT
ATGATCCGGAGGCGTACCATGGGGCACCGGTTGCAGTGCAGGTTATCGGACGGAGACTCAGTGAAGAGAGGACGTTGGCG
ATTGCAGAGGAAGTGGGGAAGTTGCTGGGAAATGTGGTGACTCCATAGCTAATAAGTGTCAGATAGCAATTTGCACAAGA
AATCAATACCAGCAACTGTAAATAAGCGCTGAAGTGACCATGCCATGCTACGAAAGAGCAGAAAAAAAACCTGCCGTAGAA
CCGAAGAGATATGACACGCTTCCATCTCTCAAAGGAAGAATCCCTTCAGGGTTGCGTTTCCAGTCTAGACACGTATAACG
GCACAAGTGTCTCTCACCAAATGGGTTATATCTCAAATGTGATCTAAGGATGGAAAGCCCAGAATATCGATCGCGCGCAG
ATCCCATATATAGGGCCCGGGTTATAATTACCTCAGGTCGACGTCCCATGGCCATTCGAATTCGTAATCATGGTCATAGCT
GTTTCCTGTGTGAAATTGTTATCCGCTCACAATTCCACACAACATACGAGCCGGAAGCATAAAGTGTAAAGCCTGGGGTG
CCTAATGAGTGAGCTAACTCACATTAATTGCGTTGCGCTCACTGCCCGCTTTCCAGTCGGGAAACCTGTCGTGCCAGCTG
CATTAATGAATCGGCCAACGCGCGGGGAGAGGCGGTTTGCGTATTGGGCGCTCTTCCGCTTCCTCGCTCACTGACTCGCT
GCGCTCGGTCGTTCGGCTGCGGCGAGCGGTATCAGCTCACTCAAAGGCGGTAATACGGTTATCCACAGAATCAGGGGATA
ACGCAGGAAAGAACATGTGAGCAAAAGGCCAGCAAAAGGCCAGGAACCGTAAAAAGGCCGCGTTGCTGGCGTTTTTCCAT
AGGCTCCGCCCCCTGACGAGCATCACAAAAATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCCTGCCGCTTACCGGATACCTGTCCGCCTTTC
TCCCTTCGGGAAGCGTGGCGCTTTCTCATAGCTCACGCTGTAGGTATCTCAGTTCGGTGTAGGTCGTTCGCTCCAAGCTG
GGCTGTGTGCACGAACCCCCCGTTCAGCCCGACCGCTGCGCCTTATCCGGTAACTATCGTCTTGAGTCCAACCCGGTAAG
ACACGACTTATCGCCACTGGCAGCAGCCACTGGTAACAGGATTAGCAGAGCGAGGTATGTAGGCGGTGCTACAGAGTTCT
TGAAGTGGTGGCCTAACTACGGCTACACTAGAAGAACAGTATTTGGTATCTGCGCTCTGCTGAAGCCAGTTACCTTCGGA
AAAAGAGTTGGTAGCTCTTGATCCGGCAAACAAACCACCGCTGGTAGCGGTGGTTTTTTTGTTTGCAAGCAGCAGATTAC
GCGCAGAAAAAAAGGATCTCAAGAAGATCCTTTGATCTTTTCTACGGGGTCTGACGCTCAGTGGAACGAAAACTCACGTT
AAGGGATTTTGGTCATGAGATTATCAAAAAGGATCTTCACCTAGATCCTTTTAAATTAAAAATGAAGTTTTAAATCAATC
TAAAGTATATATGAGTAAACTTGGTCTGACAGTTACCAATGCTTAATCAGTGAGGCACCTATCTCAGCGATCTGTCTATT
TCGTTCATCCATAGTTGCCTGACTCCCCGTCGTGTAGATAACTACGATACGGGAGGGCTTACCATCTGGCCCCAGTGCTG
CAATGATACCGCGAGACCCACGCTCACCGGCTCCAGATTTATCAGCAATAAACCAGCCAGCCGGAAGGGCCGAGCGCAGA
AGTGGTCCTGCAACTTTATCCGCCTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTTGGTATGGCTTCATTCAGCTCCG
GTTCCCAACGATCAAGGCGAGTTACATGATCCCCCATGTTGTGCAAAAAAGCGGTTAGCTCCTTCGGTCCTCCGATCGTT Figure 7D
GTCAGAAGTAAGTTGGCCGCAGTGTTATCACTCATGGTTATGGCAGCACTGCATAATTCTCTTACTGTCATGCCATCCGT
AAGATGCTTTTCTGTGACTGGTGAGTACTCAACCAAGTCATTCTGAGAATAGTGTATGCGGCGACCGAGTTGCTCTTGCC
CGGCGTCAATACGGGATAATACCGCGCCACATAGCAGAACTTTAAAAGTGCTCATCATTGGAAAACGTTCTTCGGGGCGA
AAACTCTCAAGGATCTTACCGCTGTTGAGATCCAGTTCGATGTAACCCACTCGTGCACCCAACTGATCTTCAGCATCTTT
TACTTTCACCAGCGTTTCTGGGTGAGCAAAAACAGGAAGGCAAAATGCCGCAAAAAAGGGAATAAGGGCGACACGGAAAT
GTTGAATACTCATACTCTTCCTTTTTCAATATTATTGAAGCATTTATCAGGGTTATTGTCTCATGAGCGGATACATATTT
GAATGTATTTAGAAAAATAAACAAATAGGGGTTCCGCGCACATTTCCCCGAAAAGTGCCACCTGACGTCTAAGAAACCAT
TATTATCATGACATTAACCTATAAAAATAGGCGTATCACGAGGCCCTTTCGTCTCGCGCGTTTCGGTGATGACGGTGAAA
ACCTCTGACACATGCAGCTCCCGGAGACGGTCACAGCTTGTCTGTAAGCGGATGCCGGGAGCAGACAAGCCCGTCAGGGC
GCGTCAGCGGGTGTTGGCGGGTGTCGGGGCTGGCTTAACTATGCGGCATCAGAGCAGATTGTACTGAGAGTGCACCATAA
AATTGTAAACGTTAATATTTTGTTAAAATTCGCGTTAAATTTTTGTTAAATCAGCTCATTTTTTAACCAATAGGCCGAAA
TCGGCAAAATCCCTTATAAATCAAAAGAATAGCCCGAGATAGGGTTGAGTGTTGTTCCAGTTTGGAACAAGAGTCCACTA
TTAAAGAACGTGGACTCCAACGTCAAAGGGCGAAAAACCGTCTATCAGGGCGATGGCCCACTACGTGAACCATCACCCAA
ATCAAGTTTTTGGGGTCGAGGTGCCGTAAAGCACTAAATCGGAACCCTAAAGGGAGCCCCCGATTTAGAGCTTGACGGG
GAAAGCCGGCGAACGTGGCGAGAAAGGAAGGGAAGAAAGCGAAAGGAGCGGGCGCTAGGGCGCTGGCAAGTGTAGCGGTC
ACGCTGCGCGTAACCACCACACCCGCCGCGCTTAATGCGCCGCTACAGGGCGCGTACTATGGTTGCTTTGACGTATGCGG
TGTGAAATACCGCACAGATGCGTAAGGAGAAAATACCGCATCAGGCGCCATTCGCCATTCAGGCTGCGCAACTGTTGGGA
AGGGCGATCGGTGCGGGCCTCTTCGCTATTACGCCAGCTGGCGAAAGGGGGATGTGCTGCAAGGCGATTAAGTTGGGTAA
CGCCAGGGTTTTCCCAGTCACGACGTTGTAAAACGACGGCCAGTGCCC FIGURE 8b
(SEQ ID NO:8)
DNA sequence of pKB410:
AAGCTTACTAGTACTTCTCGAGCTCTGTACATGTCCGGTCGCGACGTACGCGTATCGATGGCGCCAGCTGCAGGCGGCCG
CCTGCAGCCACTTGCAGTCCCGTGGAATTCTCACGGTGAATGTAGGCCTTTTGTAGGGTAGGAATTGTCACTCAAGCACC
CCCAACCTCCATTACGCCTCCCCCATAGAGTTCCCAATCAGTGAGTCATGGCACTGTTCTCAAATAGATTGGGGAGAAGT
TGACTTCCGCCCAGAGCTGAAGGTCGCACAACCGCATGATATAGGGTCGGCAACGGCAAAAAAGCACGTGGCTCACCGAA
AAGCAAGATGTTTGCGATCTAACATCCAGGAACCTGGATACATCCATCATCACGCACGACCACTTTGATCTGCTGGTAAA
CTCGTATTCGCCCTAAACCGAAGTGCGTGGTAAATCTACACGTGGGCCCCTTTCGGTATACTGCGTGTGTCTTCTCTAGG
TGCCATTCTTTTCCCTTCCTCTAGTGTTGAATTGTTTGTGTTGGAGTCCGAGCTGTAACTACCTCTGAATCTCTGGAGAA
TGGTGGACTAACGACTACCGTGCACCTGCATCATGTATATAATAGTGATCCTGAGAAGGGGGGTTTGGAGCAATGTGGGA
CTTTGATGGTCATCAAACAAAGAACGAAGACGCCTCTTTTGCAAAGTTTTGTTTCGGCTACGGTGAAGAACTGGATACTT
GTTGTGTCTTCTGTGTATTTTTGTGGCAACAAGAGGCCAGAGACAATCTATTCAAACACCAAGCTTGCTCTTTTGAGCTA
CAAGAACCTGTGGGTATATATCTAGAGTTGTGAAGTCGGTAATCCCGCTGTATAGTAATACGAGTCGCATCTAAATACT
CCGAAGCTGCTGCGAACCCGGAGAATCGAGATGTGCTGGAAAGCTTCTAGCGAGCGGCTAAATTAGCATGAAAGGCTATG
AGAAATTCTGGAGACGGCTTGTTGAATCATGGCGTTCCATTCTTCGACAAGCAAAGCGTTCCGTCGCAGTAGCAGGCACT
CATTCCCGAAAAAACTCGGAGATTCCTAAGTAGCGATGGAACCGGAATAATATAATAGGCAATACATTGAGTTGCCTCGA
CGGTTGCAATGCAGGGGTACTGAGCTTGGACATAACTGTTCCGTACCCCACCTCTTCTCAACCTTTGGCGTTTCCCTGAT
TCAGCGTACCCGTACAAGTCGTAATCACTATTAACCCAGACTGACCGGACGTGTTTTGCCCTTCATTTGGAGAAATAATG
TCATTGCGATGTGTAATTTGCCTGCTTGACCGACTGGGGCTGTTCGAAGCCCGAATGTAGGATTGTTATCCGAACTCTGC
TCGTAGAGGCATGTTGTGAATCTGTGTCGGGCAGGACACGCCTCGAAGGTTCACGGCAAGGGAAACCACCGATAGCAGTG
TCTAGTAGCAACCTGTAAAGCCGCAATGCAGCATCACTGGAAAATACAAACCAATGGCTAAAAGTACATAAGTTAATGCC
TAAAGAAGTCATATACCAGCGGCTAATAATTGTACAATCAAGTGGCTAAACGTACCGTAATTTGCCAACGGCTTGTGGGG
TTGCAGAAGCAACGGCAAAGCCCCACTTCCCCACGTTTGTTTCTTCACTCAGTCCAATCTCAGCTGGTGATCCCCCAATT
GGGTCGCTTGTTTGTTCCGGTGAAGTGAAAGAAGACAGAGGTAAGAATGTCTGACTCGGAGCGTTTTGCATACAACCAAG
GGCAGTGATGGAAGACAGTGAAATGTTGACATTCAAGGAGTATTTAGCCAGGGATGCTTGAGTGTATCGTGTAAGGAGGT
TTGTCTGCCGATACGACGAATACTGTATAGTCACTTCTGATGAAGTGGTCCATATTGAAATGTAAAGTCGGCACTGAACA
GGCAAAAGATTGAGTTGAAACTGCCTAAGATCTCGGGCCCTCGGGCCTTCGGCCTTTGGGTGTACATGTTTGTGCTCCGG
GCAAATGCAAAGTGTGGTAGGATCGAACACACTGCTGCCTTTACCAAGCAGCTGAGGGTATGTGATAGGCAAATGTTCAG
GGGCCACTGCATGGTTTCGAATAGAAAGAGAAGCTTAGCCAAGAACAATAGCCGATAAAGATAGCCTCATTAAACGGAAT
GAGCTAGTAGGCAAAGTCAGCGAATGTGTATATATAAAGGTTCGAGGTCCGTGCCTCCCTCATGCTCTCCCCATCTACTC
ATCAACTCAGATCCTCCAGGAGACTTGTACACCATCTTTTGAGGCACAGAAACCCAATAGTCAACCATCACAAGTTTGTA
CAAAAAAGCAGGCTCCGCGGCCGCCCCCTTCACCATGTATCGGAAGTTGGCCGTCATCTCGGCCTTCTTGGCCACAGCTC
GTGCTGCTATTGGACCAGTTGCTGATCTGCACATCGTTAACAAGGATTTGGCCCCAGACGGCGTCCAGCGCCCAACTGTT
CTGGCCGGTGGAACTTTTCCGGGCACGCTGATTACCGGTCAAAAGGGCGACAACTTCCAGCTGAACGTGATTGATGACCT
GACCGACGATCGCATGTTGACCCCTACTTCGATCCATTGGCATGGTTTCTTCCAGAAGGGAACCGCCTGGGCCGACGGTC
CGGCTTTCGTTACACAGTGCCCTATTATCGCAGACAACTCCTTCCTCTACGATTTCGACGTTCCCGACCAGGCGGGCACC
TTCTGGTACCACTCACACTTGTCTACACAGTACTGCGACGGTCTGCGCGGTGCCTTCGTTGTTTACGACCCCAACGACCC
TCACAAGGACCTTTATGATGTCGATGACGGTGGCACAGTTATCACATTGGCTGACTGGTATCACGTCCTCGCTCAGACCG
TTGTCGGAGCTGCTACACCCGACTCTACGCTGATTAACGGCTTGGGACGCAGCCAGATGGCCCCGCCGACGCTGAGCTG
GCCGTTATCTCTGTTGAACACAACAAGAGATACCGTTTCAGACTCGTCTCCATCTCGTCGGATCCCAACTTCACTTTTAG
CGTCGACGGTCACAACATGACGGTTATCGAGGTTGATGGCGTGAATACCCGCCCTCTCACCGTCGATTCCATTCAAATTT
TCGCCGGCCAGCGATACTCCTTTGTGCTGAATGCCAATCAGCCCGAGGATAACTACTGGATCCGCGCTATGCCTAACATC
GGACGAAACACCACTACCCTTGATGGCAAGAATGCCGCTATCCTGCGATACAAGAACGCCAGCGTTGAGGAGCCCAAAAC
CGTCGGAGGACCCGCGCAGAGCCCATTGAACGAGGCCGACCTGCGACCTCTGGTGCCCGCTCCTGTCCCTGGCAACGCAG
TTCCTGGTGGTGCGGACATCAACCACCGCCTGAACCTGACATTCAGCAACGGCCTCTTCTATCAATAACGCATCATTT
ACAAACCCCAGCGTCCCTGCCTTGTTGCAGATTCTTTCCGGCGCACAAAACGCTCAGGATCTGCTTCCCACCGGTTCTTA
TATCGGCTTGGAGTTGGGCAAGGTCGTTGAACTCGTGATCCCTCCCTTGGCCGTTGGTGGCCCCCATCCATTCCACTTGC
ACGGGCCACAACTTTTGGGTCGTCCGAAGCGCTGGTTCTGACGAGTATAATTTCGACGATGCAATTTTGCGCGACGTGGTC
AGCATTGGCGCGGGAACTGACGAGGTTACTATCCGTTTTGTCACTGATAACCCAGGCCCTTGGTTCCTCCATTGCCACAT
CGACTGGCACCTCGAAGCGGCCTCGCCATTGTTTTCGCCGAAGGCATCAATCAAACCGCAGCCGCCAACCCGACTCCAC
AGGCCTGGGACGAACTCTGCCCCAAGTATAACGGACTCTCCGCTTCCCAGAAAGTGAAGCCCAAGAAGGGAACAGCCATC
TAAAAGGGTGGGCGCGCCGACCCAGCTTTCTTGTACAAAGTGGTGATCGCGCCAGCTCCGTGCGAAAGCCTGACGCACCG
GTAGATTCTTGGTGAGCCCGTATCATGACGGCGGCGGGAGCTACATGCCCCGGGTGATTTATTTTTTTGTATCTACTT
CTGACCCTTTTCAAATATACGGTCAACTCATCTTTCACTGGAGATGCGGCCTGCTTGGTATTGCGATGTTGTCAGCTTGG
CAAATTGTGGCTTTCGAAAACACAAAACGATTCCTTAGTAGCCATGCATTTTAAGATAACGGAATAGAAGAAAGAGGAAA Figure 8C
TTAAAAAAAAAAAAAAAACAAACATCCCGTTCATAACCCGTAGAATCGCCGCTCTTCGTGTATCCCAGTACCAGTTTATT
TTGAATAGCTCGCCCGCTGGAGAGCATCCTGAATGCAAGTAACAACCGTAGAGGCTGACACGGCAGGTGTTGCTAGGGAG
CGTCGTGTTCTACAAGGCCAGACGTCTTCGCGGTTGATATATATGTATGTTTGACTGCAGGCTGCTCAGCGACGACAGTC
AAGTTCGCCCTCGCTGCTTGTGCAATAATCGCAGTGGGGAAGCCACACCGTGACTCCCATCTTTCAGTAAAGCTCTGTTG
GTGTTTATCAGCAATACACGTAATTTAAACTCGTTAGCATGGGGCTGATAGCTTAATTACCGTTTACCAGTGCCATGGTT
CTGCAGCTTTCCTTGGCCCGTAAAATTCGGCGAAGCCAGCCAATCACCAGCTAGGCACCAGCTAAACCCTATAATTAGTC
TCTTATCAACACCATCCGCTCCCCCGGGATCAATGAGGAGAATGAGGGGGATGCGGGGCTAAAGAAGCCTACATAACCCT
CATGCCAACTCCCAGTTTACACTCGTCGAGCCAACATCCTGACTATAAGCTAACACAGAATGCCTCAATCCTGGGAAGAA
CTGGCCGCTGATAAGCGCGCCCGCCTCGCAAAACCATCCCTGATGAATGGAAAGTCCAGACGCTGCCTGCGGAAGACAG
CGTTATTGATTTCCCAAAGAAATCGGGGATCCTTTCAGAGGCCGAACTGAAGATCACAGAGGCCTCCGCTGCAGATCTTG
TGTCCAAGCTGGCGGCCGGAGAGTTGACCTCGGTGGAAGTTACGCTAGCATTCTGTAAACGGGCAGCAATCGCCCAGCAG
TTAGTAGGGTCCCCTCTACCTCTCAGGGAGATGTAACAACGCCACCTTATGGGACTATCAAGCTGACGCTGGCTTCTGTG
CAGACAAACTGCGCCCACGAGTTCTTCCCTGACGCCGCTCTCGCGCAGGCAAGGGAACTCGATGAATACTACGCAAAGCA
CAAGAGACCCGTTGGTCCACTCCATGGCCTCCCCATCTCTCTCAAAGACCAGCTTCGAGTCAAGGTACACCGTTGCCCCT
AAGTCGTTAGATGTCCCTTTTTGTCAGCTAACATATGCCACCAGGGCTACGAAACATCAATGGGCTACATCTCATGGCTA
AACAAGTACGACGAAGGGGACTCGGTTCTGACAACCATGCTCCGCAAAGCCGGTGCCGTCTTCTACGTCAAGACCTCTGT
CCCGCAGACCCTGATGGTCTGCGAGACAGTCAACAACATCATCGGGCGCACCGTCAACCCACGCAACAAGAACTGGTCGT
GCGGCGGCAGTTCTGGTGGTGAGGGTGCGATCGTTGGGATTCGTGGTGGCGTCATCGGTGTAGGAACGGATATCGGTGGC
TCGATTCGAGTGCCGGCCGCGTTCAACTTCCTGTACGGTCTAAGGCCGAGTCATGGGCGGCTGCCGTATGCAAAGATGGC
GAACAGCATGGAGGGTCAGGAGACGGTGCACAGCGTTGTCGGGCCGATTACGCACTCTGTTGAGGGTGAGTCCTTCGCCT
CTTCCTTCTTTTCCTGCTCTATACCAGGCCTCCACTGTCCTCCTTTCTTGCTTTTTATACTATATACGAGACCGGCAGTC
ACTGATGAAGTATGTTAGACCTCCGCCTCTTCACCAAATCCGTCCTCGGTCAGGAGCCATGGAAATACGACTCCAAGGTC
ATCCCCATGCCCTGGCGCCAGTCCGAGTCGGACATTATTGCCTCCAAGATCAAGAACGGCGGGCTCAATATCGGCTACTA
CAACTTCGACGGCAATGTCCTTCCACACCCTCCTATCCTGCGCGGCGTGGAAACCACCGTCGCCGCACTCGCCAAAGCCG
GTCACACCGTGACCCCGTGGACGCCATACAAGCACGATTTCGGCCACGATCTCATCTCCCATATCTACGCGGCTGACGGC
AGCGCCGACGTAATGCGCGATATCAGTGCATCCGGCGAGCCGGCGATTCCAAATATCAAAGACCTACTGAACCCGAACAT
CAAAGCTGTTAACATGAACGAGCTCTGGGACACGCATCTCCAGAAGTGGAATTACCAGATGGAGTACCTTGAGAAATGGC
GGGAGGCTGAAGAAAAGGCCGGGAAGGAACTGGACGCCATCATCGCGCCGATTACGCCTACCGCTGCGGTACGGCATGAC
CAGTTCCGGTACTATGGGTATGCCTCTGTGATCAACCTGCTGGATTTCACGAGCGTGGTTGTTCCGGTTACCTTTGCGGA
TAAGAACATCGATAAGAAGAATGAGAGTTTCAAGGCGGTTAGTGAGCTTGATGCCCTCGTGCAGGAAGAGTATGATCCGG
AGGCGTACCATGGGGCACCGGTTGCAGTGCAGGTTATCGGACGGAGACTCAGTGAAGAGAGGACGTTGGCGATTGCAGAG
GAAGTGGGGAAGTTGCTGGGAAATGTGGTGACTCCATAGCTAATAAGTGTCAGATAGCAATTTGCACAAGAAATCAATAC
CAGCAACTGTAAATAAGCGCTGAAGTGACCATGCCATGCTACGAAAGAGCAGAAAAAAACCTGCCGTAGAACCGAAGAGA
TATGACACGCTTCCATCTCTCAAAGGAAGAATCCCTTCAGGGTTGCGTTTCCAGTCTAGACACGTATAACGGCACAAGTG
TCTCTCACCAAATGGGTTATATCTCAAATGTGATCTAAGGATGGAAAGCCCAGAATATCGATCGCGCGCAGATCCATATA
TAGGGCCCGGGTTATAATTACCTCAGGTCGACGTCCCATGGCCATTCGAATTCGTAATCATGGTCATAGCTGTTTCCTGT
GTGAAATTGTTATCCGCTCACAATTCCACACAACATACGAGCCGGAAGCATAAAGTGTAAAGCCTGGGGTGCCTAATGAG
TGAGCTAACTCACATTAATTGCGTTGCGCTCACTGCCCGCTTTCCAGTCGGGAAACCTGTCGTGCCAGCTGCATTAATGA
ATCGGCCAACGCGCGGGGAGAGGCGGTTTGCGTATTGGGCGCTCTTCCGCTTCCTCGCTCACTGACTCGCTGCGCTCGGT
CGTTCGGCTGCGGCGAGCGGTATCAGCTCACTCAAAGGCGGTAATACGGTTATCCACAGAATCAGGGGATAACGCAGGAA
AGAACATGTGAGCAAAAGGCCAGCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTACCGGATACCTGTCCGCCTTTCTCCCTTCGG
GAAGCGTGGCGCTTTCTCATAGCTCACGCTGTAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATCGTCTTGAGTCCAACCCGGTAAGACACGACTT
ATCGCCACTGGCAGCAGCCACTGGTAACAGGATTAGCAGAGCGAGGTATGTAGGCGGTGCTACAGAGTTCTTGAAGTGGT
GGCCTAACTACGGCTACACTAGAAGAACATATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGTGGAACGAAAACTCACGTTAAGGGATTT
TGGTCATGAGATTATCAAAAAGGATCTTCACCTAGATCCTTTTAAATTAAAAATGAAGTTTTAAATCAATCTAAAGTATA
TATGAGTAAACTTGGTCTGACAGTTACCAATGCTTAATCAGTGAGGCACCTATCTCAGCGATCTGTCTATTTCGTTCATC
CATAGTTGCCTGACTCCCCGTCGTGTAGATAACTACGATACGGGAGGGCTTACCATCTGGCCCCAGTGCTGCAATGATAC
CGCGAGACCCACGCTCACCGGCTCCAGATTTATCAGCAATAAACCAGCCAGCCGGAAGGGCCGAGCGCAGAAGTGGTCCT
GCAACTTTATCCGCCTCCATCCAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGCTCCTTCGGTCCTCCGATCGTTGTCAGAAGT
AAGTTGGCCGCAGTGTTATCACTCATGGTTATGGCAGCACTGCATAATTCTCTTACTGTCATGCCATCCGTAAGATGCTT Figure 8D
TTCTGTGACTGGTGAGTACTCAACCAAGTCATTCTGAGAATAGTGTATGCGGCGACCGAGTTGCTCTTGCCCGGCGTCAA
TACGGGATAATACCGCGCCACATAGCAGAACTTTAAAAGTGCTCATCATTGGAAAACGTTCTTCGGGGCGAAAACTCTCA
AGGATCTTACCGCTGTTGAGATCCAGTTCGATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGGGAATAAGGGCGACACGGAAATGTTGAATAC
TCATACTCTTCCTTTTTCAATATTATTGAAGCATTTATCAGGGTTATTGTCTCATGAGCGGATACATATTTGAATGTATT
TAGAAAAATAAACAAATAGGGGTTCCGCGCACATTTCCCCGAAAAGTGCCACCTGACGTCTAAGAAACCATTATTATCAT
GACATTAACCTATAAAAATAGGCGTATCACGAGGCCCTTTCGTCTCGCGCGTTTCGGTGATGACGGTGAAAACCTCTGAC
ACATGCAGCTCCCGGAGACGGTCACAGCTTGTCTGTAAGCGGATGCCGGGAGCAGACAAGCCCGTCAGGGCGCGTCAGCG
GGTGTTGGCGGGTGTCGGGGCTGGCTTAACTATGCGGCATCAGAGCAGATTGTACTGAGAGTGCACCATAAAATTGTAAA
CGTTAATATTTTGTTAAAATTCGCGTTAAATTTTTGTTAAATCAGCTCATTTTTTAACCAATAGGCCGAAATCGGCAAAA
TCCCTTATAAATCAAAAGAATAGCCCGAGATAGGGTTGAGTGTTGTTCCAGTTTGGAACAAGAGTCCACTATTAAAGAAC
GTGGACTCCAACGTCAAAGGGCGAAAAACCGTCTATCAGGGCGATGGCCCACTACGTGAACCATCACCCAAATCAAGTTT
TTTGGGGTCGAGGTGCCGTAAAGCACTAAATCGGAACCCTAAAGGGAGCCCCCGATTTAGAGCTTGACGGGGAAAGCCGG
CGAACGTGGCGAGAAAGGAAGGGAAGAAAGCGAAAGGAGCGGGCGCTAGGGCGCTGGCAAGTGTAGCGGTCACGCTGCGC
GTAACCACCACACCCGCCGCGCTTAATGCGCCGCTACAGGGCGCGTACTATGGTTGCTTTGACGTATGCGGTGTGAAATA
CCGCACAGATGCGTAAGGAGAAAATACCGCATCAGGCGCCATTCGCCATTCAGGCTGCGCAACTGTTGGGAAGGGCGATC
GGTGCGGGCCTCTTCGCTATTACGCCAGCTGGCGAAAGGGGGATGTGCTGCAAGGCGATTAAGTTGGGTAACGCCAGGGT
TTTCCCAGTCACGACGTTGTAAAACGACGGCCAGTGCCC

US 8,093,016 B2

USE OF AN ASPARTIC PROTEASE (NS24) SIGNAL SEQUENCE FOR HETEROLOGOUS PROTEIN EXPRESSION

This application is a 371 of PCT/US08/06498, filed May 21, 2008 which claims priority to provisional applications 60/931,072, filed May 21, 2007 and 60/984,430 filed Nov. 1, 2007, respectively.

FIELD OF THE INVENTION

The invention relates to heterologous polypeptide expression and secretion by filamentous fungi and vectors and processes for expression and secretion of such polypeptides. More particularly, the invention discloses the use of a signal sequence form an aspartic protease obtained from *Trichoderma* and referred to as an NSP24 signal sequence.

SEQUENCE LISTING

The sequence listing submitted on Sep. 30, 2010, via EFS-Web, in compliance with 37 C.F.R. 1.52(e)(2), is incorporated herein by reference. The sequence listing text file submitted via EFS-Web contains the file "30979WO-seqlist.txt", created on Sep. 30, 2010, which is 52,972 bytes in size.

BACKGROUND OF THE INVENTION

Host cells such as yeast, filamentous fungi and bacteria have been used to express and secrete proteins that are foreign or heterologous to the hosts. Production of these foreign or heterologous proteins in yeast, filamentous fungi and bacteria involves the expression and partial or complete purification from the host cell. Purification can be greatly simplified if the heterologous proteins are secreted from the cell into the media.

Proteins that are secreted from the cell possess a signal peptide sequence. In the cell, the signal peptide sequence functions to direct a protein into the endoplasmic reticulum (ER). Movement into the lumen of the ER represents the initial step into the secretory pathway of the host cell. Thus, the addition of a signal peptide sequence to a non-secretory protein could promote secretion of that protein.

A number of industrial enzymes (e.g., proteases, amylases, glucoamylases, cellulases, xylanase and phytases) which are produced either endogenously or exogenously in a host cell are secreted into the medium.

Methods for expression of heterologous proteins and their secretion in a biologically active mature form using host cells such as yeast, filamentous fungi and bacteria as the expression system are needed.

SUMMARY OF THE INVENTION

The invention relates to heterologous polypeptide expression and secretion by filamentous fungi and vectors and processes for expression and secretion of such polypeptides. More particularly, the invention discloses the use of a signal sequence form an aspartic protease obtained from *Trichoderma* and referred to as an NSP24 signal sequence.

Some aspects of the invention comprise fusion proteins comprising an isolated signal peptide comprising SEQ ID NO:4 or a variant thereof operably linked to a heterologous protein. In some embodiments, the heterologous protein is chosen from: a phytase, a glucoamylase, an alpha amylase, a granular starch hydrolyzing enzyme, a cellulase, a lipase, a xylanase, a cutinase, a hemicellulase, a protease, an oxidase, a laccase and combinations thereof. In some embodiments, the heterologous protein is a phytase and the phytase has at least 90% sequence identity to SEQ ID NO:5. Further aspects of the invention are an isolated polynucleotide comprising a polynucleotide encoding the fusion protein. Further aspects of the invention are expression vectors comprising the polynucleotide encoding the fusion protein. The expression vectors can also comprise a promoter. Other aspects of the invention are host cells comprising the expression vector. The host cells can be fungal or bacterial cells. In some embodiments, the host cell is a bacterial cell such as a *Streptomyces* or *Bacillus* cell. In some embodiments, the host cell is a fungal cell such as a filamentous fungal cell. (e.g., an *Aspergillus* spp. a *Fusarium* spp. or *Trichoderma* spp.). In some embodiments, the *Aspergillus* is *A. niger, A. oryzae, A. nidulans*, or *A. awamori*. In some embodiments, the *Trichoderma* is *T. reesei*.

Other aspects of the invention are methods of producing heterologous proteins in a host cell, comprising: producing the expression vector comprising a fusion protein comprising an isolated signal peptide comprising SEQ ID NO:4 or a variant thereof operably linked to a heterologous protein; transforming a host cell with the expression vector; and culturing the host cell, wherein the heterologous protein is secreted from the host cell. In some embodiments, the host cell is a filamentous fungal host cell. In some embodiments, the filamentous fungal host cell is a *Trichoderma* or *Aspergillus* cell.

Other aspects of the invention are methods for producing a heterologous protein in a host cell, comprising introducing into a host cell a polynucleotide encoding a signal peptide comprising SEQ ID NO:4 or a variant thereof operably linked to a heterologous protein, culturing the host cell under suitable culture conditions for the expression and production of the heterologous protein, and producing said heterologous protein. In some embodiments, the method also includes recovering the produced heterologous protein. In some embodiments, the host cell is a fungal or bacterial cell. The fungal host cell can be a filamentous fungal cell. The bacterial host cell can be a *Streptomyces* sp. or a *Bacillus* sp. In some embodiments, the heterologous protein is chosen from a phytase, a glucoamylase, an alpha amylase, a granular starch hydrolyzing enzyme, a cellulase, a lipase, a xylanase, a cutinase, a hemicellulase, a protease, an oxidase, a laccase and combinations thereof.

Further aspects of the invention are a DNA construct for use in transforming a filamentous fungal cell to enable secretion of a protein of interest, the DNA construct comprising a promoter from a fungal gene operably linked to a polynucleotide encoding a signal peptide and a protein of interest wherein said signal peptide has the sequence of SEQ ID NO:4 and said protein of interest is chosen from a phytase, a glucoamylase, an alpha amylase, a granular starch hydrolyzing enzyme, a cellulase, a lipase, a xylanase, a cutinase, a hemicellulase, a protease, an oxidase, a laccase and combinations thereof. In some embodiments, the protein of interest is a phytase and the phytase has at least 90% sequence identity to SEQ ID NO:5.

BRIEF DESCRIPTION OF THE DRAWINGS

FIGS. 1*a* and *b* illustrate the NSP24 nucleotide sequence (SEQ ID NO: 1) (FIG. 1*a*) and the mature protein sequence (SEQ ID NO:2) (FIG. 1*b*).

FIGS. 4a and b illustrate the structure of the expression vector pTrex3g(BP17NSP) and the polynucleotide sequence of *Buttiauxella* phytase BP-17. FIG. 4a is a schematic of the expression vector and FIG. 4b is the mature protein sequence of BP-17 (SEQ ID NO:5).

FIGS. 6a-d show the schematic and the polynucleotide sequence of the *Trichoderma* expression plasmid pTrex4-laccaseD opt. FIG. 6a is a schematic of the expression plasmid and FIGS. 6b-d are the sequence (SEQ ID NO:6).

FIGS. 7a-d show the schematic and the polynucleotide sequence of the *Trichoderma* expression plasmid pKB408. FIG. 7a is a schematic of the expression plasmid and FIGS. 7b-d are the sequence (SEQ ID NO:7).

FIGS. 8a-d show the schematic and the polynucleotide sequence of the *Trichoderma* expression plasmid pKB410. FIG. 8a is a schematic of the expression plasmid and FIGS. 8b-d are the sequence (SEQ ID NO:8).

DETAILED DESCRIPTION OF THE INVENTION

Figure 2:
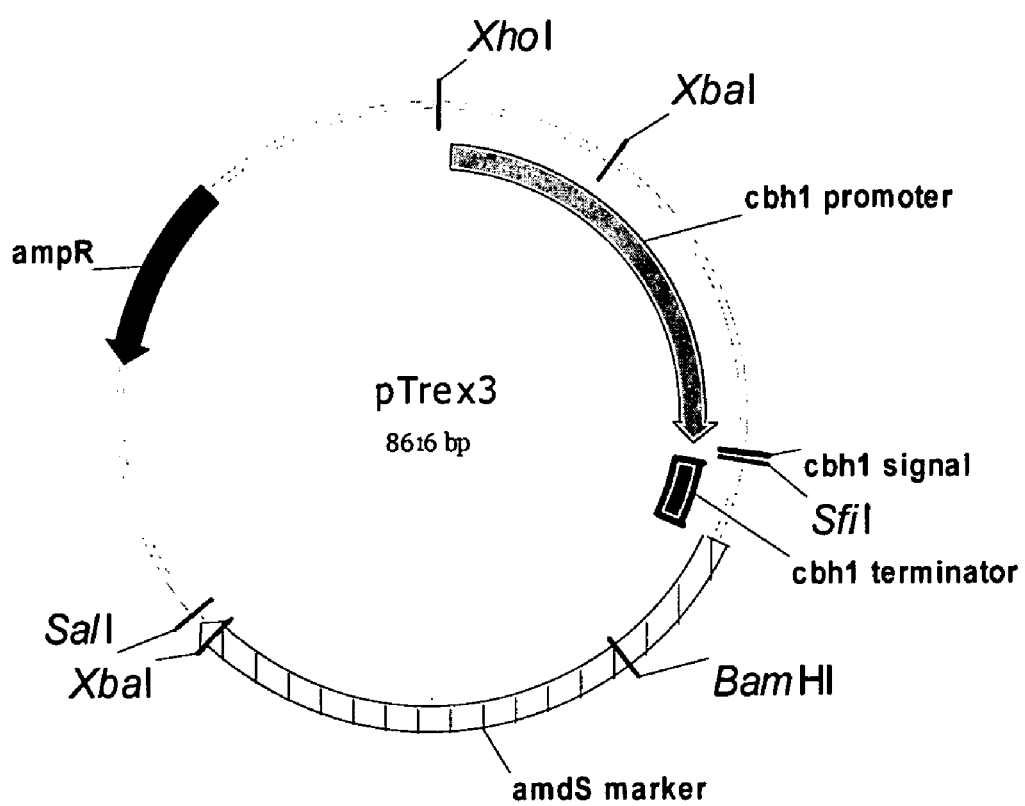
FIG. 2 illustrates the structure of the expression vector pTrex3g used to transform *Trichoderma reesei* spores.

The invention relates to heterologous polypeptide expression and secretion by filamentous fungi and vectors and processes for expression and secretion of such polypeptides. More particularly, the invention discloses the use of a signal sequence form an aspartic protease obtained from *Trichoderma* and referred to as an NSP24 signal sequence.

The invention will now be described in detail by way of reference only using the following definitions and examples. All patents and publications, including all sequences disclosed within such patents and publications, referred to herein are expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); Ausubel et al., Eds *Short Protocols in Molecular Biology* (5$^{th}$ Ed. 2002); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims. Although any methods and materials similar or equivalent to those described herein can be used in the practice or testing of the present invention, the preferred methods and materials are described.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with general dictionaries of many of the terms used in this invention.

The headings provided herein are not limitations of the various aspects or embodiments of the invention which can be had by reference to the specification as a whole. Accordingly, the terms defined immediately below are more fully defined by reference to the specification as a whole. Numeric ranges are inclusive of the numbers defining the range. Unless otherwise indicated, nucleic acids are written left to right in 5' to 3' orientation; amino acid sequences are written left to right in amino to carboxy orientation, respectively.

It should be noted that, as used in this specification and the appended claims, the singular forms "a," "an," and "the" include plural references unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Definitions

A "signal sequence" or "signal peptide" means a sequence of amino acids bound to the N-terminal portion of a protein which facilitates the secretion of the mature form of the protein outside the cells. The definition of a signal sequence is a functional one. The mature form of the extracellular protein lacks the signal sequence which is cleaved off during the secretion process.

An "NSP24 signal peptide" refers to an N-terminally extended sequence which has the sequence of SEQ ID NO:4 or a variant which functions as a signal sequence. An "NSP24 signal peptide" may be interchangeably referred to as an "NSP24 peptide" and "NSP aspartic protease signal peptide".

As used herein, "NSP24 family protease" means an enzyme having protease activity in its native or wild type form and belonging to the family of NSP24 proteases.

As used herein, a "native sequence NSP24" or "wildtype NSP24 sequence" includes a polypeptide having the same amino acid sequence as an NSP24 family protease derived from nature.

As used herein, "operably linked" means that a regulatory region, such as a promoter, terminator, secretion signal or enhancer region is attached to or linked to a structural gene and controls the expression of that gene. A signal sequence is operably linked to a protein if it directs the protein through the secretion system of a host cell.

The terms "isolated" or "purified" refers to a protein that is altered from its natural state by virtue of separating the protein from one or more or all of the naturally occurring constituents with which it is associated in nature.

The terms "peptides", "proteins", and "polypeptides" are used interchangeably herein.

As used herein, "percent (%) sequence identity" with respect to the amino acid or nucleotides sequences identified is defined as the percentage of amino acid residues or nucleotides in a candidate sequence that are identical with the amino acid residues or nucleotides in a sequence of interest (e.g. a NSP24 signal peptide sequence), after aligning the sequences and introducing gaps, if necessary, to achieve the maximum percent sequence identity, and not considering any conservative substitutions as part of the sequence identity.

"Homologous", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

As used herein the term "vector" refers to a polynucleotide sequence designed to introduce nucleic acids into one or more cell types. Vectors include cloning vectors, expression vectors, shuttle vectors, plasmids, phage particles, cassettes and the like.

As used herein, "expression vector" means a DNA construct including a DNA sequence which is operably linked to a suitable control sequence capable of affecting the expression of the DNA in a suitable host.

The term "expression" means the process by which a polypeptide is produced based on the nucleic acid sequence of a gene.

As used herein, a substance (e.g. a polynucleotide or protein) "derived from" a microorganism means "isolated from" and means that the substance is native to the microorganism.

As used herein, "microorganism" refers to a bacterium, a fungus, a virus, a protozoan, and other microbes or microscopic organisms.

As used herein, "host strain" or "host cell" means a suitable host for an expression vector including DNA according to the present invention and includes progeny of said cells.

The term "filamentous fungi" refers to all filamentous forms of the subdivision Eumycotina (See, Alexopoulos, C. J. (1962), INTRODUCTORY MYCOLOGY, Wiley, New York and AINSWORTH AND BISBY DICTIONARY OF THE FUNGI, 9$^{th}$ Ed. (2001) Kirk et al., Eds., CAB International University Press, Cambridge UK). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic.

As used herein, the term "*Trichoderma*" or "*Trichoderma* sp.*" refer to any fungal genus previously or currently classified as *Trichoderma*.

As used herein the term "culturing" refers to growing a population of microbial cells under suitable conditions in a liquid or solid medium.

As used herein the term "contacting" refers to the placing of nucleic acids in sufficiently close proximity to the respective host to enable the nucleic acids to be taken up.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations. By "stably integrated" means that the episomal plasmic is maintained through multiple generations.

As used herein the term "heterologous" with reference to a polypeptide or polynucleotide means a polypeptide or polynucleotide that is not naturally secreted using the NSP24 signal sequence. In some cases the heterologous protein is a polypeptide or polynucleotide that does not naturally occur in a host cell. In some embodiments, the polypeptide is a commercially important industrial protein or a protein of interest. It is intended that the term encompass proteins that are encoded by naturally occurring genes, mutated genes and/or synthetic genes. In some embodiments, the heterologous protein can be an endogenous protein (naturally occurs in the host cell), but is expressed in a non-natural way. Meaning that the protein is expressed from a non-natural promoter and/or signal sequence. Thus, a signal sequence is operably linked to a coding sequence that it is not usually operably linked to in a wild-type host cell.

The term "homologous" or "endogenous" with reference to a polynucleotide or protein refers to a polynucleotide or protein that occurs naturally in the host cell.

As used herein a "protein of interest" is a heterologous protein. A protein of interest may also be an endogenous protein that is expressed heterologously.

As used herein, a "fusion protein" or "fusion polypeptide" comprises an NSP24 signal peptide operatively linked to a polypeptide/protein of interest.

As used herein, the term "expression" refers to the process by which a polypeptide is produced based on the nucleic acid sequence of a gene. The process includes both transcription and translation.

As described herein, one aspect of the invention features a "substantially pure" (or recombinant) nucleic acid that includes a nucleotide sequence encoding an NSP24 signal peptide operably linked to a heterologous protein, and/or equivalents of such nucleic acids.

The term "equivalent" refers to nucleotide sequences encoding functionally equivalent polypeptides. Equivalent nucleotide sequences will include sequences that differ by one or more nucleotide substitutions, additions or deletions, such as allelic variants. For example in some embodiments, due to the degeneracy of the genetic code equivalent nucleotide sequences include sequences that differ from the nucleotide sequence of SEQ ID NO: 4.

The term "selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

Aspartic Protease (NSP24) Signal Peptides and Polynucleotides Encoding the Same—

The invention is at least partially based on the identification that the aspartic protease (NSP24) signal peptide can be used for the expression and secretion of heterologous proteins. The NSP24 gene was isolated and sequenced from *Trichoderma reesei* (see U.S. patent Ser. No. 11/312,290 "ACID FUNGAL PROEASES", filed Dec. 20, 2005, herein incorporated by reference in its entirety). Sequencing identified a 407 amino acid open reading frame (SEQ ID NO:2) shown in FIG. 1b. A signal peptide was identified (shown in bold in FIG. 1b) and comprises the first 20 amino acids MQTFGAFLVSFLAAS-GLAAA (SEQ ID NO:4) of SEQ ID NO:2. The DNA sequence of the NSP24 gene is provided in FIG. 1a (SEQ ID NO:1). In FIG. 1b, the signal peptide is in bold (SEQ ID NO:4), the prepro sequence is underlined and the mature NSP24 protein starts with KYG . . . and is represented by SEQ ID NO: 3.

The invention relates to the use of NSP24 family protease signal peptides, having at least 95%, at least 97%, at least 98% and at least 99% sequence identity to the signal peptide of SEQ ID NO: 4 to express and secrete heterologous proteins in filamentous fungal cells. In some embodiments, the NSP24 signal peptide is designated NSP24 aspartic protease signal peptide.

In some embodiments, the NSP24 signal peptides are biologically active fragments or variants which are able to act as signal peptides, for example to secrete proteins from a host cell. Thus, the NSP24 signal peptide having at least 95% sequence identity, 97%, 98%, and/or 99% sequence identity to the amino acid sequence of SEQ ID NO: 4 acts to increase secretion of a protein from a host cell. In some embodiments, the active variant is a truncated version of the NSP24 signal peptide having at least 19 amino acids, at least 18 amino acids, at least 17 amino acids, and/or at least 16 amino acids and still able to function as a signal peptide.

Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequences. Preferably, amino acid "substitutions" are the result of replacing one amino acid with another amino acid having similar structural and/or chemical properties, i.e., conservative amino acid replacements may be made on the basis of similarity in polarity, change, solubility, hydrophobicity, and/or the amphipathic nature of the residues involved. Examples of conservative substitutions are those between the following groups: Gly/Ala, Val/Ile/Leu, Lys/Arg, Asn/Gln, Glu/Asp, Ser/Cys/Thr, and Phe/Trp/Tyr. A variant may, for example, differ by as few as 1 to 10 amino acid residues, such as 6-10, as few as 5, as few as 4, 3, 2, or even 1 amino acid residue. Table 1 illustrates exemplary amino acid substitutions that are recognized in the art. In addition, substitution may be by one or more non-conservative amino acid substitutions, deletions, or insertions that do not abolish the signal peptide activity.

TABLE 1

CONSERVATIVE AMINO ACID REPLACEMENTS

| For Amino Acid | Code | Replace with any of |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

The present invention also provides isolated NSP24 peptides encoded by the nucleic acids/polynucleotides of the present invention or by degenerate variants of the nucleic acids of the invention. By "degenerate variants" is intended nucleotide fragments that differ from a nucleic acids of the invention by nucleotide sequence but, due to the degeneracy of the genetic code, encode an identical polypeptide sequence.

The invention provides for fusion polypeptides. As used herein, a fusion protein or fusion polypeptide comprises an NSP24 signal peptide operatively linked to a heterologous polypeptide/protein of interest. Within the fusion protein, the term "operatively linked" is intended to indicate that the NSP24 signal polypeptide and the polypeptide of interest are fused in-frame to one another. The NSP24 signal peptides are fused to the N-terminal end of the heterologous protein. Polypeptides of interest include heterologous polypeptides. Polypeptides of interest include full-length polypeptides that are naturally synthesized with a signal peptide, the mature form of the full-length polypeptides, and polypeptides that lack a signal peptide.

In some embodiments, the fusion polypeptide comprises an NSP24 signal peptide that is the secretory leader sequence of polypeptides that are naturally expressed by *Trichoderma* that is operably linked to a heterologous polypeptide or protein of interest. In some embodiments, the fusion polypeptide comprises an NSP24 signal peptide and a heterologous polypeptide such as an enzyme, a growth factor or a hormone. Enzymes include, but are not limited to: phytases, proteases, carbohydrases (such as amylases, cellulases, xylanases, and lipases), isomerases (such as racemases, epimerases, tautomerases, or mutases, transferases, glucoamylases, kinases, amidases, esterases, oxidases, and laccases. Thus, the protein of interest can be an enzyme such as an alpha amylase, an alkaline alpha amylase, a beta amylase, a cellulase, a beta glucosidase, a beta glucanase, a dextranase, an alpha glucosidase, a glucoamylase, a pullulanase, a pectinase, a protease, a xylanase, a hemicellulase, a pentosanase, an inveratase, a laccase, a lactase, a lipase, an esterase, a phytase, a phospholipase, a pregastric esterase, an iminoacylase, a glutaminase, a lysozyme, a glucose isomerase, an oxidase, a catalase, a glucose oxidase, a lyase, a fumerase, a transferase, mannosidases, a beta galactosidases, a mutanase, a ligase, and a peroxidase. The enzyme can be a wild-type enzyme or a variant of a wild-type enzyme. The enzyme can be a domain of an enzyme, such as a catalytic domain of an alpha amylase. The enzyme can be a hybrid enzyme, which comprises a least two fragments from different enzymes, for example, a catalytic domain of one enzyme and a starch binding domain of a different enzyme. Or the hybrid enzyme can be two fragments each comprising a part of the catalytic domain of the enzymes. In some embodiments, the fusion polypeptide of the invention comprises an NSP24 signal peptide as recited herein, and a heterologous protein. In other embodiments, the fusion polypeptide of the invention comprises an NSP24 signal peptide as recited herein, and an enzyme that is a protease, a carbohydrase, an isomerase, a glucoamylase, a kinase, an amidase, an esterase, or an oxidase. In some embodiments, the enzyme is naturally associated with a signal peptide. In other embodiments, the enzyme is not naturally associated with a signal peptide.

In some embodiments, the NSP24 signal peptides of the invention are native sequences. Such a native sequence can be isolated from nature or can be produced by recombinant or synthetic means. The term "native sequence" specifically encompasses naturally-occurring truncated or secreted forms of an NSP24 signal peptide sequence (e.g., biologically active fragments), and naturally-occurring variant forms.

A nucleic acid is hybridizable to another nucleic acid sequence when a single stranded form of the nucleic acid can anneal to the other nucleic acid under appropriate conditions of temperature and solution ionic strength. Hybridization and washing conditions are well known in the art for hybridization under low, medium, high and very high stringency conditions (See, e.g., Sambrook (1989) supra, particularly chapters 9 and 11). In general hybridization involves a nucleotide probe and a homologous DNA sequence that from stable double stranded hybrids by extensive base-pairing of complementary polynucleotides (Also see, Chapter 8, Gene Cloning, An Introduction, T. A. Brown (1995) Chapman and Hall London). In some embodiments the filter with the probe and homologous sequence may be washed in 2× sodium chloride/sodium citrate (SSC), 0.5% SDS at about 60° C. (medium stringency), 65° C. (medium/high stringency), 70° C. (high stringency) and about 75° C. (very high stringency) (Current Protocols in Molecular Biology, John Wiley & Sons, New York, 1989, 6.3.1-6.3.6, hereby incorporated by reference);

Included in the invention are: allelic variations; natural mutants; induced mutants; proteins encoded by DNA that hybridizes under high or low stringency conditions to a nucleic acid which encodes a peptide of SEQ ID NO: 4. Nucleic acids and polypeptides of the invention include those that differ from the sequences disclosed herein by virtue of sequencing errors in the disclosed sequences.

Homology of DNA sequences is determined by the degree of identity between two DNA sequences. Homology or percent identity may be determined for polypeptide sequences or nucleotides sequences using computer programs. Methods for performing sequence alignment and determining sequence identity are known to the skilled artisan, may be performed without undue experimentation, and calculations of identity values may be obtained with definiteness. See, for example, Ausubel et al., eds. (1995) Current Protocols in Molecular Biology, Chapter 19 (Greene Publishing and Wiley-Interscience, New York); and the ALIGN program (Dayhoff (1978) in Atlas of Protein Sequence and Structure 5:Suppl. 3 (National Biomedical Research Foundation, Washington, D.C.). A number of algorithms are available for aligning sequences and determining sequence identity and include, for example, the homology alignment algorithm of Needleman et al. (1970) J. Mol. Biol. 48:443; the local homology algorithm of Smith et al. (1981) Adv. Appl. Math. 2:482; the search for similarity method of Pearson et al. (1988) Proc. Natl. Acad. Sci. 85:2444; the Smith-Waterman algorithm (Meth. Mol. Biol. 70:173-187 (1997); and BLASTP, BLASTN, and BLASTX algorithms (see Altschul et al. (1990) J. Mol. Biol. 215:403-410). Computerized programs using these algorithms are also available, and include, but are not limited to: ALIGN or Megalign (DNASTAR) software, or WU-BLAST-2 (Altschul et al., Meth. Enzym., 266:460-480 (1996)); or GAP, BESTFIT, BLAST Altschul et al., supra, FASTA, and TFASTA, available in the Genetics Computing Group (GCG) package, Version 8, Madison, Wis., USA; and CLUSTAL in the PC/Gene program by Intelligenetics, Mountain View, Calif. Those skilled in the art can determine appropriate parameters for measuring alignment, including algorithms needed to achieve maximal alignment over the length of the sequences being compared. Preferably, the sequence identity is determined using the default parameters determined by the program. Specifically, sequence identity can be determined by the Smith-Waterman homology search algorithm (Meth. Mol. Biol. 70:173-187 (1997)) as implemented in MSPRCH program (Oxford Molecular) using an affine gap search with the following search parameters: gap open penalty of 12, and gap extension penalty of 1. Preferably, paired amino acid comparisons can be carried out using the GAP program of the GCG sequence analysis software package of Genetics Computer Group, Inc., Madison, Wis., employing the blosum62 amino acid substitution matrix, with a gap weight of 12 and a length weight of 2. With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for increased sequence identity associated with inclusion of gaps in the variants amino acid sequence can be made by assigning gap penalties.

In some embodiments, the NSP24 signal peptides encompassed by the invention (e.g. an NSP24 signal peptide having at least 95% sequence identity to the sequence of SEQ ID NO: 4), is derived from a bacterium or a fungus, such as a filamentous fungus. Some preferred filamentous fungi include *Aspergillus* spp. and *Trichoderma* spp. One preferred *Trichoderma* spp. is *T. reesei*. However, the signal peptide and/or DNA encoding the signal peptide according to the instant invention may be derived from a fungus, such as, *Absidia* spp.; *Acremonium* spp.; *Agaricus* spp.; *Anaeromyces* spp.; *Aspergillus* spp., including *A. aculeatus, A. awamori, A. flavus, A. foetidus, A. fumaricus, A. fumigatus, A. nidulans, A. niger, A. oryzae, A. terreus* and *A. versicolor; Aeurobasidium* spp.; *Cephalosporum* spp.; *Chaetomium* spp.; *Coprinus* spp.; *Dactyllum* spp.; *Fusarium* spp., including *F. conglomerans, F. decemcellulare, F. javanicum, F. lini, F. oxysporum* and *F. solani; Gliocladium* spp.; *Humicola* spp., including *H. insolens* and *H. lanuginosa; Mucor* spp.; *Neurospora* spp., including *N. crassa* and *N. sitophila; Neocallimastix* spp.; *Orpinomyces* spp.; *Penicillium* spp; *Phanerochaete* spp.; *Phiebia* spp.; *Piromyces* spp.; *Rhizopus* spp.; *Schizophyllum* spp.; *Trametes* spp.; *Trichoderma* spp., including *T. reesei, T. reesei* (longibrachiatum) and *T. viride*; and *Zygorhynchus* spp.

Host Cells—

In some embodiments, this invention provides for host cells transformed with DNA constructs and vector as described herein. In some embodiments, the invention provides for host cells transformed with DNA constructs encoding a heterologous protein encompassed by the invention and operably linked to the NSP24 signal peptide encompassed by the invention. In some embodiments, the invention provides DNA constructs introduced into a host cell that code for a heterologous phytase, protease, alpha amylase, glucoamylase, xylanase, cellulose, and or any protein of interest. In some embodiments the invention provides for the expression of heterologous protein genes under control of gene promoters functional in host cells such as bacterial and fungal host cells.

The type of host cell used in the invention is not critical, but is preferably a cell in which the NSP24 signal peptide has activity in secreting the heterologous protein of interest. The type of host cells for which a *T. reesei* signal peptide is expected to have activity, includes but is not limited to fungal and bacterial cells. Some preferred host cells include filamentous fungal cells. Non-limiting examples of filamentous fungal host cells include *Trichoderma* spp. (e.g. *T. viride* and *T. reesei*, the asexual morph of *Hypocrea jecorina*, previously classified as *T. longibrachiatum*), *Penicillium* spp., *Humicola* spp. (e.g. *H. insolens* and *H. grisea*), *Aspergillus* spp. (e.g., *A. niger, A. nidulans, A. orzyae*, and *A. awamon*), *Fusarium* spp. (*F. graminum*), *Neurospora* spp., *Hypocrea* spp. and *Mucor* spp. Further host cells may include *Bacillus* spp (e.g. *B. subtilis, B. licheniformis, B. lentus, B. stearothremophilus* and *B. brevis*) and *Streptomyces* spp. (e.g., *S. coelicolor* and *S. lividans* (TK23 and TK21)). However, many methods are known for identifying whether a heterologous protein is secreted in a host cell or remains in the cytoplasm. These methods can be used to identify host cells in which the signal sequence is active.

Molecular Biology—

This invention relies on routine techniques in the field of recombinant genetics. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Ausubel et al., eds., Current Protocols in Molecular Biology (1994)).

Heterologous genes comprising gene promoter sequences, for example, of filamentous fungi are typically cloned into intermediate vectors before transformation into host cells, such as *Trichoderma reesei* cells for replication and/or expression. These intermediate vectors are typically prokaryotic vectors, e.g., plasmids, or shuttle vectors.

To obtain high level expression of a cloned gene, the heterologous gene is preferably positioned about the same distance from the promoter as in the naturally occurring gene. As is known in the art, however, some variation in this distance can be accommodated without loss of promoter function.

Those skilled in the art are aware that a natural promoter can be modified by replacement, substitution, addition or elimination of one or more nucleotides without changing its function. The practice of the invention encompasses and is not constrained by such alterations to the promoter.

The expression vector/construct typically contains a transcription unit or expression cassette that contains all the additional elements required for the expression of the heterologous sequence. A typical expression cassette thus contains a promoter operably linked to the heterologous nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites, secretion leader peptides, leader sequences, linkers, and cleavage sites.

The practice of the invention is not constrained by the choice of promoter in the genetic construct. However, exemplary promoters are the *Trichoderma reesei* cbh1, cbh2, eg1, eg2, eg3, eg5, xln1 and xln2 promoters. Also promoters from *A. awamori* and *A. niger* glucoamylase genes (glaA) (Nunberg et al., (1984) *Mol. Cell Biol.* 4:2306-2315) and the promoter from *A. nidulans* acetamidase find use in the vectors. A preferred promoter for vectors used in *Bacillus subtilis* is the AprE promoter; a preferred promoter used in *E. coli* is the Lac promoter, a preferred promoter used in *Saccharomyces cerevisiae* is PGK1, a preferred promoter used in *Aspergillus niger* is glaA, and a preferred promoter for *Trichoderma reesei* is cbhI.

In addition to a promoter sequence, the expression cassette can also contain a transcription termination region downstream of the structural gene to provide for efficient termination. The termination region may be obtained from the same gene as the promoter sequence or may be obtained from different genes.

Although any fungal terminator is likely to be functional in the present invention, some preferred terminators include: the terminator from *Aspergillus nidulans* trpC gene (Yelton, M. et al. (1984) PNAS USA 81:1470-1474, Mullaney, E. J. et al. (1985) MGG 199:37-45), the *Aspergillus awamori* or *Aspergillus niger* glucoamylase genes (Nunberg, J. H. et al. (1984) Mol. Cell. Biol. 4:2306, Boel, E. et al. (1984) EMBO J. 3:1581-1585), the *Aspergillus oryzae* TAKA amylase gene, and the *Mucor miehei* carboxyl protease gene (EPO Publication No. 0 215 594).

The particular expression vector used to transport the genetic information into the cell is not particularly critical. Any of the conventional vectors used for expression in eukaryotic or prokaryotic cells may be used. Examples of suitable expression and/or integration vectors are provided in Sambrook et al., (1989) supra, Bennett and Lasure (Eds.) More Gene Manipulations in Fungi, (1991) Academic Press pp. 70-76 and pp. 396-428 and articles cited therein; U.S. Pat. No. 5,874,276 and Fungal Genetic Stock Center Catalogue of Strains, (FGSC, www.fgsc.net.). However, the invention is intended to include other forms of expression vectors which serve equivalent functions and which are, or become, known in the art. Thus, a wide variety of host/expression vector combinations may be employed in expressing the DNA sequences of this invention.

In some embodiments, an expression vector includes a selectable marker. Examples of selectable markers include ones which confer antimicrobial resistance. Nutritional markers also find use in the present invention including those markers known in the art as amdS, argB and pyr4. Markers useful for the transformation of *Trichoderma* are known in the art (see, e.g., Finkelstein, chapter 6, in Biotechnology of Filamentous Fungi, Finkelstein et al., EDS Butterworth-Heinemann, Boston Mass. (1992) and Kinghorn et al., (1992) Applied Molecular Genetics of Filamentous Fungi, Blackie Academic and Professional, Chapman and Hall, London). In some embodiments, the expression vectors will also include a replicon, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable. The prokaryotic sequences are preferably chosen such that they do not interfere with the replication or integration of the DNA in *Trichoderma reesei*.

In some embodiments, an expression vector includes a reporter gene alone or, optionally as a fusion with the protein of interest. Examples of reporter genes includes but is not limited to, fluorescent reporters, color detectable reporters (□ galactosidase), and biotinylated reporters. For example, the reporter molecule when expressed can be used to identify whether the signal peptide is active in a host cell. If the signal peptide is active, the reporter molecule will be secreted from the cell. The signal peptide can be operably linked to the reporter initially to identify secretion from a particular host cell. Alternative methods such as those using antibodies specific to the protein of interest and/or the signal peptide can be used to identify whether the protein of interest is secreted.

In one embodiment, the vector pTrex3g (FIG. 2) is used for transformation by a method according to the invention. This vector is based on the *E. coli* vector pSL1180 (Pharmacia Inc., Piscataway, N.J.) which is a pUC118 phagemid based vector (Brosius, J. (1989), DNA 8:759) with an extended multiple cloning site containing 64 hexamer restriction enzyme recognition sequences. The vector is designed as a Gateway destination vector (Hartley et al., (2000) *Genome Research* 10:1788-1795) to allow insertion using Gateway technology (Invitrogen) of any desired open reading frame between the promoter and terminator regions of the *T. reesei* cbh1 gene. It also contains the *Aspergillus nidulans* amdS gene for use as a selective marker in the electroporation transformation method of the invention. However, as mentioned above the fusion protein encompassed by the invention is not limited by the type of vector.

The methods of transformation of the present invention may result in the stable integration of all or part of the transformation vector into the genome of a host cell, such as a filamentous fungal host cell. However, transformation resulting in the maintenance of a self-replicating extra-chromosomal transformation vector is also contemplated.

Many standard transfection methods can be used to produce bacterial and filamentous fungal (e.g. *Aspergillus* or *Trichoderma*) cell lines that express large quantities of the heterologous proteins. Some of the published methods for the introduction of DNA constructs into *Trichoderma* include Lorito, Hayes, DiPietro and Harman, (1993) Curr. Genet. 24: 349-356; Goldman, VanMontagu and Herrera-Estrella, (1990) Curr. Genet. 17:169-174; and Penttila, Nevalainen, Ratto, Salminen and Knowles, (1987) Gene 6: 155-164, also see U.S. Pat. No. 6,022,725; U.S. Pat. No. 6,268,328 and Nevalainen et al., "The Molecular Biology of *Trichoderma* and its Application to the Expression of Both Homologous and Heterologous Genes" in Molecular Industrial Mycology, Eds, Leong and Berka, Marcel Dekker Inc., NY (1992) pp 129-148; for *Aspergillus* include Yelton, Hamer and Timberlake, (1984) Proc. Natl. Acad. Sci. USA 81: 1470-1474, for *Fusarium* include Bajar, Podila and Kolattukudy, (1991) Proc. Natl. Acad. Sci. USA 88: 8202-8212, for *Streptomyces* include Hopwood et al., 1985, Genetic Manipulation of *Streptomyces*: Laboratory Manual, The John Innes Foundation, Norwich, UK and Fernandez-Abalos et al., Microbiol 149:1623-1632 (2003) and for *Bacillus* include Brigidi, DeRossi, Bertarini, Riccardi and Matteuzzi, (1990) FEMS Microbiol. Lett. 55: 135-138).

However, any of the well-known procedures for introducing foreign nucleotide sequences into host cells may be used. These include the use of calcium phosphate transfection, polybrene, protoplast fusion, electroporation, lithium acetate, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). Also of use is the *Agrobacterium*-mediated transfection method described in U.S. Pat. No. 6,255,115. It is only necessary that the particular genetic engineering procedure used be capable of successfully introducing at least one gene into the host cell capable of expressing the gene. In one embodiment, the invention concerns a method for producing a heterologous protein encompassed by the invention which comprises introducing into a host cell a polynucleotide comprising an NSP24 signal peptide linked to a nucleic acid encoding a heterologous protein, culturing the host cell under suitable culture conditions for the expression and production of the heterologous protein, and producing said heterologous protein. In some preferred embodiments, the heterologous protein is secreted from the host cell.

After the expression vector is introduced into the cells, the transfected or transformed cells are cultured under conditions favoring expression of genes under control of the gene promoter sequences. Large batches of transformed cells can be cultured. Finally, product is recovered from the culture using standard techniques.

Thus, the invention herein provides for the expression and secretion of heterologous polypeptides (protein of interest) by operably linking the NSP24 signal peptide sequence to a heterologous protein and/or protein of interest. Aspects of the invention provide processes for expressing and secreting high levels of such desired polypeptides.

Heterologous Proteins

The term "heterologous protein" means any protein that is not naturally operably linked to the NSP24 signal sequence. The heterologous protein can be a protein that does not naturally occur in a host cell. Alternatively the heterologous protein can be an endogenous protein that is heterologously expressed. The heterologous protein can be any protein other than the NSP24 protein from which the signal peptide is obtained.

The type of heterologous protein is not critical to the invention, but can be any protein of interest. Some non-limiting examples of heterologous proteins useful in compositions and applications according to the invention include for example phytases, glucoamylases, alpha amylases, granular starch hydrolyzing enzymes, cellulases, lipases, xylanases, cutinases, hemicellulases, proteases, oxidases, laccases and combinations thereof.

In some embodiments, the phytase is BP-wild type, a variant thereof (such as BP-11) disclosed in WO 06/043178 or a variant as disclosed in U.S. patent application Ser. No.

11/714,487, filed Mar. 6, 2007. For example, a BP-wild type and variants thereof are disclosed in Table 1 of WO 06/043178, wherein the numbering is in reference to SEQ ID NO:3 of the published PCT application.

In one preferred embodiment, a phytase useful in the instant invention is one having at least 75%, at least 80%, at least 85%, at least 88%, at least 90%, at least 93%, at least 95%, at least 96%, at least 97%, at least 98% and at least 99% sequence identity to the amino acid sequence set forth in SEQ ID NO:5 shown in FIG. 4b and variants thereof. More preferably, the phytase will have at least 95% to 99% sequence identity to the amino acid sequence set forth in SEQ ID NO:5 or variants thereof. In some embodiments, the phytase comprises or consists of the amino acid sequence of SEQ ID NO:5.

Heterologous Protein Expression

Heterologous proteins of the present invention are produced by culturing cells transformed with a vector such as an expression vector containing genes secreted by fusion with the NSP24 signal peptide sequence. The present invention is particularly useful for the intracellular and/or extracellular production of heterologous proteins encompassed by the invention. Optimal conditions for the production of the proteins will vary with the choice of the host cell, and with the choice of heterologous protein to be expressed. Such conditions will be easily ascertained by one skilled in the art through routine experimentation or optimization.

The heterologous protein of interest may be isolated or recovered and purified after expression. The protein of interest may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the protein of interest may be purified using a standard anti-protein of interest antibody column. Ultrafiltration and diafiltration techniques, in conjunction with protein concentration, are also useful. For general guidance in suitable purification techniques, see Scopes, Protein Purification (1982). The degree of purification necessary will vary depending on the use of the protein of interest. In some instances no purification will be necessary.

Cell Culture

Host cells and transformed cells can be cultured in conventional nutrient media. The culture media for transformed host cells may be modified as appropriate for activating promoters and selecting transformants. The specific culture conditions, such as temperature, pH and the like, may be those that are used for the host cell selected for expression, and will be apparent to those skilled in the art. In addition, preferred culture conditions may be found in the scientific literature such as Sambrook, (1982) supra; Kieser, T, M J. Bibb, M J. Buttner, K F Chater, and D. A. Hopwood (2000) PRACTICAL STREPTOMYCES GENETICS. John Innes Foundation, Norwich UK; Harwood, et al., (1990) MOLECULAR BIOLOGICAL METHODS FOR BACILLUS, John Wiley and/or from the American Type Culture Collection (ATCC; www.atcc.org). Stable transformants of fungal host cells, such as Trichoderma cells can generally be distinguished from unstable transformants by their faster growth rate or the formation of circular colonies with a smooth rather than ragged outline on solid culture medium.

Recovery of Expressed Polypeptides and Methods for Purifying the Heterologous Proteins—

A heterologous protein of interest encompassed by the invention, produced by the transformed host cell may be recovered from the culture medium by conventional procedures including separating the host cells from the medium by centrifugation or filtration, or if necessary, disrupting the cells and removing the supernatant from the cellular fraction and debris. In some cases, after clarification, the proteinaceous components of the supernatant or filtrate are precipitated by means of a salt, e.g., ammonium sulphate. The precipitated proteins are then solubilized and may be purified by a variety of chromatographic procedures, e.g., ion exchange chromatography, gel filtration chromatography, affinity chromatography, and other art-recognized procedures. Antibodies to the peptides and proteins can be made by immunizing an animal, e.g., a rabbit or mouse, and recovering anti-heterologous protein and/or NSP24 signal peptide antibodies by prior art methods. Assays that find use in the present invention include, but are not limited to those described in WO 9934011 and U.S. Pat. No. 6,605,458.

Compositions—

In some embodiments, the present invention is directed to expression of heterologous proteins using the NSP24 signal sequence, constructs and vectors as described herein. Compositions comprising the heterologous protein of interest can be used in a variety of applications. Compositions may further include additional enzymes, such as, but not limited to, glucoamylases, alpha amylases, granular starch hydrolyzing enzymes, cellulases, lipase, xylanases, cutinases, hemicellulases, oxidases, laccases and combinations thereof.

Applications

The heterologous proteins produced by the present invention can be used in any applications appropriate for that protein. Examples of applications for heterologous proteins such as enzymes includes, but is not limited to the following: Animal feeds for improvement of feed intake and feed efficiency (proteases), dietary protein hydrolysates for those with impaired digestive system, leather treatment, treatment of protein fibers, such as wool and silk, cleaning, protein processing (for example to remove bitter peptides, to enhance the flavor of food, to produce cheese and cocoa), personal care products (such as hair compositions), sweeteners (production of high maltose or high fructose syrups for example), and fermentation and bioethanol (alpha amylases and glucoamylases can be used to treat grains for fermentation).

EXAMPLES

The present invention is described in further detail in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

EXPERIMENTAL

The invention is further defined by reference to the following examples, which describe in detail, preparation of compounds of the invention and methods for assaying for biological activity. It will be apparent to those skilled in the art that many modifications, both to materials and methods, may be practiced without departing from the scope of the invention.

In the experimental disclosure which follows, the following abbreviations apply: M (Molar); μM (micromolar); N (Normal); mol (moles); mmol (millimoles); μmol (micromoles); nmol (nanomoles); g (grams); mg (milligrams); kg (kilograms); μg (micrograms); L (liters); ml (milliliters); μl (microliters); cm (centimeters); mm (millimeters); μm (micrometers); nm (nanometers); ° C. (degrees Centigrade); h (hours); min (minutes); sec (seconds); msec (milliseconds); V (voltage); F (Fahrenheit).

EXAMPLES

Example 1

Figure 3:
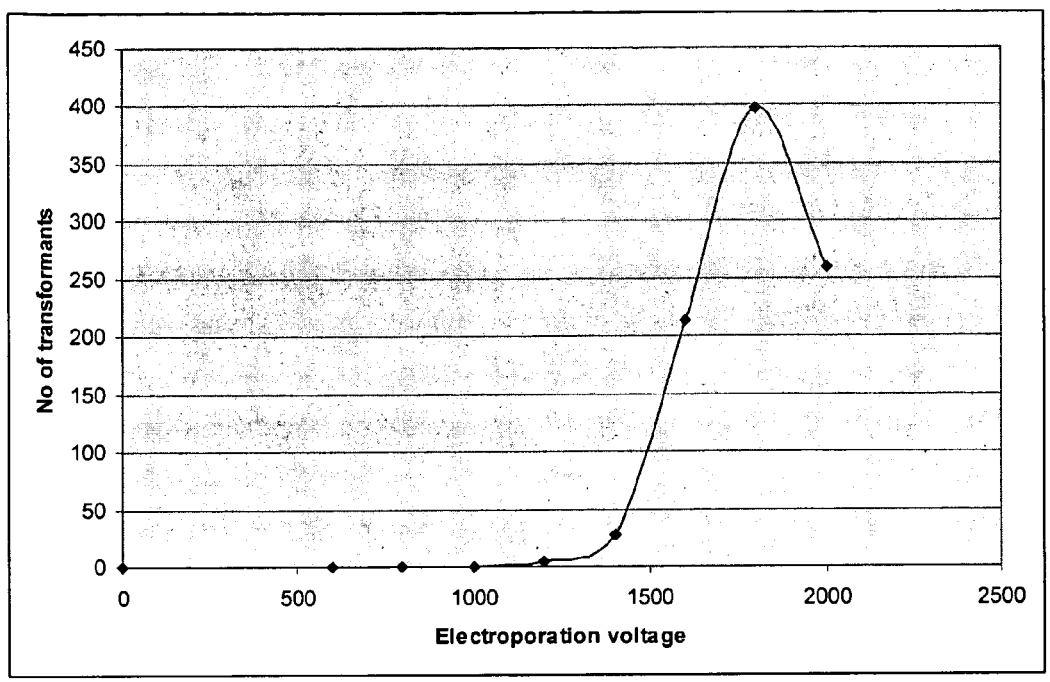
FIG. 3 illustrates the electroporation efficiency of *T. reesei* spores as a function of voltage.
Figure 5:
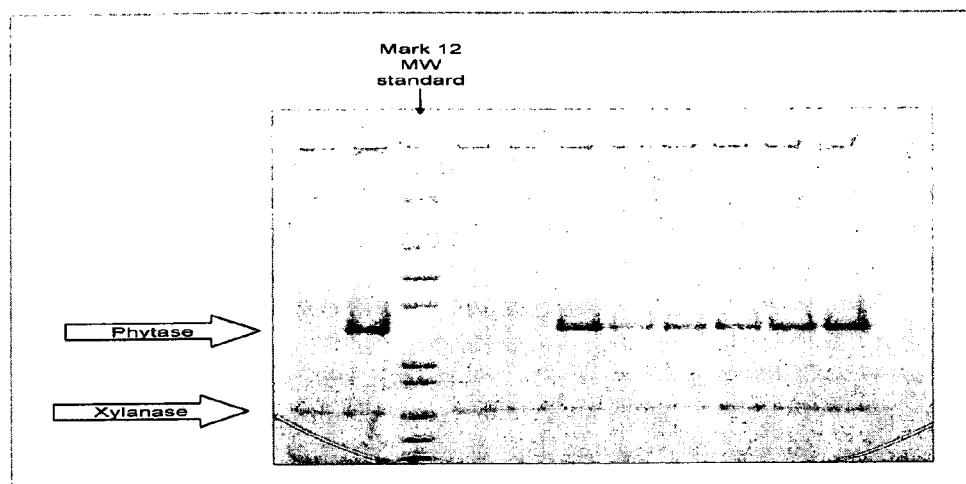
FIG. 5 shows the expression of SDS PAGE analysis of 10 clones from a set of *Trichoderma reesei* transformants with an expression cassette having a polynucleotide that codes for a polypeptide having phytase activity.

Electroporation Efficiency of *Trichoderma reesei* Spores as a Function of Electroporation Voltage A *T. reesei* strain derived from G1CC2984 (pyr$^+$) was grown and sporulated on Potato Dextrose Agar plates (Difco) for about 10-20 days. The spores were washed from the surface of the plates with water and purified by filtration through Miracloth (Calbiochem). The spores were collected by centrifugation (3000×G, 12 min), washed once with ice-cold water and once with ice-cold 1.1M sorbitol. The spore pellet was re-suspended in a small volume of cold 1.1 M sorbitol, mixed with about 8 μg of XbaI hydrolysate of pTrex3 (FIG. 2) per 100 μl of spore suspension. The mixture (100 μl) was placed into an electroporation cuvette (1 mm gap) and subjected to an electric pulse using the following electroporation parameters: voltage 6000-20000 V/cm, capacitance=25 μF, resistance=50Ω. After electroporation, the spores were diluted about 100-fold into 5:1 mixture of 1.1 M sorbitol and YEPD (1% yeast extract, 2% Bacto-peptone, 2% glucose, pH 5.5), placed in shake flasks and incubated for 16-18 hours in an orbital shaker (28° C. and 200 rpm). The spores were once again collected by centrifugation, re-suspended in about 10-fold of pellet volume of 1.1 M sorbitol and plated onto two 15 cm Petri plates containing amdS modified medium (acetamide 0.6 g/l, cesium chloride 1.68 g/l, glucose 20 g/l, potassium dihydrogen phosphate 15 g/l, magnesium sulfate heptahydrate 0.6 g/l, calcium chloride dihydrate 0.6 g/l, iron (II) sulfate 5 mg/l, zinc sulfate 1.4 mg/l, cobalt (II) chloride 1 mg/l, manganese (II) sulfate 1.6 mg/l, agar 20 g/l and pH 4.25). Transformants appeared until about 1 week of incubation. Counting of colonies at this stage was difficult because of overgrowths of early transformants. Therefore, numerical estimates were made by counting transformants after 4 days of incubation. As can be seen from the data presented on FIG. 3 optimal voltage for transformation of *T. reesei* spores is about 18000 V/cm. However, at this high voltage "arcing" in the electroporation cuvette is often a problem. The use of 16 000V/cm significantly reduced arcing while retaining acceptable transformation efficiency. No transformants were obtained using the voltage range of 6000-8000V/cm.

Example 2

Transformation of a Recombinant *Trichoderma reesei* Strain with a Phytase Expression Cassette In this example, a recombinant *T. reesei* strain GICC2984 was used for transformation. The recombinant strain expresses a mutant form of *T. reesei* xylanase designated Y5. This xylanase is a thermostable mutant form of a *T. reesei* xylanase (Fenel et al., International Publication No. WO 0127252). The expression vector used to transform the recombinant *T. reesei* strain included the coding sequence for a polypeptide having phytase activity (see FIG. 4). The phytase is designated BP17. BP17 is a mutant thermostable phytase derived from a wild-type phytase from *Buttiauxella* sp (Miasnikov et al., International Publication No. WO 2006/043178). The amino acid sequence of the mature protein of BP-17 is shown in FIG. 4*b*:

The BP-17 coding sequence (SEQ ID NO:5) was fused to an NSP24 aspartic protease signal peptide (SEQ ID NO:4) and placed under the control of *T. reesei* cbhI promoter and transcription terminator in expression vector pTrex3g. The structure of this vector is illustrated in FIG. 4. A 5.85 kb XbaI-XbaI fragment of pTrex3g comprising the expression cassette and a selectable marker (amdS gene from *Aspergillus nidulans*) was purified by agarose gel electrophoresis and used to transform the recombinant *T. reesei* Y5 strain GICC 2984 by the procedure described in Example 1 using 16 kV/cm voltage. Transformant colonies appeared in a period between 4 days to about 1 week after plating. Individual transformants were transferred onto fresh acetamide selective plates and grown for 3-4 days. Most isolates showed stable growth on selective medium. The clones (38) were used to inoculate 5 ml of lactose defined medium (Foreman et al., International Publication No. WO 2005/001036) in 20×175 mm test tubes. The tubes were fixed in a rotary shaker at about 45° angle and shaken at 200 rpm and 28° C. for 4-5 days.

Example 3

Analysis of Phytase Gene Expression in *T. reesei* Transformants

The culture medium of the transformants obtained and cultivated as described in Example 2 was separated from mycelium by centrifugation (16000×G, 10 min) and analyzed by acrylamide gel electrophoresis in the presence of sodium dodecyl sulfate (SDS PAGE). The results of a typical experiment are that about ⅔ of all studied transformants (24 out of 38) expressed the phytase gene at levels easily detectable by SDS PAGE. The expression levels of phytase varied largely between clones. To obtain a more quantitative estimate of the variability of phytase/xylanase ratios in different clones, enzymatic activities were determined in a set of transformants chosen to represent the whole spectrum of phytase expression levels.

Phytase assays were carried out using as a substrate 7.5 mM phytase in 100 mM sodium acetate buffer, containing 1 mg/ml BSA at a final pH 5.0. The culture supernatants (20 μl, diluted 1:80 and 1:160), were mixed with 100 □l of the substrate solution and incubated for 90 min at 25° C. The reaction was quenched by addition of 100 μl of a freshly made solution containing 1 part of 10% ammonium molybdate, 1 part of 0.24% ammonium vanadate and 2 parts of 20% nitric acid. After centrifugation (16000×G for 10 min), 200 μl of supernatant from each reaction was transferred into a well of a microtitre plate and the absorbance at 405 nm was recorded. The difference in absorbance between the experimental and control samples (containing water instead of the enzyme solution) was taken as the measure of enzymatic activity.

Xylanase was assayed as follows. Ten tablets from a Xylazyme AX assay kit (Megazyme) were dispersed in 15 ml of 100 mM NaOAc buffer containing 1 mg/ml BSA to make the substrate suspension. The pH was adjusted to 5.0 and 10 μl of the culture supernatants diluted to an appropriate concentration so that the assay was in the linear range (1:80 and 1:160). They were reacted with 250 μl of the substrate suspension for 90 min at 25° C. The reaction was quenched by addition of 2500 of 1M Na$_2$CO$_3$. After centrifugation of the reaction mixtures (16000×G for 10 min), 100 μl of the supernatant from each reaction was transferred into a well of a microtitre plate and the absorbance at 595 nm was measured. The difference in absorbance between the experimental and control samples (containing water instead of the enzyme solution) was taken as the measure of enzymatic activity.

The results of the determination of phytase and xylanase activity in 8 different clones are summarized in Table 2. This data, in accordance with the results of electrophoretic analysis indicates that the ratios of the two enzymatic activities in different transformants vary over a broad range.

TABLE 2

Phytase and xylanase activity in a representative set of transformants

| Clone number | Phytase activity, arbitrary units | Xylanase activity, arbitrary units | Phytase/xylanase Ratio |
|---|---|---|---|
| 5 | 0.27 | 0.57 | 0.47 |
| 10 | 1.21 | 0.31 | 3.87 |
| 22 | 0.31 | 0.24 | 1.28 |
| 25 | 0.53 | 0.22 | 2.43 |
| 26 | 0.17 | 0.34 | 0.51 |
| 27 | 0.23 | 0.42 | 0.55 |
| 31 | 0.23 | 0.47 | 0.50 |
| 32 | 0.72 | 0.57 | 1.27 |

Example 4

Construction of Expression Vector pKB408 (NSP24 Signal Peptide) and pKB410 (CBH1 Signal Peptide)

Figure 6A:
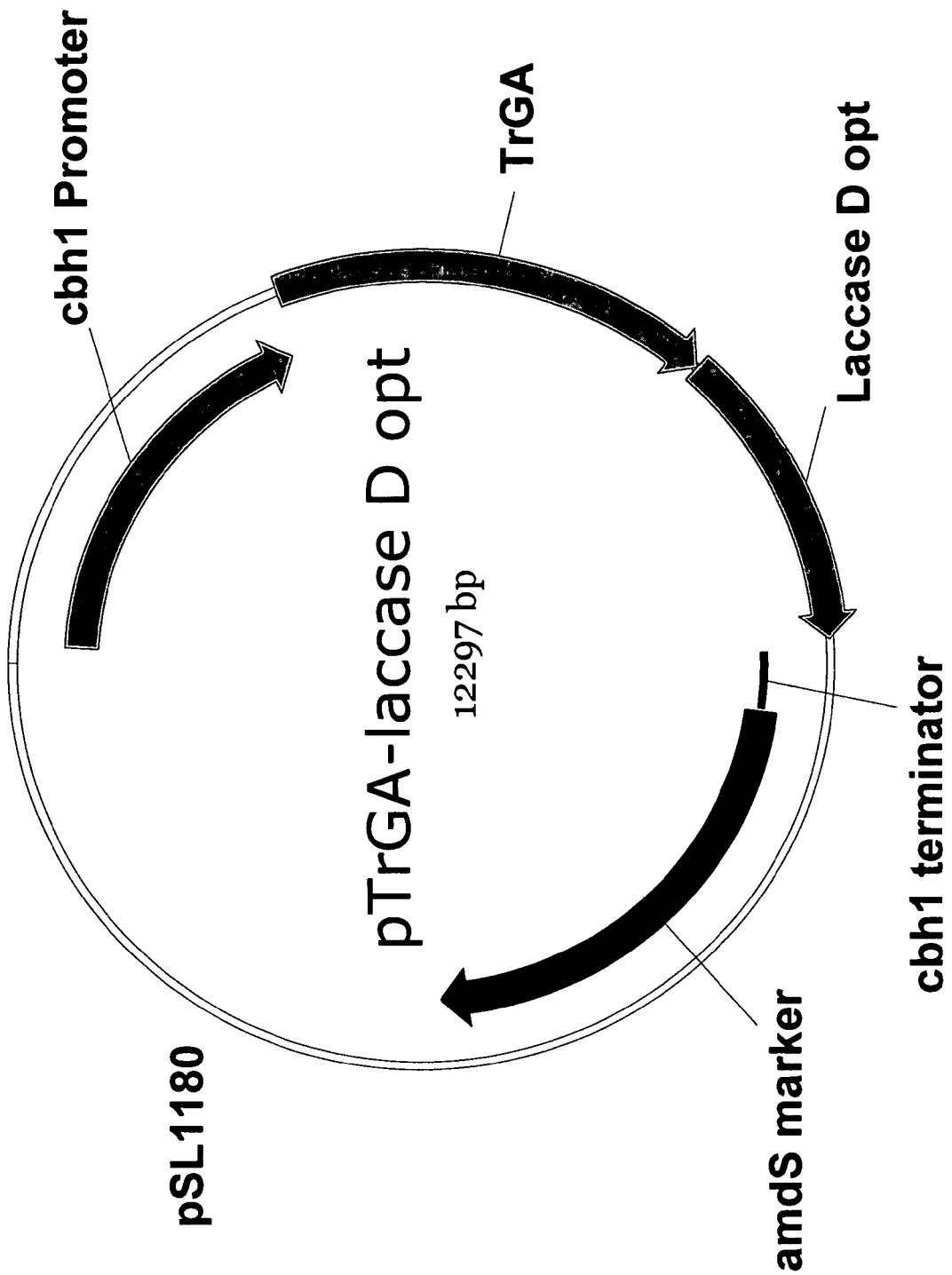
Figure 7A:
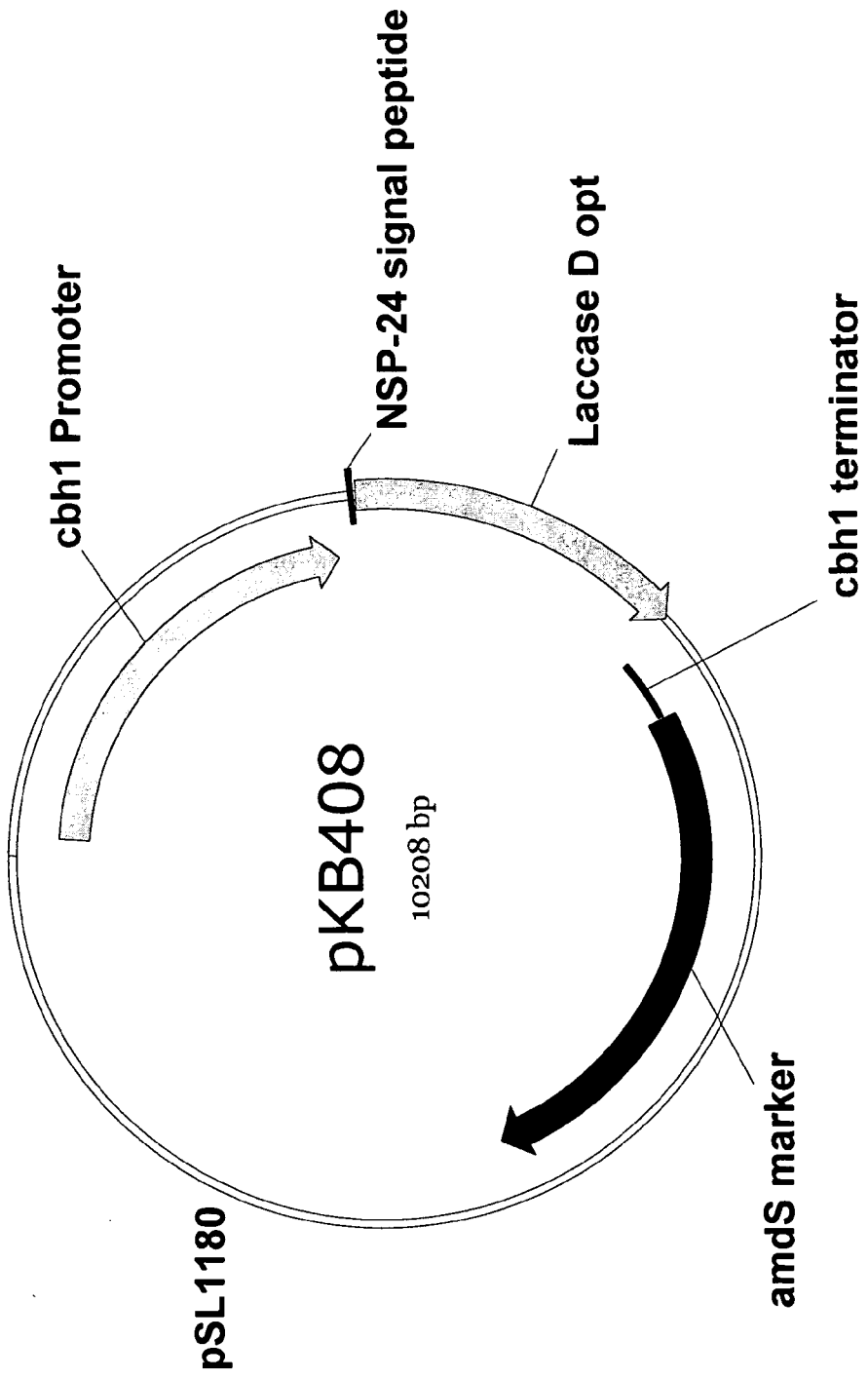

The pKB408 plasmid was produced from pTrex 4 laccase optD to express *C. unicolor* laccase D opt (SEQ ID NO:6) operably fused to the *T. reesei* NSP24 signal peptide. The plasmid was constructed similarly to that shown in FIG. 6a (pTrex4-laccaseD opt) except that the laccase D constructs were operably linked to the NSP24 signal peptide, which was inserted in place of the laccase D opt linked to the CBH1 signal sequence, catalytic domain and linker. FIGS. 7a and b provide the schematic and the polynucleotide sequence of the *Trichoderma* expression plasmid pKB408 (SEQ ID NO:7), respectively.

Figure 8A:
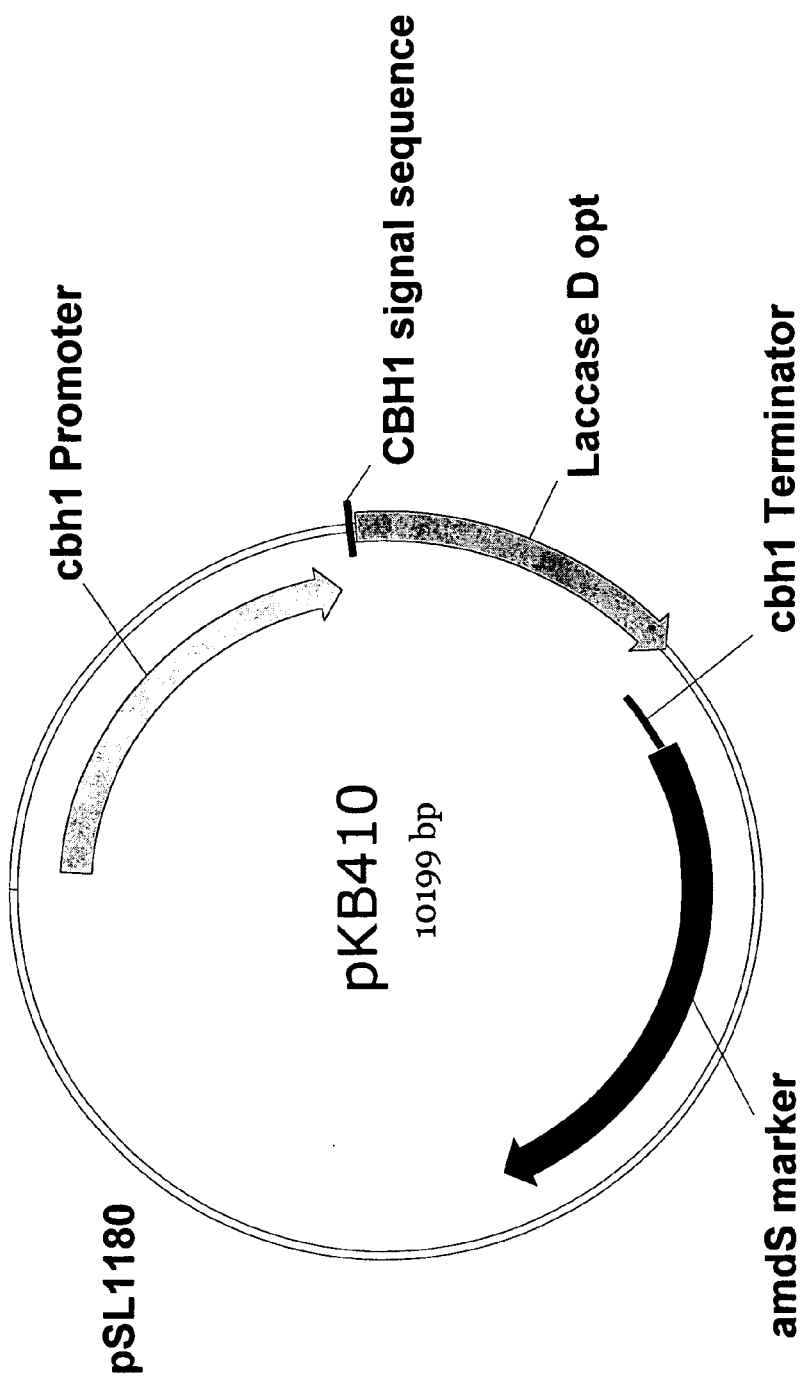

The pKB410 plasmid was produced similarly, except the *T. reesei* CHB1 signal sequence was used instead of the NSP24 signal sequence. FIGS. 8a and b provide the schematic and the polynucleotide sequence of the *Trichoderma* expression plasmid pKB410 (SEQ ID NO:8), respectively.

pTrex4-laccaseD contained the laccase D codon optimized gene fused to the CBH1 (cellobiohydrolase) core/linker and expressed from the CBH1 promoter. FIG. 6a provides a schematic of the *Trichoderma* expression plasmid and FIG. 6b provides the sequence of the pTrex4-laccaseD opt plasmid (SEQ ID NO:6). The following segments of DNA were assembled in the construction of pTrex4-laccase D opt (See, FIG. 6a). A fragment of *T. reesei* genomic DNA representing the CBH1 promoter and the CBH1 signal sequence and CBH1 core/linker was inserted into the plasmid pSL1180 vector. A codon optimized copy of the *C. unicolor* laccase D (laccase D opt) gene was inserted, such that it was operably linked to the CBH1 at its linker region. A CBH1 terminator from *T. reesei* was operably linked to the laccase D gene. The amdS gene was added as a selectable autotropic marker. The bla gene (encoding beta-lactamase, a selective marker obtained from *E. coli*) is present in the pSL1180 vector. The sequence of the plasmid is provided as FIG. 6b (SEQ ID NO:6).

Example 5

Transformation of *T. reesei* and Analysis of Expression

In this example, the stable recombinant *T. reesei* strain derived from RL-P37 (See, Sheir-Neiss and Montenecourt, Appl. Microbiol. Biotechnol., 20:46-53 [1984]) and deleted for the cbh1, cbh2, egl1, and egl2 genes described by Bower et al (See, Bower et al., *Carbohydrases From Trichoderma reesei and Other Micro-organisms*, Royal Society of Chemistry, Cambridge, pp. 327-334 [1998]) was used for transforming the plasmids from Example 4. Biolistic and electroporation methods were used to transform the plasmids, as described below.

Biolistic Transformation:

The expression plasmid was confirmed by DNA sequencing and transformed biolistically into a *Trichoderma* strain. Transformation of the *Trichoderma* strain by the biolistic transformation method was accomplished using a Biolistic® PDS-1000/he Particle Delivery System (Bio-Rad) following the manufacturer's instructions (See, WO 05/001036 and US Pat. Appl. Publ. No. 2006/0003408). Transformants were selected and transferred onto minimal media with acetamide (MMA) plates and grown for 4 days at 30° C. A small plug of a single colony including spores and mycelium was transferred into 30 mls of NREL lactose defined broth (pH 6.2) containing 1 mM copper. The cultures were grown for 5 days at 30° C. Culture broths were centrifuged and supernatants were analyzed using the ABTS assay as described below for laccase activity.

Electroporation

Electroporation was performed as described in Method for Introducing Nucleic acids into Fungal Cells, Patent application No. 60/931,072, filed May 21, 2007, herein incorporated by reference in its entirety. A *T. reesei* strain was grown and sporulated on Potato Dextrose Agar plates (Difco) for about 10-20 days. The spores were washed from the surface of the plates with water and purified by filtration through Miracloth (Calbiochem). The spores were collected by centrifugation (3000×g, 12 min), washed once with ice-cold water and once with ice-cold 1.1M sorbitol. The spore pellet was re-suspended in a small volume of cold 1.1 M sorbitol, mixed with about 8 □g of gel-purified DNA fragment isolated from plasmid DNA (pKB408 and pKB410, FIGS. 6a and 7a) per 100 μl of spore suspension. The mixture (100 μl) was placed into an electroporation cuvette (1 mm gap) and subjected to an electric pulse using the following electroporation parameters: voltage 6000-20000 V/cm, capacitance=25 μF, resistance=50Ω After electroporation, the spores were diluted about 100-fold into 5:1 mixture of 1.1 M sorbitol and YEPD (1% yeast extract, 2% Bacto-peptone, 2% glucose, pH 5.5), placed in shake flasks and incubated for 16-18 hours in an orbital shaker (28° C. and 200 rpm). The spores were once again collected by centrifugation, re-suspended in about 10-fold of pellet volume of 1.1 M sorbitol and plated onto two 15 cm Petri plates containing amdS modified medium (acetamide 0.6 g/l, cesium chloride 1.68 WI, glucose 20 g/l, potassium dihydrogen phosphate 15 g/l, magnesium sulfate heptahydrate 0.6 g/l, calcium chloride dihydrate 0.6 g/l, iron (II) sulfate 5 mg/l, zinc sulfate 1.4 mg/l, cobalt (II) chloride 1 mg/l, manganese (II) sulfate 1.6 mg/l, agar 20 g/l and pH 4.25). Transformants appeared at about 1 week of incubation at 28-30° C.

The ABTS assay was performed as follows: An ABTS stock solution was prepared containing 4.5 mM ABTS in water (ABTS; Sigma Cat# A-1888). Buffer was prepared containing 0.1 M sodium acetate pH 5.0. Then, 1.5 ml of buffer and 0.2 ml of ABTS stock solution were added to cuvettes (10×4×45 mm, No./REF67.742) and mixed well. One extra cuvette was prepared as a blank. Then, 50 ul of each enzyme sample to be tested (using various dilutions) were added to the mixtures.

The ABTS activity was measured in a Genesys2 machine (Spectronic) using an ABTS kinetic assay program set up: (Advanced Kinetics) as follows: wave length 420 nm, interval time (Sec) 2.0, total run time (sec) 14.0, factor 1.000, low limit −000000.00, high limit 999999.00, and the reaction order was first.

The procedure involved adding 1.5 mL of NaOAc (120 mM NaOAc Buffer pH 5.0), then add 0.2 mL of ABTS (4.5 mM ABTS), to the cuvette, then to blank the cuvette, adding 0.05 mL of the enzyme sample to the cuvette, mixing quickly and well and, finally, measuring the change of absorption at 420 nm, every 2 seconds for 14 seconds. One ABTS unit is defined as change of A420 per minute (given no dilution to the sample). Calculation of ABTS U/mL: (chance in Δ420/min*dilution factor).

Example 6

Analysis of Laccase Production Using NSP24 and CBH1 Signal Sequences

When the *T. reesei* CBH1 signal sequence was operably linked to the laccase gene expression was improved 4-5 fold over the initial CBH1 fusion strain alone in shake flasks and 5-6 fold in a 14 liter fermentor (data not shown). When the *T. reesei* NSP24 signal sequence was used, the expression improved 3-4 fold in shake flasks and 4-5 fold in a 14 liter fermentor. Three clones were analyzed in the shake flasks for the CBH1 signal sequence) and two clones were analyzed for the NSP24 signal sequence and the expression was analyzed at 3 days, 4 days and 5 days. A single clone of each was analyzed in the 14 liter fermentors.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All publications and patents cited herein are incorporated by reference.

We claim:

1. A fusion protein comprising an isolated signal peptide comprising SEQ ID NO:4 or a variant thereof having at least 90% identity to SEQ ID NO:4 operably linked to a heterologous protein.

2. The fusion protein of claim 1, wherein the heterologous protein is chosen from: a phytase, a glucoamylase, an alpha amylase, a granular starch hydrolyzing enzyme, a cellulase, a lipase, a xylanase, a cutinase, a hemicellulase, a protease, an oxidase, or a laccase.

3. The fusion protein of claim 2, wherein the heterologous protein is a phytase having at least 90% sequence identity to SEQ ID NO:5.

4. An isolated polynucleotide comprising a polynucleotide encoding the fusion protein of claim 1.

5. An expression vector comprising a polynucleotide encoding the fusion protein of claim 1.

6. The expression vector of claim 5, further comprising a promoter.

7. A host cell comprising the expression vector of claim 5.

8. The host cell of claim 7, wherein the host cell is a fungal or bacterial cell.

9. The host cell of claim 8, wherein the bacterial cell is a *Streptomyces* or *Bacillus* cell.

10. The host cell of claim 8, wherein the fungal cell is a filamentous fungal cell.

11. The host cell of claim 10, wherein the filamentous fungal cell is an *Aspergillus* spp. a *Fusarium* spp. or *Trichoderma* spp.

12. The host cell of claim 11, wherein the *Aspergillus* is *A. niger, A. oryzae, A. nidulans,* or *A. awamori*.

13. The host cell of claim 11, wherein the *Trichoderma* is *T. reesei*.

14. The host cell of claim 7, wherein the expression vector is stably integrated into the genome of the host cell.

15. A method of producing a heterologous protein in a host cell, comprising:
providing the expression vector of claim 5;
transforming a host cell with the expression vector; and
culturing the host cell, under conditions such that the heterologous protein is expressed and secreted from the host cell.

16. The method of claim 15, wherein the host cell is a filamentous fungal host cell.

17. The method of claim 15, wherein the filamentous fungal host cell is a *Trichoderma* or *Aspergillus* cell.

18. A method for producing a heterologous protein in a host cell, comprising introducing into a host cell a polynucleotide encoding a signal peptide comprising SEQ ID NO:4 or a variant thereof having at least 90% identity to SEQ ID NO:4 operably linked to a heterologous protein into the host cell, culturing the host cell under suitable culture conditions for the expression and production of the heterologous protein, and
producing said heterologous protein.

19. The method according to claim 18 further comprising recovering the produced heterologous protein.

20. The method according to claim 18, wherein the host cell is a fungal cell.

21. The method according to claim 20, wherein the fungal cell is a filamentous fungal cell.

22. The method according to claim 18, wherein the heterologous protein is chosen from a phytase, a glucoamylase, an alpha amylase, a granular starch hydrolyzing enzyme, a cellulase, a lipase, a xylanase, a cutinase, a hemicellulase, a protease, an oxidase, or a laccase.

23. A DNA construct for use in transforming a filamentous fungal cell to enable secretion of a protein of interest, said DNA construct comprising a promoter from a fungal gene operably linked to a polynucleotide encoding a signal peptide and a protein of interest wherein said signal peptide has the sequence of SEQ ID NO:4 and said protein of interest is chosen from a phytase, a glucoamylase, an alpha amylase, a granular starch hydrolyzing enzyme, a cellulase, a lipase, a xylanase, a cutinase, a hemicellulase, a protease, an oxidase, or a laccase.

24. The DNA construct of claim 23, wherein the protein of interest is a phytase having at least 90% sequence identity to SEQ ID NO:5.

* * * * *

SEQUENCE LISTING

<160> NUMBER OF SEQ ID NOS: 8

<210> SEQ ID NO 1
<211> LENGTH: 1302
<212> TYPE: DNA
<213> ORGANISM: Trichoderma reesei

<400> SEQUENCE: 1

```
atgcagacct ttggagcttt tctcgtttcc ttcctcgccg ccagcggcct ggccgcggcc      60
ctccccaccg agggtcagaa gacggcttcc gtcgaggtcc agtacaacaa gaactacgtc     120
ccccacggcc ctactgctct cttcaaggcc aagagaaagt atggcgctcc catcagcgac     180
aacctgaagt ctctcgtggc tgccaggcag gccaagcagg ctctcgccaa gcgccagacc     240
ggctcggcgc ccaaccaccc cagtgacagc gccgattcgg agtacatcac ctccgtctcc     300
atcggcactc cggctcaggt cctcccctg gactttgaca ccggctcctc cgacctgtgg     360
gtctttagct ccgagacgcc caagtcttcg gccaccggcc acgccatcta cacgccctcc     420
aagtcgtcca cctccaagaa ggtgtctggc gccagctggt ccatcagcta cggcgacggc     480
agcagctcca gcggcgatgt ctacaccgac aaggtcacca tcggaggctt cagcgtcaac     540 acccaggcg tcgagtctgc cacccgcgtg tccaccgagt tcgtccagga cacggtcatc     600
tctggcctcg tcggccttgc ctttgacagc ggcaaccagg tcaggccgca cccgcagaag     660
acgtggttct ccaacgccgc cagcagcctg gctgagcccc ttttcactgc cgacctgagg     720
cacggacaga gtaagtagac actcactgga attcgttcct ttcccgatca tcatgaaagc     780
aagtagactg actgaaccaa acaactagac ggcagctaca actttggcta catcgacacc     840
agcgtcgcca agggcccccgt tgcctacacc cccgttgaca acagccaggg cttctgggag     900
ttcactgcct cgggctactc tgtcggcggc ggcaagctca accgcaactc catcgacggc     960
attgccgaca ccggcaccac cctgctcctc ctcgacgaca acgtcgtcga tgcctactac    1020
gccaacgtcc agtcggccca gtacgacaac cagcaggagg gtgtcgtctt cgactgcgac    1080
gaggacctcc cttcgttcag cttcggtgtt ggaagctcca ccatcaccat ccctggcgat    1140
ctgctgaacc tgactcccct cgaggagggc agctccacct gcttcggtgg cctccagagc    1200
```

```
agctccggca ttggcatcaa catctttggt gacgttgccc tcaaggctgc cctggttgtc    1260
tttgacctcg gcaacgagcg cctgggctgg gctcagaaat aa                       1302
```

<210> SEQ ID NO 2
<211> LENGTH: 407
<212> TYPE: PRT
<213> ORGANISM: Trichoderma reesei

<400> SEQUENCE: 2

```
Met Gln Thr Phe Gly Ala Phe Leu Val Ser Phe Leu Ala Ala Ser Gly
1               5                   10                  15

Leu Ala Ala Ala Leu Pro Thr Glu Gly Gln Lys Thr Ala Ser Val Glu
            20                  25                  30

Val Gln Tyr Asn Lys Asn Tyr Val Pro His Gly Pro Thr Ala Leu Phe
        35                  40                  45

Lys Ala Lys Arg Lys Tyr Gly Ala Pro Ile Ser Asp Asn Leu Lys Ser
    50                  55                  60

Leu Val Ala Ala Arg Gln Ala Lys Gln Ala Leu Ala Lys Arg Gln Thr
65                  70                  75                  80

Gly Ser Ala Pro Asn His Pro Ser Asp Ser Ala Asp Ser Glu Tyr Ile
                85                  90                  95

Thr Ser Val Ser Ile Gly Thr Pro Ala Gln Val Leu Pro Leu Asp Phe
            100                 105                 110

Asp Thr Gly Ser Ser Asp Leu Trp Val Phe Ser Ser Glu Thr Pro Lys
        115                 120                 125

Ser Ser Ala Thr Gly His Ala Ile Tyr Thr Pro Ser Lys Ser Ser Thr
    130                 135                 140

Ser Lys Lys Val Ser Gly Ala Ser Trp Ser Ile Ser Tyr Gly Asp Gly
145                 150                 155                 160

Ser Ser Ser Ser Gly Asp Val Tyr Thr Asp Lys Val Thr Ile Gly Gly
                165                 170                 175

Phe Ser Val Asn Thr Gln Gly Val Glu Ser Ala Thr Arg Val Ser Thr
            180                 185                 190

Glu Phe Val Gln Asp Thr Val Ile Ser Gly Leu Val Gly Leu Ala Phe
        195                 200                 205

Asp Ser Gly Asn Gln Val Arg Pro His Pro Gln Lys Thr Trp Phe Ser
    210                 215                 220

Asn Ala Ala Ser Ser Leu Ala Glu Pro Leu Phe Thr Ala Asp Leu Arg
225                 230                 235                 240

His Gly Gln Asn Gly Ser Tyr Asn Phe Gly Tyr Ile Asp Thr Ser Val
                245                 250                 255

Ala Lys Gly Pro Val Ala Tyr Thr Pro Val Asp Asn Ser Gln Gly Phe
            260                 265                 270

Trp Glu Phe Thr Ala Ser Gly Tyr Ser Val Gly Gly Gly Lys Leu Asn
        275                 280                 285

Arg Asn Ser Ile Asp Gly Ile Ala Asp Thr Gly Thr Thr Leu Leu Leu
    290                 295                 300

Leu Asp Asp Asn Val Val Asp Ala Tyr Tyr Ala Asn Val Gln Ser Ala
305                 310                 315                 320

Gln Tyr Asp Asn Gln Gln Glu Gly Val Val Phe Asp Cys Asp Glu Asp
                325                 330                 335

Leu Pro Ser Phe Ser Phe Gly Val Gly Ser Ser Thr Ile Thr Ile Pro
            340                 345                 350

Gly Asp Leu Leu Asn Leu Thr Pro Leu Glu Glu Gly Ser Ser Thr Cys
```

```
                355                 360                 365
Phe Gly Gly Leu Gln Ser Ser Ser Gly Ile Gly Ile Asn Ile Phe Gly
370                 375                 380

Asp Val Ala Leu Lys Ala Ala Leu Val Val Phe Asp Leu Gly Asn Glu
385                 390                 395                 400

Arg Leu Gly Trp Ala Gln Lys
                405

<210> SEQ ID NO 3
<211> LENGTH: 355
<212> TYPE: PRT
<213> ORGANISM: Trichoderma reesei

<400> SEQUENCE: 3

Lys Tyr Gly Ala Pro Ile Ser Asp Asn Leu Lys Ser Leu Val Ala Ala
1               5                   10                  15

Arg Gln Ala Lys Gln Ala Leu Ala Lys Arg Gln Thr Gly Ser Ala Pro
            20                  25                  30

Asn His Pro Ser Asp Ser Ala Asp Ser Glu Tyr Ile Thr Ser Val Ser
        35                  40                  45

Ile Gly Thr Pro Ala Gln Val Leu Pro Leu Asp Phe Asp Thr Gly Ser
    50                  55                  60

Ser Asp Leu Trp Val Phe Ser Ser Glu Thr Pro Lys Ser Ser Ala Thr
65                  70                  75                  80

Gly His Ala Ile Tyr Thr Pro Ser Lys Ser Ser Thr Ser Lys Lys Val
                85                  90                  95

Ser Gly Ala Ser Trp Ser Ile Ser Tyr Gly Asp Gly Ser Ser Ser Ser
            100                 105                 110

Gly Asp Val Tyr Thr Asp Lys Val Thr Ile Gly Gly Phe Ser Val Asn
        115                 120                 125

Thr Gln Gly Val Glu Ser Ala Thr Arg Val Ser Thr Glu Phe Val Gln
    130                 135                 140

Asp Thr Val Ile Ser Gly Leu Val Gly Leu Ala Phe Asp Ser Gly Asn
145                 150                 155                 160

Gln Val Arg Pro His Pro Gln Lys Thr Trp Phe Ser Asn Ala Ala Ser
                165                 170                 175

Ser Leu Ala Glu Pro Leu Phe Thr Ala Asp Leu Arg His Gly Gln Asn
            180                 185                 190

Gly Ser Tyr Asn Phe Gly Tyr Ile Asp Thr Ser Val Ala Lys Gly Pro
        195                 200                 205

Val Ala Tyr Thr Pro Val Asp Asn Ser Gln Gly Phe Trp Glu Phe Thr
    210                 215                 220

Ala Ser Gly Tyr Ser Val Gly Gly Lys Leu Asn Arg Asn Ser Ile
225                 230                 235                 240

Asp Gly Ile Ala Asp Thr Gly Thr Thr Leu Leu Leu Leu Asp Asp Asn
                245                 250                 255

Val Val Asp Ala Tyr Tyr Ala Asn Val Gln Ser Ala Gln Tyr Asp Asn
            260                 265                 270

Gln Gln Glu Gly Val Val Phe Asp Cys Asp Glu Asp Leu Pro Ser Phe
        275                 280                 285

Ser Phe Gly Val Gly Ser Ser Thr Ile Thr Ile Pro Gly Asp Leu Leu
    290                 295                 300

Asn Leu Thr Pro Leu Glu Glu Gly Ser Ser Thr Cys Phe Gly Gly Leu
305                 310                 315                 320

Gln Ser Ser Ser Gly Ile Gly Ile Asn Ile Phe Gly Asp Val Ala Leu
```

```
                        325                 330                 335
Lys Ala Ala Leu Val Val Phe Asp Leu Gly Asn Glu Arg Leu Gly Trp
                340                 345                 350

Ala Gln Lys
        355

<210> SEQ ID NO 4
<211> LENGTH: 20
<212> TYPE: PRT
<213> ORGANISM: Trichoderma reesei

<400> SEQUENCE: 4

Met Gln Thr Phe Gly Ala Phe Leu Val Ser Phe Leu Ala Ala Ser Gly
1               5                   10                  15

Leu Ala Ala Ala
        20

<210> SEQ ID NO 5
<211> LENGTH: 413
<212> TYPE: PRT
<213> ORGANISM: Buttiauxella sp.

<400> SEQUENCE: 5

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gly Ile Leu Ser Gln Gly Ser Cys Pro
65              70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Gln Val Gln Gln
130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
            260                 265                 270
```

```
Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
        290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
            405                 410
```

<210> SEQ ID NO 6
<211> LENGTH: 11689
<212> TYPE: DNA
<213> ORGANISM: Artificial
<220> FEATURE:
<223> OTHER INFORMATION: synthetic expression plasmid

<400> SEQUENCE: 6

```
aagcgcctgc agccacttgc agtcccgtgg aattctcacg gtgaatgtag gccttttgta      60
gggtaggaat tgtcactcaa gcaccccaa cctccattac gcctccccca tagagttccc     120
aatcagtgag tcatggcact gttctcaaat agattgggga gaagttgact tccgcccaga    180
gctgaaggtc gcacaaccgc atgatatagg gtcggcaacg gcaaaaaagc acgtggctca    240
ccgaaaagca agatgtttgc gatctaacat ccaggaacct ggatacatcc atcatcacgc    300
acgaccactt tgatctgctg gtaaactcgt attcgcccta accgaagtg acgtggtaaa     360
tctacacgtg ggccccttc ggtatactgc gtgtgtcttc tctaggtgcc attcttttcc     420
cttcctctag tgttgaattg tttgtgttgg agtccgagct gtaactacct ctgaatctct    480
ggagaatggt ggactaacga ctaccgtgca cctgcatcat gtatataata gtgatcctga    540
gaagggggt ttggagcaat gtgggacttt gatggtcatc aaacaaagaa cgaagacgcc      600
tcttttgcaa agttttgttt cggctacggt gaagaactgg atacttgttg tgtcttctgt    660
gtattttgt ggcaacaaga ggccagagac aatctattca acaccaagc ttgctctttt      720
gagctacaag aacctgtggg gtatatatct agagttgtga agtcggtaat cccgctgtat    780
agtaatacga gtcgcatcta aatactccga gctgctgcg aacccggaga tcgagatgt      840
gctggaaagc ttctagcgag cggctaaatt agcatgaaag gctatgagaa attctggaga    900
cggcttgttg aatcatggcg ttccattctt cgacaagcaa agcgttccgt cgcagtagca    960
ggcactcatt cccgaaaaaa ctcggagatt cctaagtagc gatggaaccg gaataatata   1020
ataggcaata cattgagttg cctcgacggt tgcaatgcag gggtactgag cttggacata   1080
actgttccgt accccacctc ttctcaacct ttggcgtttc cctgattcag cgtacccgta   1140
caagtcgtaa tcactattaa cccagactga ccggacgtgt tttgcccttc atttggagaa   1200
ataatgtcat tgcgatgtgt aatttgcctg cttaccgac tggggctgtt cgaagcccga    1260
```

```
atgtaggatt gttatccgaa ctctgctcgt agaggcatgt tgtgaatctg tgtcgggcag    1320
gacacgcctc gaaggttcac ggcaagggaa accaccgata gcagtgtcta gtagcaacct    1380
gtaaagccgc aatgcagcat cactggaaaa tacaaaccaa tggctaaaag tacataagtt    1440
aatgcctaaa gaagtcatat accagcggct aataattgta caatcaagtg ctaaacgta     1500 ccgtaatttg ccaacggctt gtggggttgc agaagcaacg gcaaagcccc acttccccac    1560
gtttgtttct tcactcagtc caatctcagc tggtgatccc ccaattgggt cgcttgtttg    1620
ttccggtgaa gtgaaagaag acagaggtaa gaatgtctga ctcggagcgt tttgcataca    1680
accaagggca gtgatggaag acagtgaaat gttgacattc aaggagtatt tagccaggga    1740
tgcttgagtg tatcgtgtaa ggaggtttgt ctgccgatac gacgaatact gtatagtcac    1800
ttctgatgaa gtggtccata ttgaaatgta agtcggcact gaacaggcaa agattgagt     1860 tgaaactgcc taagatctcg ggccctcggg ccttcggcct ttgggtgtac atgtttgtgc    1920
tccgggcaaa tgcaaagtgt ggtaggatcg aacacactgc tgcctttacc aagcagctga    1980
gggtatgtga taggcaaatg ttcaggggcc actgcatggt ttcgaataga agagaagct     2040 tagccaagaa caatagccga taaagatagc ctcattaaac ggaatgagct agtaggcaaa    2100
gtcagcgaat gtgtatatat aaaggttcga ggtccgtgcc tccctcatgc tctccccatc    2160
tactcatcaa ctcagatcct ccaggagact tgtacaccat cttttgaggc acagaaaccc    2220
aatagtcaac cgcggactgc gcatcatgta tcggaagttg gccgtcatct cggccttctt    2280
ggccacagct cgtgctcagt cggcctgcac tctccaatcg gagactcacc cgcctctgac    2340
atggcagaaa tgctcgtctg gtggcacttg cactcaacag acaggctccg tggtcatcga    2400
cgccaactgg cgctggactc acgctacgaa cagcagcacg aactgctacg atggcaacac    2460
ttggagctcg accctatgtc ctgacaacga gacctgcgcg aagaactgct gtctggacgg    2520
tgccgcctac cgtccacgt acggagttac cacgagcggt aacagcctct ccattggctt     2580
tgtcacccag tctgcgcaga gaacgttgg cgctcgcctt taccttatgg cgagcgacac     2640
gacctaccag gaattcaccc tgcttggcaa cgagttctct ttcgatgttg atgtttcgca    2700
gctgccgtaa gtgacttacc atgaaccccct gacgtatctt cttgtgggct cccagctgac    2760
tggccaattt aaggtgcggc ttgaacggag ctctctactt cgtgtccatg gacgcggatg    2820
gtggcgtgag caagtatccc accaacaccg ctggcgccaa gtacggcacg ggtactgtg    2880 acagccagtg tccccgcgat ctgaagttca tcaatggcca ggccaacgtt gagggctggg    2940
agccgtcatc caacaacgca aacacgggca ttggaggaca cggaagctgc tgtctctgaga   3000 tggatatctg ggaggccaac tccatctccg aggctcttac ccccaccct tgcacgactg     3060 tcggccagga gatctgcgag ggtgatgggt cggcggaac ttactccgat aacagatatg     3120
gcggcacttg cgatcccgat ggctgcgact ggaacccata ccgcctgggc aacaccagct    3180
tctacggccc tggctcaagc tttaccctcg ataccaccaa gaaattgacc gttgtcaccc    3240
agttcgagac gtcgggtgcc atcaaccgat actatgtcca gaatggcgtc actttccagc    3300
agcccaacgc cgagcttggt agttactctg gcaacgagct caacgatgat tactgcacag    3360
ctgaggaggc agaattcggc ggatcctctt tctcagacaa gggcggcctg actcagttca    3420
agaaggctac ctctggcggc atggttctgg tcatgagtct gtgggatgat gtgagtttga    3480
tggacaaaca tgcgcgttga caaagagtca agcagctgac tgagatgtta cagtactacg    3540
ccaacatgct gtggctggac tccacctacc gacaaacga gacctcctcc acacccggtg     3600
ccgtgcgcgg aagctgctcc accagctccg gtgtccctgc tcaggtcgaa tctcagtctc    3660
```

```
ccaacgccaa ggtcaccttc tccaacatca agttcggacc cattggcagc accggcaacc   3720
ctagcggcgg caaccctccc ggcggaaacc cgcctggcac caccaccacc cgccgcccag   3780
ccactaccac tggaagctct cccggaccta ctagtgtcgc cgtttacaaa cgcgctattg   3840
gaccagttgc tgatctgcac atcgttaaca aggatttggc cccagacggc gtccagcgcc   3900
caactgttct ggccggtgga acttttccgg gcacgctgat taccggtcaa aagggcgaca   3960
acttccagct gaacgtgatt gatgacctga ccgacgatcg catgttgacc cctacttcga   4020
tccattggca tggtttcttc cagaagggaa ccgcctgggc cgacggtccg gctttcgtta   4080
cacagtgccc tattatcgca gacaactcct cctctacga tttcgacgtt cccgaccagg   4140
cgggcacctt ctggtaccac tcacacttgt ctacacagta ctgcgacggt ctgcgcggtg   4200
ccttcgttgt ttacgacccc aacgaccctc acaaggacct ttatgatgtc gatgacggtg   4260
gcacagttat cacattggct gactggtatc acgtcctcgc tcagaccgtt gtcggagctg   4320
ctacacccga ctctacgctg attaacggct gggacgcag ccagactggc cccgccgacg   4380
ctgagctggc cgttatctct gttgaacaca acaagagata ccgtttcaga ctcgtctcca   4440
tctcgtgcga tcccaacttc acttttagcg tcgacggtca caacatgacg gttatcgagg   4500
ttgatggcgt gaatacccgc cctctcaccg tcgattccat tcaaattttc gccggccagc   4560
gatactcctt tgtgctgaat gccaatcagc ccgaggataa ctactggatc cgcgctatgc   4620
ctaacatcgg acgaaacacc actacccttg atggcaagaa tgccgctatc ctgcgataca   4680
agaacgccag cgttgaggag cccaaaaccg tcggaggacc cgcgcagagc ccattgaacg   4740
aggccgacct gcgacctctg gtgcccgctc ctgtccctgg caacgcagtt cctggtggtg   4800
cggacatcaa ccaccgcctg aacctgacat tcagcaacgg cctcttctct atcaataacg   4860
catcatttac aaacccccagc gtccctgcct tgttgcagat tctttccggc gcacaaaacg   4920
ctcaggatct gcttcccacc ggttcttata tcggcttgga gttgggcaag gtcgttgaac   4980
tcgtgatccc tcccttggcc gttggtggcc cccatccatt ccacttgcac ggccacaact   5040
tttgggtcgt ccgaagcgct ggttctgacg agtataattt cgacgatgca attttgcgcg   5100
acgtggtcag cattggcgcg ggaactgacg aggttactat ccgttttgtc actgataacc   5160
caggcccttg gttcctccat tgccacatcg actggcacct cgaagccggc ctcgccattg   5220
ttttcgccga aggcatcaat caaaccgcag ccgccaaccc gactccacag gcctgggacg   5280
aactctgccc caagtataac ggactctccg cttcccagaa agtgaagccc aagaagggaa   5340
cagccatcta aggcgcgccg cgcgccagct ccgtgcgaaa gcctgacgca ccggtagatt   5400
cttggtgagc ccgtatcatg acggcggcgg gagctacatg gccccgggtg attattttt   5460
tttgtatcta cttctgaccc ttttcaaata tacggtcaac tcatctttca ctggagatgc   5520
ggcctgcttg gtattgcgat gttgtcagct tggcaaattg tggctttcga aaacacaaaa   5580
cgattcctta gtagccatgc attttaagat aacggaatag aagaaagagg aaattaaaaa   5640
aaaaaaaaaa acaaacatcc cgttcataac ccgtagaatc gccgctcttc gtgtatccca   5700
gtaccagttt attttgaata gctcgcccgc tggagagcat cctgaatgca agtaacaacc   5760
gtagaggctg acacggcagg tgttgctagg gagcgtcgtg ttctacaagg ccagacgtct   5820
tcgcggttga tatatatgta tgtttgactg caggctgctc agcgacgaca gtcaagttcg   5880
ccctcgctgc ttgtgcaata atcgcagtgg ggaagccaca ccgtgactcc catctttcag   5940
taaagctctg ttggtgttta tcagcaatac acgtaattta aactcgttag catggggctg   6000
atagcttaat taccgtttac cagtgccgcg gttctgcagc tttccttggc ccgtaaaatt   6060
```

-continued

| | |
|---|---|
| cggcgaagcc agccaatcac cagctaggca ccagctaaac cctataatta gtctcttatc | 6120 |
| aacaccatcc gctcccccgg gatcaatgag gagaatgagg gggatgcggg gctaaagaag | 6180 |
| cctacataac cctcatgcca actcccagtt tacactcgtc gagccaacat cctgactata | 6240 |
| agctaacaca gaatgcctca atcctgggaa gaactggccg ctgataagcg cgcccgcctc | 6300 |
| gcaaaaacca tccctgatga atggaaagtc cagacgctgc ctgcggaaga cagcgttatt | 6360 |
| gatttcccaa agaaatcggg gatccttttca gaggccgaac tgaagatcac agaggcctcc | 6420 |
| gctgcagatc ttgtgtccaa gctggcggcc ggagagttga cctcggtgga agttacgcta | 6480 |
| gcattctgta acgggcagc aatcgcccag cagttagtag ggtcccctct acctctcagg | 6540 |
| gagatgtaac aacgccacct tatgggacta tcaagctgac gctggcttct gtgcagacaa | 6600 |
| actgcgccca cgagttcttc cctgacgccg ctctcgcgca ggcaagggaa ctcgatgaat | 6660 |
| actacgcaaa gcacaagaga cccgttggtc cactccatgg cctccccatc tctctcaaag | 6720 |
| accagcttcg agtcaaggta caccgttgcc cctaagtcgt tagatgtccc ttttttgtcag | 6780 |
| ctaacatatg ccaccagggc tacgaaacat caatgggcta catctcatgg ctaaacaagt | 6840 |
| acgacgaagg ggactcggtt ctgacaacca tgctccgcaa agccggtgcc gtcttctacg | 6900 |
| tcaagacctc tgtcccgcag accctgatgg tctgcgagac agtcaacaac atcatcgggc | 6960 |
| gcaccgtcaa cccacgcaac aagaactggt cgtgcgcgg cagttctggt ggtgagggtg | 7020 |
| cgatcgttgg gattcgtggt ggcgtcatcg gtgtaggaac ggatatcggt ggctcgattc | 7080 |
| gagtgccggc cgcgttcaac ttcctgtacg gtcaaggcc gagtcatggg cggctgccgt | 7140 |
| atgcaaagat ggcgaacagc atggagggtc aggagacggt gcacagcgtt gtcgggccga | 7200 |
| ttacgcactc tgttgagggt gagtccttcg cctcttcctt cttttcctgc tctataccag | 7260 |
| gcctccactg tcctccttc ttgcttttta tactatatac gagaccggca gtcactgatg | 7320 |
| aagtatgtta gacctccgcc tcttcaccaa atccgtcctc ggtcaggagc catggaaata | 7380 |
| cgactccaag gtcatcccca tgccctggcg ccagtccgag tcggacatta ttgcctccaa | 7440 |
| gatcaagaac ggcggggctca atatcggcta ctacaacttc gacggcaatg tccttccaca | 7500 |
| ccctcctatc ctgcgcggcg tggaaaccac cgtcgccgca ctcgccaaag ccggtcacac | 7560 |
| cgtgaccccg tggacgccat acaagcacga tttcggccac gatctcatct cccatatcta | 7620 |
| cgcggctgac ggcagcgccg acgtaatgcg cgatatcagt gcatccggcg agccggcgat | 7680 |
| tccaaatatc aaagacctac tgaacccgaa catcaaagct gttaacatga acgagctctg | 7740 |
| ggacacgcat ctccagaagt ggaattacca gatggagtac cttgagaaat ggcgggaggc | 7800 |
| tgaagaaaag gccgggaagg aactggacgc catcatcgcg ccgattacgc ctaccgctgc | 7860 |
| ggtacggcat gaccagttcc ggtactatgg gtatgcctct gtgatcaacc tgctggattt | 7920 |
| cacgagcgtg gttgttccgg ttacctttgc ggataagaac atcgataaga agaatgagag | 7980 |
| tttcaaggcg gttagtgagc ttgatgccct cgtgcaggaa gagtatgatc cggaggcgta | 8040 |
| ccatggggca ccggttgcag tgcaggttat cggacggaga ctcagtgaag agaggacgtt | 8100 |
| ggcgattgca gaggaagtgg ggaagttgct gggaaatgtg gtgactccat agctaataag | 8160 |
| tgtcagatag caatttgcac aagaaatcaa taccagcaac tgtaaataag cgctgaagtg | 8220 |
| accatgccat gctacgaaag agcagaaaaa aacctgccgt agaaccgaag agatatgaca | 8280 |
| cgcttccatc tctcaaagga agaatccctt cagggttgcg tttccagtct agacacgtat | 8340 |
| aacggcacaa gtgtctctca ccaaatgggt tatatctcaa atgtgatcta aggatggaaa | 8400 |
| gcccagaatc taggcctatt aatattccgg agtatacgta gccggctaac gttaacaacc | 8460 |

```
ggtacctcta gaactatagc tagcatgcgc aaatttaaag cgctgatatc gatcgcgcgc    8520
agatccatat atagggcccg ggttataatt acctcaggtc gacgtcccat ggccattcga    8580
attcgtaatc atggtcatag ctgtttcctg tgtgaaattg ttatccgctc acaattccac    8640
acaacatacg agccggaagc ataaagtgta agcctggggg tgcctaatga gtgagctaac    8700
tcacattaat tgcgttgcgc tcactgcccg ctttccagtc gggaaacctg tcgtgccagc    8760
tgcattaatg aatcggccaa cgcgcgggga gaggcggttt gcgtattggg cgctcttccg    8820
cttcctcgct cactgactcg ctgcgctcgg tcgttcggct gcggcgagcg gtatcagctc    8880
actcaaaggc ggtaatacgg ttatccacag aatcagggga taacgcagga agaacatgt     8940
gagcaaaagg ccagcaaaag gccaggaacc gtaaaaaggc cgcgttgctg gcgttttttcc   9000
ataggctccg ccccccctgac gagcatcaca aaaatcgacg ctcaagtcag aggtggcgaa   9060
acccgacagg actataaaga taccaggcgt ttccccctgg aagctccctc gtgcgctctc    9120
ctgttccgac cctgccgctt accggatacc tgtccgcctt ctcccttcg ggaagcgtgg     9180
cgctttctca tagctcacgc tgtaggtatc tcagttcggt gtaggtcgtt cgctccaagc    9240
tgggctgtgt gcacgaaccc cccgttcagc ccgaccgctg cgccttatcc ggtaactatc    9300
gtcttgagtc aacccggta agacacgact tatcgccact ggcagcagcc actggtaaca    9360
ggattagcag agcgaggtat gtaggcggtg ctacagagtt cttgaagtgg tggcctaact    9420
acggctacac tagaagaaca gtatttggta tctgcgctct gctgaagcca gttaccttcg    9480
gaaaaagagt tggtagctct tgatccggca acaaaccac cgctggtagc ggtggttttt     9540
ttgtttgcaa gcagcagatt acgcgcagaa aaaaaggatc tcaagaagat cctttgatct    9600
tttctacggg gtctgacgct cagtggaacg aaaactcacg ttaagggatt ttggtcatga    9660
gattatcaaa aaggatcttc acctagatcc ttttaaatta aaaatgaagt tttaaatcaa    9720
tctaaagtat atatgagtaa acttggtctg acagttacca atgcttaatc agtgaggcac    9780
ctatctcagc gatctgtcta tttcgttcat ccatagttgc ctgactcccc gtcgtgtaga    9840
taactacgat acgggagggc ttaccatctg gccccagtgc tgcaatgata ccgcgagacc    9900
cacgctcacc ggctccagat ttatcagcaa taaaccagcc agccggaagg gccgagcgca    9960
gaagtggtcc tgcaacttta tccgcctcca tccagtctat taattgttgc cgggaagcta   10020
gagtaagtag ttcgccagtt aatagtttgc gcaacgttgt tgccattgct acaggcatcg   10080
tggtgtcacg ctcgtcgttt ggtatggctt cattcagctc cggttcccaa cgatcaaggc   10140
gagttacatg atccccatg ttgtgcaaaa aagcggttag ctccttcggt cctccgatcg    10200
ttgtcagaag taagttggcc gcagtgttat cactcatggt tatggcagca ctgcataatt   10260
ctcttactgt catgccatcc gtaagatgct tttctgtgac tggtgagtac tcaaccaagt   10320
cattctgaga atagtgtatg cggcgaccga gttgctcttg cccggcgtca atacgggata   10380
ataccgcgcc acatagcaga actttaaaag tgctcatcat tggaaaacgt tcttcggggc   10440
gaaaactctc aaggatctta ccgctgttga tccagttc gatgtaaccc actcgtgcac      10500
ccaactgatc ttcagcatct tttactttca ccagcgtttc tgggtgagca aaaacaggaa   10560
ggcaaaatgc cgcaaaaaag gaataaggg cgacacggaa atgttgaata ctcatactct     10620
tccttttcca atattattga agcatttatc agggttattg tctcatgagc ggatacatat   10680
ttgaatgtat ttagaaaaat aaacaaatag gggttccgcg cacatttccc cgaaaagtgc   10740
cacctgacgt ctaagaaacc attattatca tgacattaac ctataaaaat aggcgtatca   10800
cgaggccctt tcgtctcgcg cgtttcggtg atgacggtga aaacctctga cacatgcagc   10860
```

| | |
|---|---|
| tcccggagac ggtcacagct tgtctgtaag cggatgccgg gagcagacaa gcccgtcagg | 10920 |
| gcgcgtcagc gggtgttggc gggtgtcggg gctggcttaa ctatgcggca tcagagcaga | 10980 |
| ttgtactgag agtgcaccat aaaattgtaa acgttaatat tttgttaaaa ttcgcgttaa | 11040 |
| atttttgtta aatcagctca ttttttaacc aataggccga aatcggcaaa atcccttata | 11100 |
| aatcaaaaga atagcccgag atagggttga gtgttgttcc agtttggaac aagagtccac | 11160 |
| tattaaagaa cgtggactcc aacgtcaaag ggcgaaaaac cgtctatcag ggcgatggcc | 11220 |
| cactacgtga accatcaccc aaatcaagtt ttttgggtc gaggtgccgt aaagcactaa | 11280 |
| atcggaaccc taaagggagc ccccgattta gagcttgacg gggaaagccg gcgaacgtgg | 11340 |
| cgagaaagga agggaagaaa gcgaaaggag cgggcgctag ggcgctggca agtgtagcgg | 11400 |
| tcacgctgcg cgtaaccacc acaccgccg cgcttaatgc gccgctacag ggcgcgtact | 11460 |
| atggttgctt tgacgtatgc ggtgtgaaat accgcacaga tgcgtaagga gaaaataccg | 11520 |
| catcaggcgc cattcgccat tcaggctgcg caactgttgg gaagggcgat cggtgcgggc | 11580 |
| ctcttcgcta ttacgccagc tggcgaaagg gggatgtgct gcaaggcgat taagttgggt | 11640 |
| aacgccaggg ttttcccagt cacgacgttg taaaacgacg gccagtgcc | 11689 |

<210> SEQ ID NO 7
<211> LENGTH: 10208
<212> TYPE: DNA
<213> ORGANISM: Artificial
<220> FEATURE:
<223> OTHER INFORMATION: synthetic expression plasmid

<400> SEQUENCE: 7

| | |
|---|---|
| aagcttacta gtacttctcg agctctgtac atgtccggtc gcgacgtacg cgtatcgatg | 60 |
| gcgccagctg caggcggccg cctgcagcca cttgcagtcc cgtggaattc tcacggtgaa | 120 |
| tgtaggcctt ttgtagggta ggaattgtca ctcaagcacc cccaacctcc attacgcctc | 180 |
| ccccatagag ttcccaatca gtgagtcatg gcactgttct caaatagatt ggggagaagt | 240 |
| tgacttccgc ccagagctga aggtcgcaca accgcatgat atagggtcgg caacggcaaa | 300 |
| aaagcacgtg gctcaccgaa aagcaagatg tttgcgatct aacatccagg aacctggata | 360 |
| catccatcat cacgcacgac cactttgatc tgctggtaaa ctcgtattcg ccctaaaccg | 420 |
| aagtgcgtgg taaatctaca cgtgggcccc tttcggtata ctgcgtgtgt cttctctagg | 480 |
| tgccattctt ttcccttcct ctagtgttga attgtttgtg ttggagtccg agctgtaact | 540 |
| acctctgaat ctctggagaa tggtggacta acgactaccg tgcacctgca tcatgtatat | 600 |
| aatagtgatc ctgagaaggg gggtttggag caatgtggga cttttgatggt catcaaacaa | 660 |
| agaacgaaga cgcctctttt gcaaagtttt gtttcggcta cggtgaagaa ctggatactt | 720 |
| gttgtgtctt ctgtgtattt ttgtggcaac aagaggccag agacaatcta ttcaaacacc | 780 |
| aagcttgctc ttttgagcta caagaacctg tggggtatat atctagagtt gtgaagtcgg | 840 |
| taatcccgct gtatagtaat acgagtcgca tctaaatact ccgaagctgc tgcgaacccg | 900 |
| gagaatcgag atgtgctgga aagcttctag cgagcggcta aattagcatg aaaggctatg | 960 |
| agaaattctg gagacggctt gttgaatcat ggcgttccat tcttcgacaa gcaaagcgtt | 1020 |
| ccgtcgcagt agcaggcact cattcccgaa aaaactcgga gattcctaag tagcgatgga | 1080 |
| accggaataa tataataggc aatacattga gttgcctcga cggttgcaat gcaggggtac | 1140 |
| tgagcttgga cataactgtt ccgtacccca cctcttctca acctttggcg tttccctgat | 1200 |
| tcagcgtacc cgtacaagtc gtaatcacta ttaacccaga ctgaccggac gtgttttgcc | 1260 |

```
cttcatttgg agaaataatg tcattgcgat gtgtaatttg cctgcttgac cgactggggc    1320
tgttcgaagc ccgaatgtag gattgttatc cgaactctgc tcgtagaggc atgttgtgaa    1380
tctgtgtcgg gcaggacacg cctcgaaggt tcacggcaag ggaaaccacc gatagcagtg    1440
tctagtagca acctgtaaag ccgcaatgca gcatcactgg aaaatacaaa ccaatggcta    1500
aaagtacata agttaatgcc taaagaagtc ataccagc ggctaataat tgtacaatca      1560
agtggctaaa cgtaccgtaa tttgccaacg gcttgtgggg ttgcagaagc aacggcaaag    1620
ccccacttcc ccacgtttgt ttcttcactc agtccaatct cagctggtga tcccccaatt    1680
gggtcgcttg tttgttccgg tgaagtgaaa gaagacagag gtaagaatgt ctgactcgga    1740
gcgttttgca tacaaccaag ggcagtgatg gaagacagtg aaatgttgac attcaaggag    1800
tatttagcca gggatgcttg agtgtatcgt gtaaggaggt ttgtctgccg atacgacgaa    1860
tactgtatag tcacttctga tgaagtggtc catattgaaa tgtaaagtcg gcactgaaca    1920
ggcaaaagat tgagttgaaa ctgcctaaga tctcgggccc tcgggccttc ggcctttggg    1980
tgtacatgtt tgtgctccgg gcaaatgcaa agtgtggtag gatcgaacac actgctgcct    2040
ttaccaagca gctgagggta tgtgataggc aaatgttcag gggccactgc atggtttcga    2100
atagaaagag aagcttagcc aagaacaata gccgataaag atagcctcat taaacggaat    2160
gagctagtag gcaaagtcag cgaatgtgta tatataaagg ttcgaggtcc gtgcctccct    2220
catgctctcc ccatctactc atcaactcag atcctccagg agacttgtac accatctttt    2280
gaggcacaga aacccaatag tcaaccatca caagtttgta caaaaaagca ggctccgcgg    2340
ccgccccctt caccatgcag acctttggag cttttctcgt ttccttcctc gccgccagcg    2400
gcctggccgc ggccgctatt ggaccagttg ctgatctgca catcgttaac aaggatttgg    2460
ccccagacgg cgtccagcgc ccaactgttc tggccggtgg aacttttccg ggcacgctga    2520
ttaccggtca aaagggcgac aacttccagc tgaacgtgat tgatgacctg accgacgatc    2580
gcatgttgac ccctacttcg atccattggc atggtttctt ccagaaggga accgcctggg    2640
ccgacggtcc ggctttcgtt acacagtgcc ctattatcgc agacaactcc ttcctctacg    2700
atttcgacgt tccgaccag gcgggcacct tctggtacca ctcacacttg tctacacagt    2760
actgcgacgg tctgcgcggt gccttcgttg tttacgaccc caacgaccct cacaaggacc    2820
tttatgatgt cgatgacggt ggcacagtta tcacattggc tgactggtat cacgtcctcg    2880
ctcagaccgt tgtcggagct gctacacccg actctacgct gattaacggc ttgggacgca    2940
gccagactgg ccccgccgac gctgagctgg ccgttatctc tgttgaacac aacaagagat    3000
accgtttcag actcgtctcc atctcgtgcg atcccaactt cacttttagc gtcgacggtc    3060
acaacatgac ggttatcgag gttgatggcg tgaatacccg ccctctcacc gtcgattcca    3120 ttcaaattt cgccggccag cgatactcct ttgtgctgaa tgccaatcag cccgaggata    3180
actactggat ccgcgctatg cctaacatcg gacgaaacac cactacccct tgatggcaaga    3240 atgccgctat cctgcgatac aagaacgcca gcgttgagga gcccaaaacc gtcggaggac    3300
ccgcgcagag cccattgaac gaggccgacc tgccgacctct ggtgcccgct cctgtccctg    3360
gcaacgcagt tcctggtggt gcggacatca accaccgcct gaacctgaca ttcagcaacg    3420
gcctcttctc tatcaataac gcatcattta caaaccccag cgtccctgcc ttgttgcaga    3480
ttctttccgg cgcacaaaac gctcaggatc tgcttccac cggttcttat atcggcttgg    3540
agttgggcaa ggtcgttgaa ctcgtgatcc ctcccttggc cgttggtggc ccccatccat    3600
tccacttgca cggccacaac ttttgggtcg tccgaagcgc tggttctgac gagtataatt    3660
```

-continued

```
tcgacgatgc aattttgcgc gacgtggtca gcattggcgc gggaactgac gaggttacta      3720
tccgttttgt cactgataac ccaggccctt ggttcctcca ttgccacatc gactggcacc      3780
tcgaagccgg cctcgccatt gttttcgccg aaggcatcaa tcaaaccgca gccgccaacc      3840
cgactccaca ggcctgggac gaactctgcc ccaagtataa cggactctcc gcttcccaga      3900
aagtgaagcc caagaaggga acagccatct aaaagggtgg gcgcgccgac ccagctttct      3960
tgtacaaagt ggtgatcgcg ccagctccgt gcgaaagcct gacgcaccgg tagattcttg      4020
gtgagcccgt atcatgacgg cggcgggagc tacatggccc cgggtgattt attttttttg      4080
tatctacttc tgacccttt caaatatacg gtcaactcat ctttcactgg agatgcggcc       4140
tgcttggtat tgcgatgttg tcagcttggc aaattgtggc tttcgaaaac acaaaacgat      4200
tccttagtag ccatgcattt taagataacg gaatagaaga aagaggaaat taaaaaaaaa      4260
aaaaaaacaa acatcccgtt cataacccgt agaatcgccg ctcttcgtgt atcccagtac      4320
cagtttattt tgaatagctc gcccgctgga gagcatcctg aatgcaagta acaaccgtag      4380
aggctgacac ggcaggtgtt gctagggagc gtcgtgttct acaaggccag acgtcttcgc      4440
ggttgatata tatgtatgtt tgactgcagg ctgctcagcg acgacagtca agttcgccct      4500
cgctgcttgt gcaataatcg cagtggggaa gccacaccgt gactcccatc tttcagtaaa      4560
gctctgttgg tgtttatcag caatacacgt aatttaaact cgttagcatg ggctgatag       4620
cttaattacc gtttaccagt gccatggttc tgcagctttc cttggcccgt aaaattcggc      4680
gaagccagcc aatcaccagc taggcaccag ctaaaccta taattagtct cttatcaaca       4740
ccatccgctc ccccgggatc aatgaggaga atgaggggga tgcggggcta aagaagccta      4800
cataaccctc atgccaactc ccagtttaca ctcgtcgagc caacatcctg actataagct      4860
aacacagaat gcctcaatcc tgggaagaac tggccgctga taagcgcgcc cgcctcgcaa      4920
aaaccatccc tgatgaatgg aaagtccaga cgctgcctgc ggaagacagc gttattgatt      4980
tcccaaagaa atcggggatc cttcagaggg ccgaactgaa gatcacagag gcctccgctg      5040
cagatcttgt gtccaagctg gcggccggag agttgacctc ggtggaagtt acgctagcat      5100
tctgtaaacg ggcagcaatc gcccagcagt tagtagggtc ccctctacct ctcagggaga     5160
tgtaacaacg ccaccttatg ggactatcaa gctgacgctg gcttctgtgc agacaaactg      5220
cgcccacgag ttcttccctg acgccgctct cgcgcaggca agggaactcg atgaatacta      5280
cgcaaagcac aagagacccg ttggtccact ccatggcctc cccatctctc tcaaagacca      5340
gcttcgagtc aaggtacacc gttgcccta agtcgttaga tgtccctttt tgtcagctaa       5400
catatgccac cagggctacg aaacatcaat gggctacatc tcatggctaa acaagtacga      5460
cgaaggggac tcggttctga caaccatgct ccgcaaagcc ggtgccgtct tctacgtcaa      5520
gacctctgtc ccgcagaccc tgatggtctg cgagacagtc aacaacatca tcgggcgcac      5580
cgtcaaccca cgcaacaaga actggtcgtg cggcggcagt tctggtggtg agggtgcgat      5640
cgttgggatt cgtggtggcg tcatcggtgt aggaacggat atcggtggct cgattcgagt      5700
gccggccgcg ttcaacttcc tgtacggtct aaggccgagt catgggcggc tgccgtatgc      5760
aaagatggcg aacagcatgg agggtcagga gacggtgcac agcgttgtcg ggccgattac      5820
gcactctgtt gagggtgagt ccttcgcctc ttccttcttt tcctgctcta taccaggcct      5880
ccactgtcct cctttcttgc ttttatact atatacgaga ccggcagtca ctgatgaagt       5940
atgttagacc tccgctctt caccaaatcc gtcctcggtc aggagccatg gaaatacgac       6000
tccaaggtca tccccatgcc ctggcgccag tccgagtcgg acattattgc ctccaagatc      6060
```

```
aagaacggcg ggctcaatat cggctactac aacttcgacg gcaatgtcct tccacaccct   6120
cctatcctgc gcggcgtgga aaccaccgtc gccgcactcg ccaaagccgg tcacaccgtg   6180
accccgtgga cgccatacaa gcacgatttc ggccacgatc tcatctccca tatctacgcg   6240
gctgacggca gcgccgacgt aatgcgcgat atcagtgcat ccggcgagcc ggcgattcca   6300
aatatcaaag acctactgaa cccgaacatc aaagctgtta acatgaacga gctctgggac   6360
acgcatctcc agaagtggaa ttaccagatg gagtaccttg agaaatggcg ggaggctgaa   6420
gaaaaggccg ggaaggaact ggacgccatc atcgcgccga ttacgcctac cgctgcggta   6480
cggcatgacc agttccggta ctatgggtat gcctctgtga tcaacctgct ggatttcacg   6540
agcgtggttg ttccggttac ctttgcggat aagaacatcg ataagaagaa tgagagtttc   6600
aaggcggtta gtgagcttga tgccctcgtg caggaagagt atgatccgga ggcgtaccat   6660
ggggcaccgg ttgcagtgca ggttatcgga cggagactca gtgaagagag gacgttggcg   6720
attgcagagg aagtggggaa gttgctggga aatgtggtga ctccatagct aataagtgtc   6780
agatagcaat ttgcacaaga aatcaatacc agcaactgta aataagcgct gaagtgacca   6840
tgccatgcta cgaaagagca gaaaaaaacc tgccgtagaa ccgaagagat atgcacgct   6900 tccatctctc aaaggaagaa tcccttcagg gttgcgtttc cagtctagac acgtataacg   6960
gcacaagtgt ctctcaccaa atgggttata tctcaaatgt gatctaagga tggaaagccc   7020
agaatatcga tcgcgcgcag atccatatat agggcccggg ttataattac ctcaggtcga   7080
cgtcccatgg ccattcgaat tcgtaatcat ggtcatagct gtttcctgtg tgaaattgtt   7140
atccgctcac aattccacac aacatacgag ccggaagcat aaagtgtaaa gcctggggtg   7200
cctaatgagt gagctaactc acattaattg cgttgcgctc actgcccgct ttccagtcgg   7260
gaaacctgtc gtgccagctg cattaatgaa tcggccaacg cgcggggaga ggcggtttgc   7320
gtattgggcg ctcttccgct tcctcgctca ctgactcgct gcgctcggtc gttcggctgc   7380
ggcgagcggt atcagctcac tcaaaggcgg taatacggtt atccacagaa tcaggggata   7440
acgcaggaaa gaacatgtga gcaaaaggcc agcaaaaggc caggaaccgt aaaaaggccg   7500
cgttgctggc gtttttccat aggctccgcc cccctgacga gcatcacaaa aatcgacgct   7560
caagtcagag gtggcgaaac ccgacaggac tataaagata ccaggcgttt ccccctggaa   7620
gctccctcgt gcgctctcct gttccgaccc tgccgcttac cggatacctg tccgcctttc   7680
tcccttcggg aagcgtggcg ctttctcata gctcacgctg taggtatctc agttcggtgt   7740
aggtcgttcg ctccaagctg ggctgtgtgc acgaaccccc cgttcagccc gaccgctgcg   7800
ccttatccgg taactatcgt cttgagtcca acccggtaag acacgactta tcgccactgg   7860
cagcagccac tggtaacagg attagcagag cgaggtatgt aggcggtgct acagagttct   7920
tgaagtggtg gcctaactac ggctacacta agaacagt atttggtatc tgcgctctgc   7980
tgaagccagt taccttcgga aaagagttg gtagctcttg atccggcaaa caaaccaccg   8040
ctggtagcgg tggttttttt gtttgcaagc agcagattac gcgcagaaaa aaggatctc   8100 aagaagatcc tttgatcttt tctacggggt ctgacgctca gtggaacgaa aactcacgtt   8160
aagggatttt ggtcatgaga ttatcaaaaa ggatcttcac ctagatcctt ttaaattaaa   8220
aatgaagttt taaatcaatc taagtatat atgagtaaac ttggtctgac agttaccaat   8280
gcttaatcag tgaggcacct atctcagcga tctgtctatt tcgttcatcc atagttgcct   8340
gactccccgt cgtgtagata actacgatac gggagggctt accatctggc cccagtgctg   8400
caatgatacc gcgagaccca cgctcaccgg ctccagattt atcagcaata aaccagccag   8460
```

```
ccggaagggc cgagcgcaga agtggtcctg caactttatc cgcctccatc cagtctatta    8520
attgttgccg ggaagctaga gtaagtagtt cgccagttaa tagtttgcgc aacgttgttg    8580
ccattgctac aggcatcgtg gtgtcacgct cgtcgtttgg tatggcttca ttcagctccg    8640
gttcccaacg atcaaggcga gttacatgat cccccatgtt gtgcaaaaaa gcggttagct    8700
ccttcggtcc tccgatcgtt gtcagaagta agttggccgc agtgttatca ctcatggtta    8760
tggcagcact gcataattct cttactgtca tgccatccgt aagatgcttt tctgtgactg    8820
gtgagtactc aaccaagtca ttctgagaat agtgtatgcg gcgaccgagt tgctcttgcc    8880
cggcgtcaat acgggataat accgcgccac atagcagaac tttaaaagtg ctcatcattg    8940
gaaaacgttc ttcggggcga aaactctcaa ggatcttacc gctgttgaga tccagttcga    9000
tgtaacccac tcgtgcaccc aactgatctt cagcatcttt tactttcacc agcgtttctg    9060
ggtgagcaaa aacaggaagg caaaatgccg caaaaaaggg aataagggcg acacggaaat    9120
gttgaatact catactcttc ctttttcaat attattgaag catttatcag ggttattgtc    9180
tcatgagcgg atacatattt gaatgtattt agaaaaataa acaaataggg gttccgcgca    9240
catttccccg aaaagtgcca cctgacgtct aagaaaccat tattatcatg acattaacct    9300
ataaaaatag gcgtatcacg aggccctttc gtctcgcgcg tttcggtgat gacggtgaaa    9360
acctctgaca catgcagctc ccggagacgg tcacagcttg tctgtaagcg gatgccggga    9420
gcagacaagc ccgtcagggc gcgtcagcgg gtgttggcgg gtgtcggggc tggcttaact    9480
atgcggcatc agagcagatt gtactgagag tgcaccataa aattgtaaac gttaatattt    9540
tgttaaaatt cgcgttaaat ttttgttaaa tcagctcatt ttttaaccaa taggccgaaa    9600
tcggcaaaat cccttataaa tcaaaagaat agcccgagat agggttgagt gttgttccag    9660
tttggaacaa gagtccacta ttaaagaacg tggactccaa cgtcaaaggg cgaaaaaccg    9720
tctatcaggg cgatggccca ctacgtgaac catcacccaa atcaagtttt ttggggtcga    9780
ggtgccgtaa agcactaaat cggaacccta agggagcccc cgatttaga gcttgacggg    9840 gaaagccggc gaacgtggcg agaaaggaag ggaagaaagc gaaaggagcg ggcgctaggg    9900
cgctggcaag tgtagcggtc acgctgcgcg taaccaccac acccgccgcg cttaatgcgc    9960
cgctacaggg cgcgtactat ggttgctttg acgtatgcgg tgtgaaatac cgcacagatg   10020
cgtaaggaga aaataccgca tcaggcgcca ttcgccattc aggctgcgca actgttggga   10080
agggcgatcg gtgcgggcct cttcgctatt acgccagctg gcgaaagggg gatgtgctgc   10140
aaggcgatta agttgggtaa cgccagggtt ttcccagtca cgacgttgta aaacgacggc   10200
cagtgccc                                                             10208

<210> SEQ ID NO 8
<211> LENGTH: 10199
<212> TYPE: DNA
<213> ORGANISM: Artificial
<220> FEATURE:
<223> OTHER INFORMATION: synthetic expression plasmid

<400> SEQUENCE: 8
aagcttacta gtacttctcg agctctgtac atgtccggtc gcgacgtacg cgtatcgatg      60
gcgccagctg caggcggccg cctgcagcca cttgcagtcc cgtggaattc tcacggtgaa     120
tgtaggcctt ttgtagggta ggaattgtca ctcaagcacc cccaacctcc attacgcctc     180
ccccatagag ttcccaatca gtgagtcatg cactgttcct caaatagatt ggggagaagt     240
tgacttccgc ccagagctga aggtcgcaca accgcatgat atagggtcgg caacggcaaa     300
```

-continued

| | |
|---|---|
| aaagcacgtg gctcaccgaa aagcaagatg tttgcgatct aacatccagg aacctggata | 360 |
| catccatcat cacgcacgac cactttgatc tgctggtaaa ctcgtattcg ccctaaaccg | 420 |
| aagtgcgtgg taaatctaca cgtgggcccc tttcggtata ctgcgtgtgt cttctctagg | 480 |
| tgccattctt ttcccttcct ctagtgttga attgtttgtg ttggagtccg agctgtaact | 540 |
| acctctgaat ctctggagaa tggtggacta acgactaccg tgcacctgca tcatgtatat | 600 |
| aatagtgatc ctgagaaggg ggggttttggag caatgtggga cttttgatggt catcaaacaa | 660 |
| agaacgaaga cgcctctttt gcaaagtttt gtttcggcta cggtgaagaa ctggatactt | 720 |
| gttgtgtctt ctgtgtattt ttgtggcaac aagaggccag agacaatcta ttcaaacacc | 780 |
| aagcttgctc ttttgagcta caagaacctg tggggtatat atctagagtt gtgaagtcgg | 840 |
| taatcccgct gtatagtaat acgagtcgca tctaaatact ccgaagctgc tgcgaacccg | 900 |
| gagaatcgag atgtgctgga aagcttctag cgagcggcta aattagcatg aaaggctatg | 960 |
| agaaattctg gagacggctt gttgaatcat ggcgttccat tcttcgacaa gcaaagcgtt | 1020 |
| ccgtcgcagt agcaggcact cattcccgaa aaaactcgga gattcctaag tagcgatgga | 1080 |
| accggaataa tataataggc aatacattga gttgcctcga cggttgcaat gcaggggtac | 1140 |
| tgagcttgga cataactgtt ccgtaccccca cctcttctca acctttggcg tttccctgat | 1200 |
| tcagcgtacc cgtacaagtc gtaatcacta ttaacccaga ctgaccggac gtgttttgcc | 1260 |
| cttcatttgg agaaataatg tcattgcgat gtgtaatttg cctgcttgac cgactggggc | 1320 |
| tgttcgaagc ccgaatgtag gattgttatc cgaactctgc tcgtagaggc atgttgtgaa | 1380 |
| tctgtgtcgg gcaggacacg cctcgaaggt tcacggcaag ggaaaccacc gatagcagtg | 1440 |
| tctagtagca acctgtaaag ccgcaatgca gcatcactgg aaaatacaaa ccaatggcta | 1500 |
| aaagtacata agttaatgcc taaagaagtc atataccagc ggctaataat tgtacaatca | 1560 |
| agtggctaaa cgtaccgtaa tttgccaacg gcttgtgggg ttgcagaagc aacggcaaag | 1620 |
| ccccacttcc ccacgtttgt ttcttcactc agtccaatct cagctggtga tcccccaatt | 1680 |
| gggtcgcttg tttgttccgg tgaagtgaaa gaagacagag gtaagaatgt ctgactcgga | 1740 |
| gcgttttgca tacaaccaag ggcagtgatg gaagacagtg aaatgttgac attcaaggag | 1800 |
| tatttagcca gggatgcttg agtgtatcgt gtaaggaggt ttgtctgccg atacgacgaa | 1860 |
| tactgtatag tcacttctga tgaagtggtc catattgaaa tgtaaagtcg gcactgaaca | 1920 |
| ggcaaaagat tgagttgaaa ctgcctaaga tctcgggccc tcgggccttc ggcctttggg | 1980 |
| tgtacatgtt tgtgctccgg gcaaatgcaa agtgtggtag gatcgaacac actgctgcct | 2040 |
| ttaccaagca gctgagggta tgtgataggc aaatgttcag gggccactgc atggtttcga | 2100 |
| atagaaagag aagcttagcc aagaacaata gccgataaag atagcctcat taaacggaat | 2160 |
| gagctagtag gcaaagtcag cgaatgtgta tatataaagg ttcgaggtcc gtgcctccct | 2220 |
| catgctctcc ccatcactc atcaactcag atcctccagg agacttgtac accatctttt | 2280 |
| gaggcacaga aacccaatag tcaaccatca caagtttgta caaaaaagca ggctccgcgg | 2340 |
| ccgcccccctt caccatgtat cggaagttgg ccgtcatctc ggccttcttg gccacagctc | 2400 |
| gtgctgctat tggaccagtt gctgatctgc acatcgttaa caaggatttg gccccagacg | 2460 |
| gcgtccagcg cccaactgtt ctggccggtg aacttttcc gggcacgctg attaccggtc | 2520 |
| aaaagggcga caacttccag ctgaacgtga ttgatgacct gaccgacgat cgcatgttga | 2580 |
| ccccctacttc gatccattgg catggttcct tccagaaggg aaccgcctgg gccgacggtc | 2640 |
| cggctttcgt tacacagtgc cctattatcg cagacaactc cttcctctac gatttcgacg | 2700 |

```
ttcccgacca ggcgggcacc ttctggtacc actcacactt gtctacacag tactgcgacg   2760
gtctgcgcgg tgccttcgtt gtttacgacc ccaacgaccc tcacaaggac ctttatgatg   2820
tcgatgacgg tggcacagtt atcacattgg ctgactggta tcacgtcctc gctcagaccg   2880
ttgtcggagc tgctacaccc gactctacgc tgattaacgg cttgggacgc agccagactg   2940
gccccgccga cgctgagctg gccgttatct ctgttgaaca caacaagaga taccgtttca   3000
gactcgtctc catctcgtgc gatcccaact tcacttttag cgtcgacggt cacaacatga   3060
cggttatcga ggttgatggc gtgaataccc gccctctcac cgtcgattcc attcaaattt   3120
tcgccggcca gcgatactcc tttgtgctga atgccaatca gcccgaggat aactactgga   3180
tccgcgctat gcctaacatc ggacgaaaca ccactaccct tgatggcaag aatgccgcta   3240
tcctgcgata caagaacgcc agcgttgagg agcccaaaac cgtcggagga cccgcgcaga   3300
gcccattgaa cgaggccgac ctgcgacctc tggtgcccgc tcctgtccct ggcaacgcag   3360
ttcctggtgg tgcggacatc aaccaccgcc tgaacctgac attcagcaac ggcctcttct   3420
ctatcaataa cgcatcattt acaaacccca gcgtccctgc cttgttgcag attctttccg   3480
gcgcacaaaa cgctcaggat ctgcttccca ccggttctta tatcggcttg gagttgggca   3540
aggtcgttga actcgtgatc cctcccttgg ccgttggtgg cccccatcca ttccacttgc   3600
acggccacaa cttttgggtc gtccgaagcg ctggttctga cgagtataat ttcgacgatg   3660
caattttgcg cgacgtggtc agcattggcg cgggaactga cgaggttact atccgttttg   3720
tcactgataa cccaggccct tggttcctcc attgccacat cgactggcac ctcgaagccg   3780
gcctcgccat tgttttcgcc gaaggcatca atcaaaccgc agccgccaac ccgactccac   3840
aggcctggga cgaactctgc cccaagtata acggactctc cgcttcccag aaagtgaagc   3900
ccaagaaggg aacagccatc taaaagggtg ggcgcgccga cccagctttc ttgtacaaag   3960
tggtgatcgc gccagctccg tgcgaaagcc tgacgcaccg gtagattctt ggtgagcccg   4020
tatcatgacg gcggcgggag ctacatggcc ccgggtgatt tatttttttt gtatctactt   4080
ctgaccctit tcaaatatac ggtcaactca tctttcactg gagatgcggc ctgcttggta   4140
ttgcgatgtt gtcagcttgg caaattgtgg cttttcgaaaa cacaaaacga ttccttagta   4200
gccatgcatt ttaagataac ggaatagaag aaagaggaaa ttaaaaaaaa aaaaaaaaca   4260
aacatcccgt tcataacccg tagaatcgcc gctcttcgtg tatcccagta ccagtttatt   4320
ttgaatagct cgcccgctgg agagcatcct gaatgcaagt aacaaccgta gaggctgaca   4380
cggcaggtgt tgctagggag cgtcgtgttc tacaaggcca gacgtcttcg cggttgatat   4440
atatgtatgt ttgactgcag gctgctcagc gacgacagtc aagttcgccc tcgctgcttg   4500
tgcaataatc gcagtgggga agccacaccg tgactcccat cttttcagtaa agctctgttg   4560
gtgtttatca gcaatacacg taatttaaac tcgttagcat ggggctgata gcttaattac   4620
cgtttaccag tgccatggtt ctgcagcttt ccttggcccg taaaattcgg cgaagccagc   4680
caatcaccag ctaggcacca gctaaaccct ataattagtc tcttatcaac accatccgct   4740
cccccgggat caatgaggag aatgaggggg atgcggggct aaagaagcct acataacccct   4800
catgccaact cccagtttac actcgtcgag ccaacatcct gactataagc taacacagaa   4860
tgcctcaatc ctgggaagaa ctggccgctg ataagcgcgc ccgcctcgca aaaaccatcc   4920
ctgatgaatg gaaagtccag acgctgcctg cggaagacag cgttattgat ttcccaaaga   4980
aatcggggat cctttcagag gccgaactga agatcacaga ggcctccgct gcagatcttg   5040
tgtccaagct ggcggccgga gagttgacct cggtggaagt tacgctagca ttctgtaaac   5100
```

```
gggcagcaat cgcccagcag ttagtagggt cccctctacc tctcagggag atgtaacaac   5160
gccaccttat gggactatca agctgacgct ggcttctgtg cagacaaact gcgcccacga   5220
gttcttccct gacgccgctc tcgcgcaggc aagggaactc gatgaatact acgcaaagca   5280
caagagaccc gttggtccac tccatggcct ccccatctct ctcaaagacc agcttcgagt   5340
caaggtacac cgttgcccct aagtcgttag atgtcccttt ttgtcagcta acatatgcca   5400
ccagggctac gaaacatcaa tgggctacat ctcatggcta acaagtacg acgaagggga   5460
ctcggttctg acaaccatgc tccgcaaagc cggtgccgtc ttctacgtca agacctctgt   5520
cccgcagacc ctgatggtct gcgagacagt caacaacatc atcgggcgca ccgtcaaccc   5580
acgcaacaag aactggtcgt gcggcggcag ttctggtggt gagggtgcga tcgttgggat   5640
tcgtggtggc gtcatcggtg taggaacgga tatcggtggc tcgattcgag tgccggccgc   5700
gttcaacttc ctgtacggtc taaggccgag tcatgggcgg ctgccgtatg caaagatggc   5760
gaacagcatg gagggtcagg agacggtgca cagcgttgtc gggccgatta cgcactctgt   5820
tgagggtgag tccttcgcct cttccttctt ttcctgctct ataccaggcc tccactgtcc   5880
tcctttcttg cttttttatac tatatacgag accggcagtc actgatgaag tatgttagac   5940
ctccgcctct tcaccaaatc cgtcctcggt caggagccat ggaaatacga ctccaaggtc   6000
atccccatgc cctggcgcca gtccgagtcg acattattg cctccaagat caagaacggc   6060
gggctcaata tcggctacta caacttcgac ggcaatgtcc ttccacaccc tcctatcctg   6120
cgcggcgtgg aaaccaccgt cgccgcactc gccaaagccg gtcacaccgt gaccccgtgg   6180
acgccataca agcacgattt cggccacgat ctcatctccc atatctacgc ggctgacggc   6240
agcgccgacg taatgcgcga tatcagtgca tccggcgagc cggcgattcc aaatatcaaa   6300
gacctactga acccgaacat caaagctgtt aacatgaacg agctctggga cacgcatctc   6360
cagaagtgga attaccagat ggagtaccct gagaaatggc gggaggctga agaaaaggcc   6420
gggaaggaac tggacgccat catcgcgccg attacgccta ccgctgcggt acggcatgac   6480
cagttccggt actatgggta tgcctctgtg atcaacctgc tggatttcac gagcgtggtt   6540
gttccggtta cctttgcgga taagaacatc gataagaaga atgagagttt caaggcggtt   6600
agtgagcttg atgccctcgt gcaggaagag tatgatccgg aggcgtacca tggggcaccg   6660
gttgcagtgc aggttatcgg acggagactc agtgaagaga ggacgttggc gattgcagag   6720
gaagtgggga agttgctggg aaatgtggtg actccatagc taataagtgt cagatagcaa   6780
tttgcacaag aaatcaatac cagcaactgt aaataagcgc tgaagtgacc atgccatgct   6840
acgaaagagc agaaaaaaac ctgccgtaga accgaagaga tatgacacgc ttccatctct   6900
caaaggaaga atcccttcag ggttgcgttt ccagtctaga cacgtataac ggcacaagtg   6960
tctctcacca aatgggttat atctcaaatg tgatctaagg atggaaagcc cagaatatcg   7020
atcgcgcgca gatccatata tagggcccgg gttataatta cctcaggtcg acgtcccatg   7080
gccattcgaa ttcgtaatca tggtcatagc tgtttcctgt gtgaaattgt tatccgctca   7140
caattccaca acatacga gccggaagca taaagtgtaa agcctggggt gcctaatgag   7200
tgagctaact cacattaatt gcgttgcgct cactgcccgc tttccagtcg ggaaacctgt   7260
cgtgccagct gcattaatga atcggccaac gcgcggggag aggcggtttg cgtattgggc   7320
gctcttccgc ttcctcgctc actgactcgc tgcgctcggt cgttcggctg cggcgagcgg   7380
tatcagctca ctcaaaggcg gtaatacggt tatccacaga atcaggggat aacgcaggaa   7440
agaacatgtg agcaaaaggc cagcaaaagg ccaggaaccg taaaaaggcc gcgttgctgg   7500
```

```
cgttttcca taggctccgc cccctgacg agcatcacaa aaatcgacgc tcaagtcaga   7560
ggtggcgaaa cccgacagga ctataaagat accaggcgtt tccccctgga agctccctcg   7620
tgcgctctcc tgttccgacc ctgccgctta ccggatacct gtccgccttt ctcccttcgg   7680
gaagcgtggc gctttctcat agctcacgct gtaggtatct cagttcggtg taggtcgttc   7740
gctccaagct gggctgtgtg cacgaacccc cgttcagccc gaccgctgc gccttatccg   7800 gtaactatcg tcttgagtcc aacccggtaa gacacgactt atcgccactg gcagcagcca   7860
ctggtaacag gattagcaga gcgaggtatg taggcggtgc tacagagttc ttgaagtggt   7920
ggcctaacta cggctacact agaagaacag tatttggtat ctgcgctctg ctgaagccag   7980
ttaccttcgg aaaaagagtt ggtagctctt gatccggcaa acaaaccacc gctggtagcg   8040 gtggttttt tgtttgcaag cagcagatta cgcgcagaaa aaaggatct caagaagatc   8100 ctttgatctt ttctacgggg tctgacgctc agtggaacga aaactcacgt taagggattt   8160
tggtcatgag attatcaaaa aggatcttca cctagatcct tttaaattaa aaatgaagtt   8220
ttaaatcaat ctaaagtata tatgagtaaa cttggtctga cagttaccaa tgcttaatca   8280
gtgaggcacc tatctcagcg atctgtctat ttcgttcatc catagttgcc tgactccccg   8340
tcgtgtagat aactacgata cgggagggct taccatctgg ccccagtgct gcaatgatac   8400
cgcgagaccc acgctcaccg gctccagatt tatcagcaat aaaccagcca gccgaaggg   8460 ccgagcgcag aagtggtcct gcaactttat ccgcctccat ccagtctatt aattgttgcc   8520
gggaagctag agtaagtagt tcgccagtta atagtttgcg caacgttgtt gccattgcta   8580
caggcatcgt ggtgtcacgc tcgtcgtttg gtatggcttc attcagctcc ggttcccaac   8640
gatcaaggcg agttacatga tcccccatgt tgtgcaaaaa agcggttagc tccttcggtc   8700
ctccgatcgt tgtcagaagt aagttggccg cagtgttatc actcatggtt atggcagcac   8760
tgcataattc tcttactgtc atgccatccg taagatgctt ttctgtgact ggtgagtact   8820
caaccaagtc attctgagaa tagtgtatgc ggcgaccgag ttgctcttgc ccggcgtcaa   8880
tacgggataa taccgcgcca catagcagaa ctttaaaagt gctcatcatt ggaaaacgtt   8940
cttcggggcg aaaactctca aggatcttac cgctgttgag atccagttcg atgtaaccca   9000
ctcgtgcacc caactgatct tcagcatctt ttactttcac cagcgtttct gggtgagcaa   9060
aaacaggaag gcaaaatgcc gcaaaaaagg aataagggc gacacggaaa tgttgaatac   9120
tcatactctt ccttttttcaa tattattgaa gcatttatca gggttattgt ctcatgagcg   9180
gatacatatt tgaatgtatt tagaaaaata acaaataggg gttccgcgc acatttcccc   9240 gaaaagtgcc acctgacgtc taagaaacca ttattatcat gacattaacc tataaaaata   9300
ggcgtatcac gaggcccttt cgtctcgcgc gtttcggtga tgacggtgaa aacctctgac   9360
acatgcagct cccggagacg gtcacagctt gtctgtaagc ggatgccggg agcagacaag   9420
cccgtcaggg cgcgtcagcg ggtgttggcg ggtgtcgggg ctggcttaac tatgcggcat   9480
cagagcagat tgtactgaga gtgcaccata aaattgtaaa cgttaatatt ttgttaaaat   9540
tcgcgttaaa tttttgttaa atcagctcat ttttaaccaa ataggccgaa atcggcaaaa   9600
tcccttataa atcaaaagaa tagcccgaga tagggttgag tgttgttcca gtttggaaca   9660
agagtccact attaaagaac gtggactcca acgtcaaagg gcgaaaaacc gtctatcagg   9720
gcgatggccc actacgtgaa ccatcaccca aatcaagttt ttggggtcg aggtgccgta   9780 aagcactaaa tcggaaccct aaaggagcc cccgatttag agcttgacgg ggaaagccgg   9840
cgaacgtggc gagaaaggaa gggaagaaag cgaaaggagc gggcgctagg gcgctggcaa   9900
```

-continued

```
gtgtagcggt cacgctgcgc gtaaccacca cacccgccgc gcttaatgcg ccgctacagg    9960
gcgcgtacta tggttgcttt gacgtatgcg gtgtgaaata ccgcacagat gcgtaaggag   10020
aaaataccgc atcaggcgcc attcgccatt caggctgcgc aactgttggg aagggcgatc   10080
ggtgcgggcc tcttcgctat tacgccagct ggcgaaaggg ggatgtgctg caaggcgatt   10140
aagttgggta acgccagggt tttcccagtc acgacgttgt aaaacgacgg ccagtgccc    10199
```